(12) United States Patent
Tran

(10) Patent No.: US 11,596,316 B2
(45) Date of Patent: *Mar. 7, 2023

(54) HEARING AND MONITORING SYSTEM

(71) Applicant: Bao Tran, Saratoga, CA (US)

(72) Inventor: Bao Tran, Saratoga, CA (US)

(*) Notice: Subject to any disclaimer, the term of this patent is extended or adjusted under 35 U.S.C. 154(b) by 162 days.

This patent is subject to a terminal disclaimer.

(21) Appl. No.: 17/110,087

(22) Filed: Dec. 2, 2020

(65) Prior Publication Data
US 2021/0106236 A1 Apr. 15, 2021

Related U.S. Application Data

(63) Continuation of application No. 16/286,518, filed on Feb. 26, 2019, now Pat. No. 10,905,337.

(51) Int. Cl.
*A61B 5/02* (2006.01)
*A61B 5/0205* (2006.01)
(Continued)

(52) U.S. Cl.
CPC .... *A61B 5/02055* (2013.01); *A61B 1/000096* (2022.02); *A61B 1/00194* (2022.02); *A61B 1/05* (2013.01); *A61B 1/227* (2013.01); *A61B 5/026* (2013.01); *A61B 5/0538* (2013.01); *A61B 5/1032* (2013.01); *A61B 5/1117* (2013.01); *A61B 5/1118* (2013.01); *A61B 5/12* (2013.01); *A61B 5/14546* (2013.01); *A61B 5/165* (2013.01); *A61B 5/283* (2021.01); *A61B 5/291* (2021.01); *A61B 5/378* (2021.01); *A61B 5/4803* (2013.01); *A61B 5/6817* (2013.01); *A61B 5/7267* (2013.01); *G05B 13/027* (2013.01); *G05B 13/042* (2013.01); *G06N 20/00* (2019.01); *H04R 25/604* (2013.01); *H04R 25/652* (2013.01); *A61B 5/0816* (2013.01);
(Continued)

(58) Field of Classification Search
CPC ..... A61B 5/02055; A61B 5/291; A61B 5/283; A61B 5/378; A61B 1/05; A61B 1/227; A61B 5/026; A61B 5/0538; A61B 5/1032; A61B 5/1117; A61B 5/1118; A61B 5/12; A61B 5/14546; A61B 5/165; A61B 5/4803; A61B 5/6817; A61B 5/7267; A61B 5/0816; A61B 2560/0247; A61B 2562/0219; G06N 20/00; G05B 13/027; G05B 13/042; H04R 25/604; H04R 25/652; H04R 2225/025; H04R 2225/77
USPC ........................................................ 600/301
See application file for complete search history.

(56) References Cited

U.S. PATENT DOCUMENTS 6,517,482 B1 2/2003 Elden
7,796,271 B2 9/2010 Reithinger
(Continued)

OTHER PUBLICATIONS

Goverdovsky et al, Hearables: Multimodal physiological in-ear sensing, Scientific Reports, vol. 7, Article No. 6948 (Jul. 31, 2017).
(Continued)

Primary Examiner — Aaron F Roane
(74) Attorney, Agent, or Firm — Patent PC

(57) ABSTRACT

Systems and methods for assisting user with hearing by amplifying sound using an amplifier with gain and amplitude controls for a plurality of frequencies; and applying a learning machine to identify an aural environment and adjust the amplifiers for optimum hearing.

21 Claims, 12 Drawing Sheets

(51) Int. Cl.

| | | |
|---|---|---|
| G05B 13/02 | (2006.01) | |
| G05B 13/04 | (2006.01) | |
| A61B 1/227 | (2006.01) | |
| A61B 1/05 | (2006.01) | |
| A61B 5/026 | (2006.01) | |
| A61B 5/00 | (2006.01) | |
| A61B 5/145 | (2006.01) | |
| A61B 5/0538 | (2021.01) | |
| A61B 5/12 | (2006.01) | |
| A61B 5/103 | (2006.01) | |
| A61B 5/11 | (2006.01) | |
| A61B 5/16 | (2006.01) | |
| H04R 25/00 | (2006.01) | |
| G06N 20/00 | (2019.01) | |
| A61B 5/283 | (2021.01) | |
| A61B 5/291 | (2021.01) | |
| A61B 5/378 | (2021.01) | |
| A61B 1/00 | (2006.01) | |
| A61B 5/08 | (2006.01) | |

(52) U.S. Cl.
 CPC .............. *A61B 2560/0247* (2013.01); *A61B 2562/0219* (2013.01); *H04R 2225/025* (2013.01); *H04R 2225/77* (2013.01)

(56) References Cited

U.S. PATENT DOCUMENTS

| | | | |
|---|---|---|---|
| 8,355,518 | B2 | 1/2013 | Niccolai |
| 8,538,033 | B2 | 9/2013 | Wilson |
| 9,259,185 | B2 | 2/2016 | Abdul-hafiz |
| 9,931,021 | B2 | 4/2018 | Ruppersberg |
| 10,024,667 | B2 | 7/2018 | Moore |
| 10,905,337 | B2 * | 2/2021 | Tran ................ A61B 1/045 |
| 2005/0129262 | A1 | 6/2005 | Dillon |
| 2006/0239483 | A1 | 10/2006 | Orts |
| 2008/0269636 | A1 | 10/2008 | Burrows |
| 2011/0290005 | A1 | 12/2011 | Hart |
| 2012/0195448 | A9 | 8/2012 | Abolfathi |
| 2018/0035930 | A1 | 2/2018 | Sokolov |
| 2018/0218507 | A1 | 8/2018 | Hyllus |

OTHER PUBLICATIONS

Park et al, Wearable Sensing of In-Ear Pressure for Heart Rate Monitoring with a Piezoelectric Sensor, Sensors 2015, 15, 23402-23417; doi:10.3390/s150923402 (Sep. 16, 2015).

Huang et al, Disease Classification and Biomarker Discovery Using ECG Data, BioMed Research International vol. 2015, Article ID 680381, 7 pages http://dx.doi.org/10.1155/2015/680381 (Nov. 10, 2015).

Chen et al, Large-scale training to increase speech intelligibility for hearing-impaired listeners in novel noises, J. Acoust. Soc. Am. 139 (5), May 2016.

\* cited by examiner

FIG. 1

| Scan ear (1) |
| Generate 3D model of ear structure (2) |
| 3D Print a Negative of the ear structure with provisioned space for electronics (3) |
| Form a flexible ear insert from the ear structure negative (4) |
| Add amplifier to the ear insert (5) |
| During use, snugly push the ear insert toward the ear canal (6) |
| Render sound (7) |
| Capture medical data as biomarkers including ECG, EGG, physical condition, heart blood flow data, temperature, among others (8) |

FIG. 2A

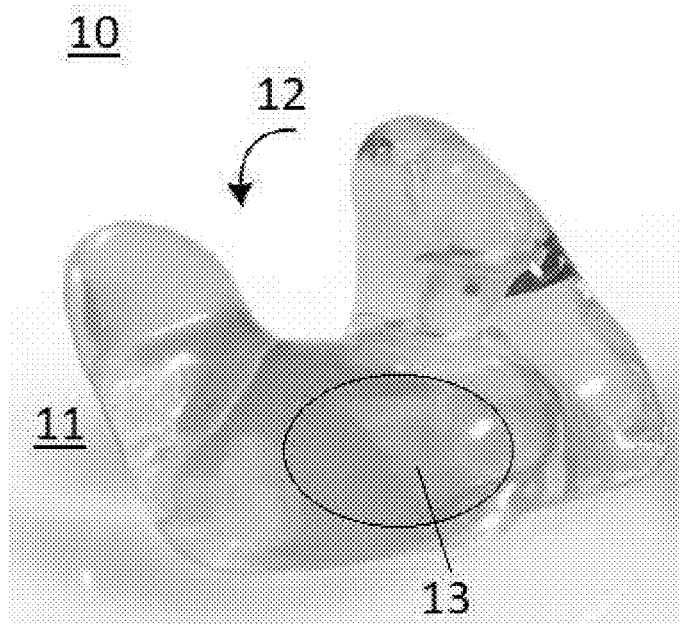

FIG. 2B

FIG. 4A
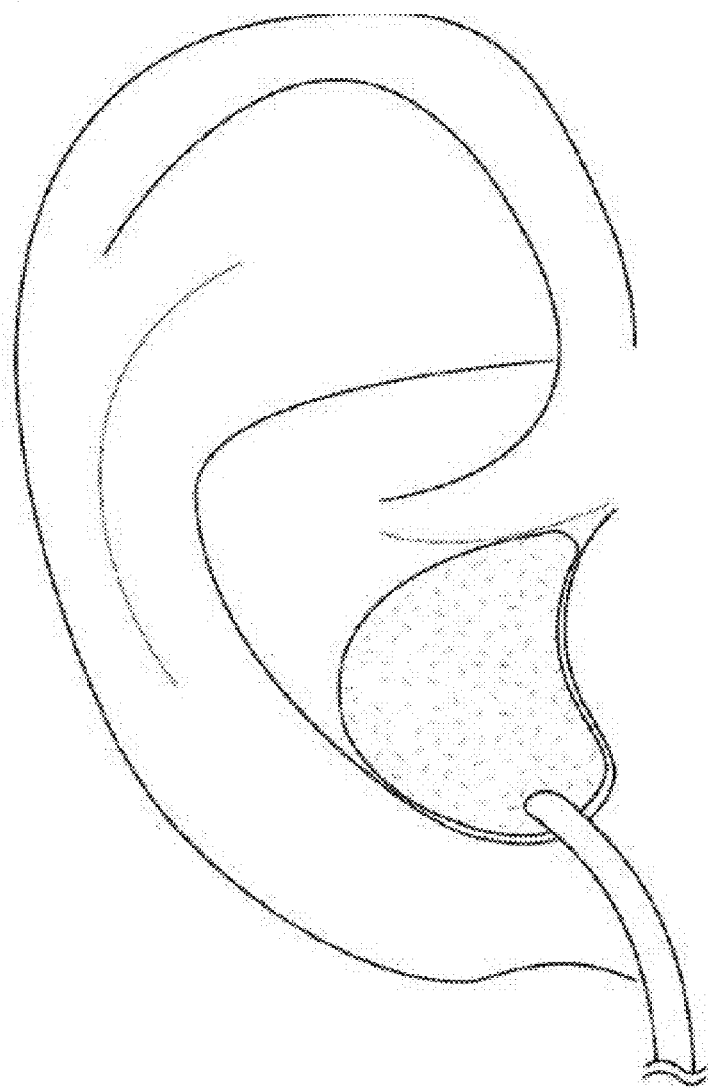
30
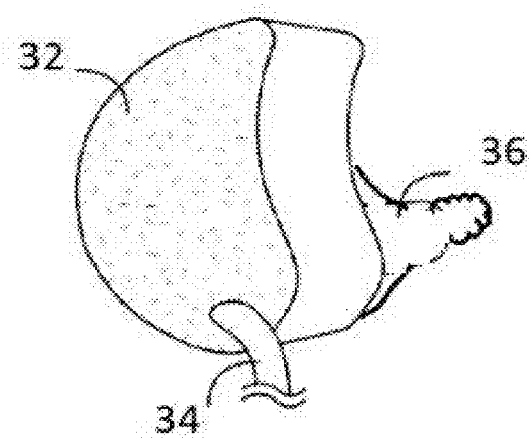
FIG. 4B

FIG. 5A
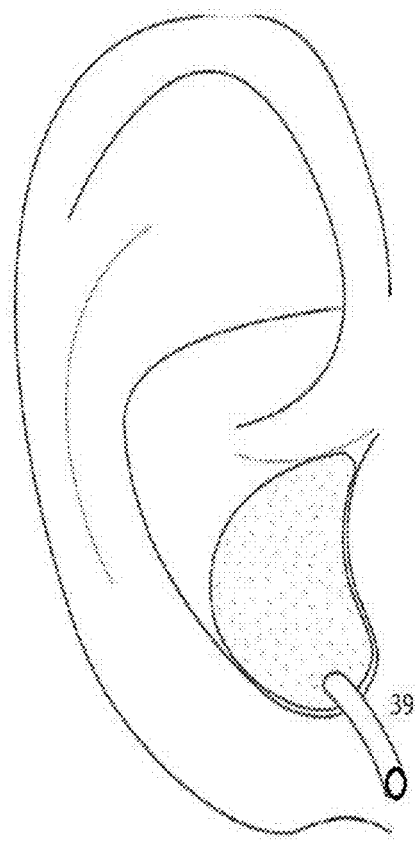
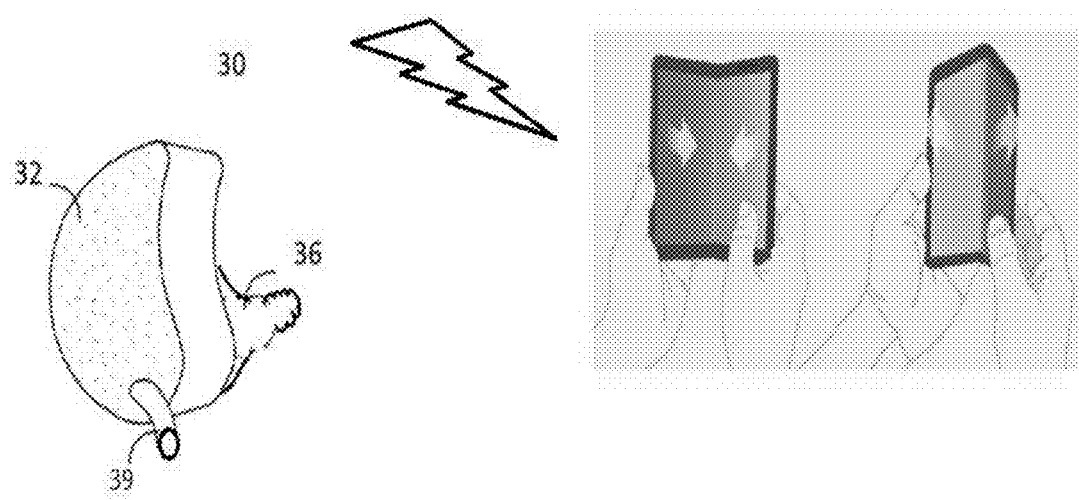
FIG. 5B

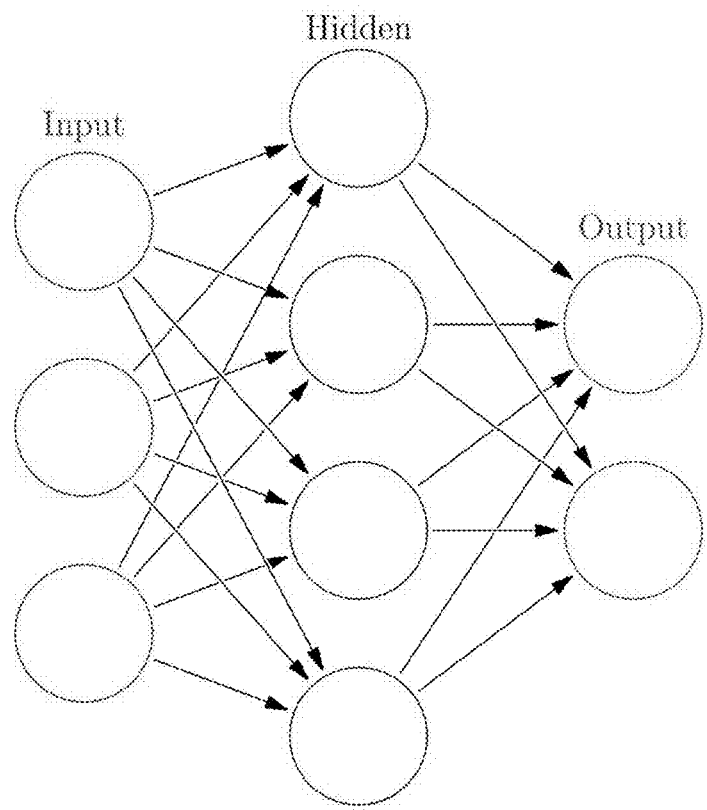
FIG. 7A
FIG. 7B
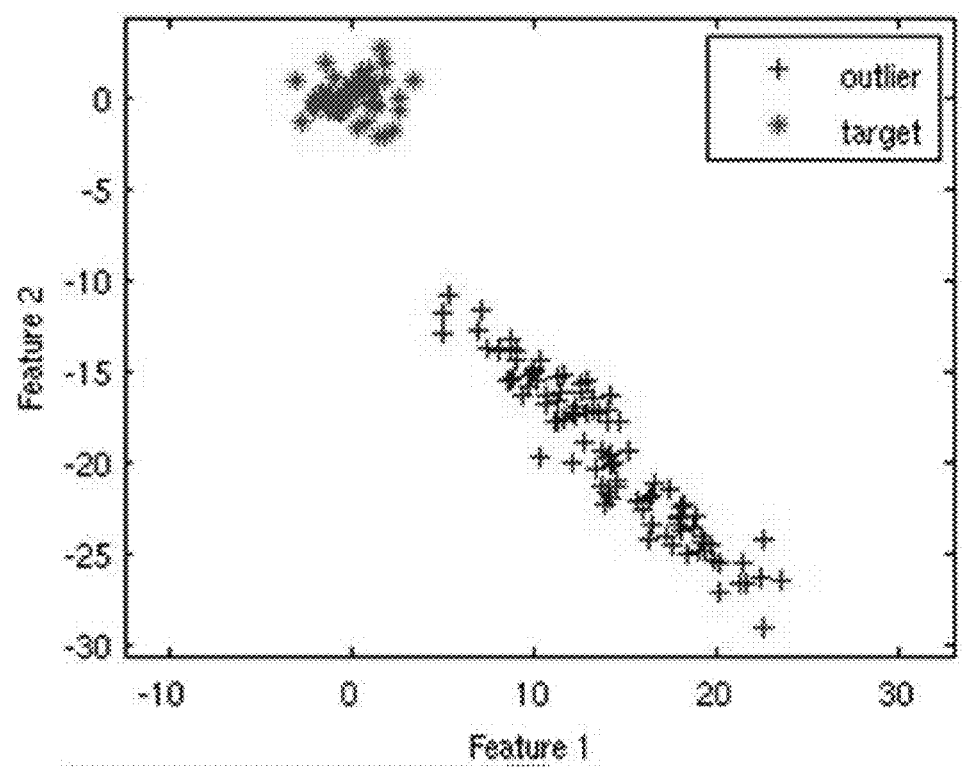

FIG. 7C
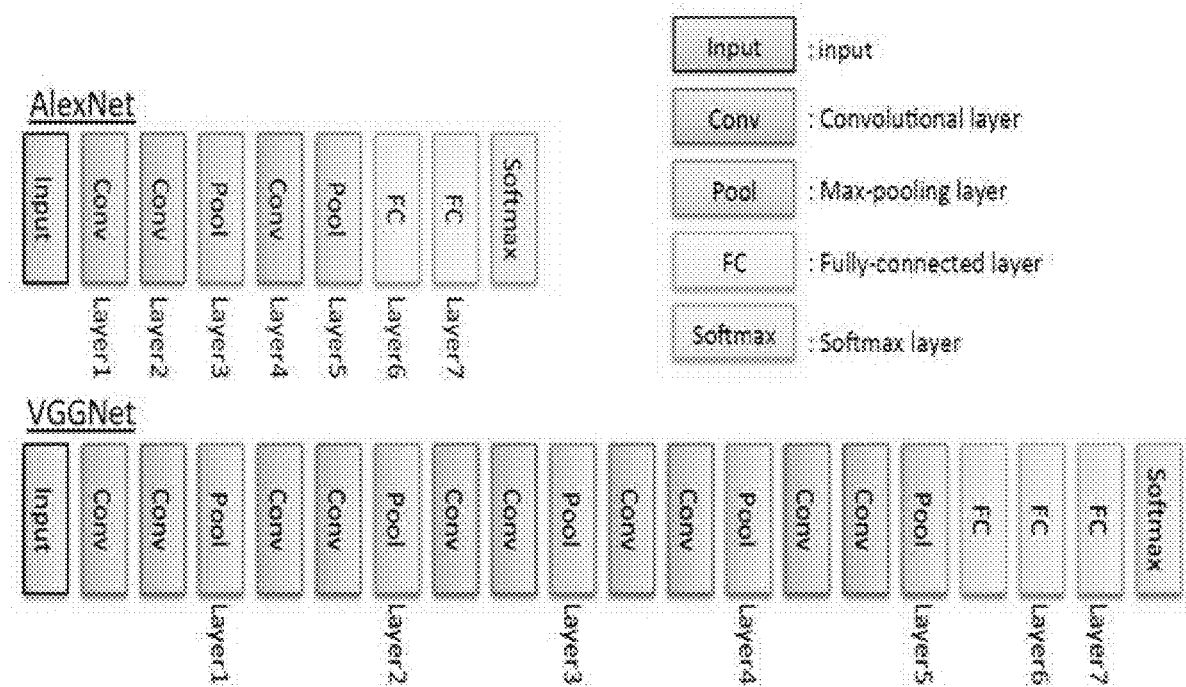
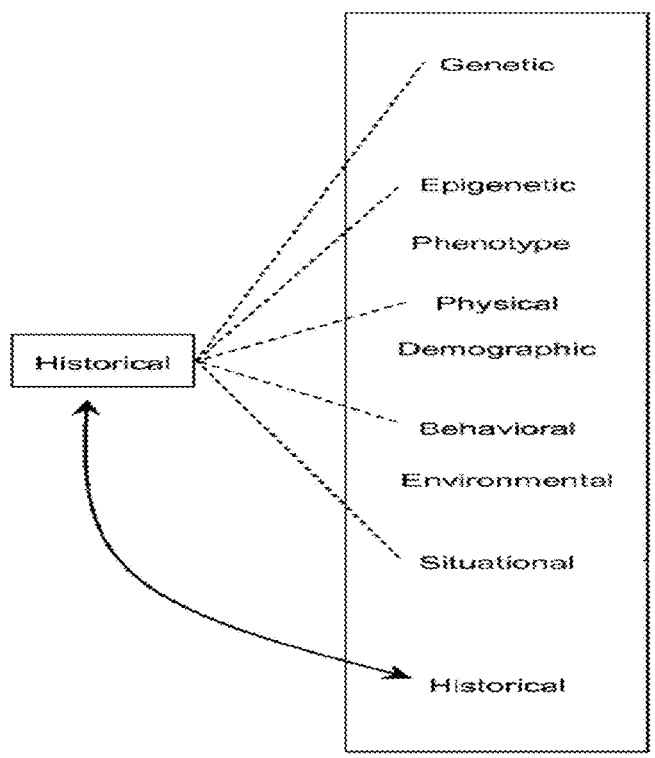
FIG. 7D

FIG. 7E

```
AI consultant is trained on all known literature and expert methodology (499)
Treating physician/doctor logs into a consultation system and "Create New Case" (500).
Initiates "New Case Wizard" with guided "Initial Assessment" form (501).
        enter Patient Information (502)
        enter Initial Assessment of patient/case (504)
        upload Test Results, Patient Photographs and X-Rays (506)
        accept Payment and Service Terms and Conditions (508)
        review Summary of Case (510)
        submit Forms to a consultant such as an Oncology Service Provider (512).
After the case has been submitted, the Service Provider Consultant can log into the system 1 and
consult/process the case (520).
        Using the Treating Doctors Initial Assessment and Photos/X-Rays, the Consultant will click on
"Case Consultation" to initiate the "Case Consultation Wizard" (522).
        AI Consultant can fill out the "Consultant Record Analysis" form (524).
        AI Consultant can also complete the "Prescription Form" (526)
        Submit completed forms to the original Treating Doctor (528).
Treating Doctor accesses completed forms and either accept the consultation results (i.e. a pre-filled
Prescription form) or communicate with the Consultant (530).
Treating Doctor can log into the system (532)
Click on Patient Name to review (534)
Review the Consultation Results (Summary Letter and pre-filled Prescription Form) (536).
If satisfied, the Treating Doctor can click "Approve Treatment" (538)
Mark the case as having being approved (540).
Treating Doctor can print a copy of the Prescription Form and the Summary Letter for submission to
hearing aid provider (542).
If not satisfied, Treating Doctor can initiate a computer dialog with the Consultant by clicking "Send a
Message" (544).
Treating Doctor will be presented with the "Send a Message" screen where a message about the case
under consultation can be written (546).
Treating Doctor would click "Submit" to send the message to the appropriate Consultant (548).
Consultant can reply to the Treating Doctor's Message (550)
```

HEARING AND MONITORING SYSTEM

BACKGROUND

The preferred embodiment relates to in-ear monitoring systems.

Hearing aid appliances with custom fit are known. The "In the Ear (ITE)," "In The Canal" or "Completely In the Canal" types of hearing aids have typically been manufactured using manual labor to a very large extent. Tto produce ITE hearing devices, the shape of the auditory canal to be transferred to the housing shell of an ITE hearing device is determined in as precise a manner as possible. An ear impression of an auditory canal is usually taken in order to produce the shape for a housing shell therefrom. Ear impressions of this type have been read into PC systems by means of scanning for some time, in order then to be further processed digitally. These scanners mostly use the triangulation method for measuring the 3D data of the objects. To this end, a light source (projector) is used, which projects a pattern. This pattern is recorded again by a camera, which is disposed at an angle from the projector. The spatial depth structure can be calculated.

Methods are also known, in which the auditory canal is directly scanned, without requiring an ear impression. These scanners, like those used to record an ear impression, are relatively expensive and are almost exclusively based on triangulation measurement methods, which necessitate precise optical systems and also require a complex system adjustment. Normally, due to the natural curvature of the ear canal, the eardrum is not visible from outside the ear. In order to overcome the natural curvature of the ear canal, a skilled operator or physician has to carefully pull the outer ear upward and to the back while carefully pushing the tip of the scanner into the ear canal as deeply as necessary to display the eardrum. The ear canal has to be deformed in such a way that the physician has a free view onto the eardrum along the optical axis of the camera. The procedure needs manual skills and significant training to carefully push the funnel into the ear canal while looking inside and manipulating the curvature of the ear canal by pulling the ear. For example, the trained operator is well aware to brace the hand holding of the camera against the subject's head to avoid injury to the ear canal and the eardrum by placing the index finger or little finger against the head. Thus, the risk of penetration of the sensitive ear canal skin or even of the eardrum exists. Other than pain and handicapped hearing, such an injury is also known to potentially induce cardiovascular complication through vagal overstimulation and, therefore, has to be avoided under all circumstances.

SUMMARY

In one aspect, systems and methods for assisting a user include a housing custom fitted to a user anatomy; a microphone to capture sound coupled to a processor to deliver enhanced sound to the user anatomy; an amplifier with gain and amplitude controls for each hearing frequency; and a learning machine (such as a neural network) to identify an aural environment (such as party, movie, office, or home environment) and adjusting amplifier controls to optimize hearing based on the identified aural environment. In one embodiment, the environment can be identified by the background noise or inferred through GPS location, for example.

In another aspect, a method for assisting a user includes customizing an in-ear device to a user anatomy; capturing sound using the in-ear device; enhancing sound based on predetermined profiles and transmitting the sound to an ear drum.

In yet another aspect, a method for assisting a user includes customizing an in-ear device to a user anatomy; capturing sound using the in-ear device; capturing vital signs with the in-ear device; and learning health signals from the sound and the vital signs from the in-ear device.

In a further aspect, a method includes customizing an in-ear device to a user anatomy; capturing vital signs with the in-ear device; and learning health signals from the vital signs from the in-ear device.

In another aspect, a method includes customizing an in-ear device to a user anatomy; capturing vital signs to detect biomarkers with the in-ear device; correlating genomic disease markers with the detected biomarkers to predict health with the in-ear device.

In another aspect, a method includes customizing an in-ear device to a user anatomy; identifying genomic disease markers; capturing vital signs to detect biomarkers with the in-ear device; correlating genomic disease markers with the detected biomarkers to predict health with the in-ear device.

In another aspect, a method includes customizing an in-ear device to a user anatomy; capturing accelerometer data and vital signs; controlling a virtual reality device or augmented reality device with acceleration or vital sign data from the in-ear device.

In another aspect, a method includes customizing an in-ear device to a user anatomy; capturing heart rate, EEG or ECG signal with the in-ear device; and determining user intent with the in-ear device. The determined user intent can be used to control an appliance, or can be used to indicate interest for advertisers.

In another aspect, a method includes customizing an in-ear device to a user anatomy; capturing heart rate, EEG/ ECG signal or temperature data to detect biomarkers with the in-ear device; and predict health with the in-ear device data.

In another aspect, a method includes customizing an in-ear device to a user anatomy; capturing sounds from an advertisement, capturing vital signs associated with the advertisement; and customizing the advertisement to attract the user.

In another aspect, a method includes customizing an in-ear device to a user anatomy; capturing vital signs associated with a situation; detecting user emotion from the vital signs; and customizing an action based on user emotion. In one embodiment, such detected user emotion is provided to a robot to be more responsive to the user.

In another aspect, a method includes customizing an in-ear device to a user anatomy; capturing a command from a user, detecting user emotion based on vital signs; and performing an action in response to the command and the detected user emotion.

In another aspect, a method includes customizing an in-ear device to a user anatomy; capturing a command from a user, authenticating the user based on a voiceprint or user vital signs; and performing an action in response to the command.

In one aspect, a method for assisting a user includes customizing an in-ear device to a user anatomy; capturing sound using the in-ear device; enhancing sound based on predetermined profiles and transmitting the sound to an ear drum.

In one aspect, a method for assisting a user includes providing an in-ear device to a user anatomy; capturing sound using the in-ear device; capturing vital signs with the in-ear device; and learning health signals from the sound and the vital signs from the in-ear device.

In another aspect, a method includes providing an in-ear device to a user anatomy; capturing vital signs with the in-ear device; and learning health signals from the vital signs from the in-ear device.

In another aspect, a method includes providing an in-ear device to a user anatomy; capturing vital signs to detect biomarkers with the in-ear device; correlating genomic disease markers with the detected biomarkers to predict health with the in-ear device.

In another aspect, a method includes providing an in-ear device to a user anatomy; identifying genomic disease markers; capturing vital signs to detect biomarkers with the in-ear device; correlating genomic disease markers with the detected biomarkers to predict health with the in-ear device.

In another aspect, a method includes providing an in-ear device to a user anatomy; capturing accelerometer data and vital signs; controlling a virtual reality device or augmented reality device with acceleration or vital sign data from the in-ear device.

In another aspect, a method includes providing an in-ear device to a user anatomy; capturing heart rate, EEG or ECG signal with the in-ear device; and determining user intent with the in-ear device. The determined user intent can be used to control an appliance, or can be used to indicate interest for advertisers.

In another aspect, a method includes providing an in-ear device to a user anatomy; capturing heart rate, EEG/ECG signal or temperature data to detect biomarkers with the in-ear device; and predict health with the in-ear device data.

In another aspect, a method includes providing an in-ear device to a user anatomy; capturing sounds from an advertisement, capturing vital signs associated with the advertisement; and customizing the advertisement to attract the user.

In another aspect, a method includes providing an in-ear device to a user anatomy; capturing vital signs associated with a situation; detecting user emotion from the vital signs; and customizing an action based on user emotion. In one embodiment, such detected user emotion is provided to a robot to be more responsive to the user.

In another aspect, a method includes providing an in-ear device to a user anatomy; capturing a command from a user, detecting user emotion based on vital signs; and performing an action in response to the command and the detected user emotion.

In another aspect, a method includes providing an in-ear device to a user anatomy; capturing a command from a user, authenticating the user based on a voiceprint or user vital signs; and performing an action in response to the command.

In another aspect, a method includes providing an in-ear device to a user anatomy; determine an audio response chart for a user based on a plurality of environments (restaurant, office, home, theater, party, concert, among others), determining a current environment, and updating the hearing aid parameters to optimize the amplifier response to the specific environment. The environment can be auto detected based on GPS position data or external data such as calendaring data or can be user selected using voice command, for example. In another embodiment, a learning machine automatically selects an optimal set of hearing aid parameters based on ambient sound and other confirmatory data.

Implementations of any of the above aspects may include one or more of the following:
detecting electrical potentials encephalography (EEG) or electrocardiogram (ECG) in the ear;
using a camera in the ear to detect ear health;
detecting blood flow with an in-ear sensor;
detecting with an in-ear sensor blood parameters including carboxyhemoglobin (HbCO), methemoglobin (HbMet) and total hemoglobin (Hbt);
detecting pressure based on a curvature of an ear drum;
detecting body temperature in the ear;
detecting one or more of: alpha rhythm, auditory steady-state response (ASSR), steady-state visual evoked potentials (SSVEP), visually evoked potential (VEP), visually evoked response (VER) and visually evoked cortical potential (VECP), cardiac activity, speech and breathing;
detecting alpha rhythm, auditory steady-state response (ASSR), steady-state visual evoked potentials (SSVEP), and visually evoked potential (VEP);
correlating EEG, ECG, speech and breathing to determine health;
correlating cardiac activity, speech and breathing;
determining user health by detecting fluid in an ear structure, change in ear color, curvature of the ear structure;
determining one or more bio-markers from the vital signs and indicating user health;
performing a 3D scan inside an ear canal;
matching predetermined points on the 3D scan to key points on a template and morphing the key points on the template to the predetermined points;
3D printing a model from the 3D scan and fabricating the in-ear device;
correlating genomic biomarkers for diseases to the vital signs from the in-ear device and applying a learning machine to use the vital signs from the in-ear device to predict disease conditions;
determining a fall based on accelerometer data, vital signs and sound;
determining loneliness or mental condition based on activity of life data; or
providing a user dashboard showing health data over a period of time and matching research data on the health signals.

Advantages of the preferred embodiments may include one or more of the following. By using the disclosed data analysis method, a health system can add a new method of collecting and analyzing patient information. Patients can be assured that there is quantitative, objective information. For most medical conditions, biomarker pattern can be obtained and compared against known conditions. The system supplies adjunctive information by which the health practitioner may make a better decision regarding treatment alternatives. Appropriate measurement yields tremendous information to the doctors and users. This information improves diagnosis, aids in better treatment, and allows for earlier detection of problems.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

Other systems, methods, features, and advantages of the present system will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

FIG. 1 shows an exemplary process to render sound and to monitor a user.

FIGS. 2A-2B show a custom monitoring device.

FIGS. 4A-4B show another custom hearing aid and monitoring device.

FIGS. 5A-5B show another custom hearing aid and monitoring device with extended camera, microphone and antenna.

FIG. 7A shows a neural network, FIG. 7B shows an exemplary analysis with normal targets and outliers as warning labels, FIG. 7C show an exemplary learning system, FIG. 7D shows a medical AI system with the learning machines, and FIG. 7E show an exemplary AI based expert consultation system with human healthcare personnel.

FIG. 8A-8C shows exemplary coaching system for skiing, bicycling, and weightlifting/free style exercise, respectively, while

Similar reference characters denote corresponding features consistently throughout the attached drawings.

DETAILED DESCRIPTION OF THE INVENTION

Figure 3A:
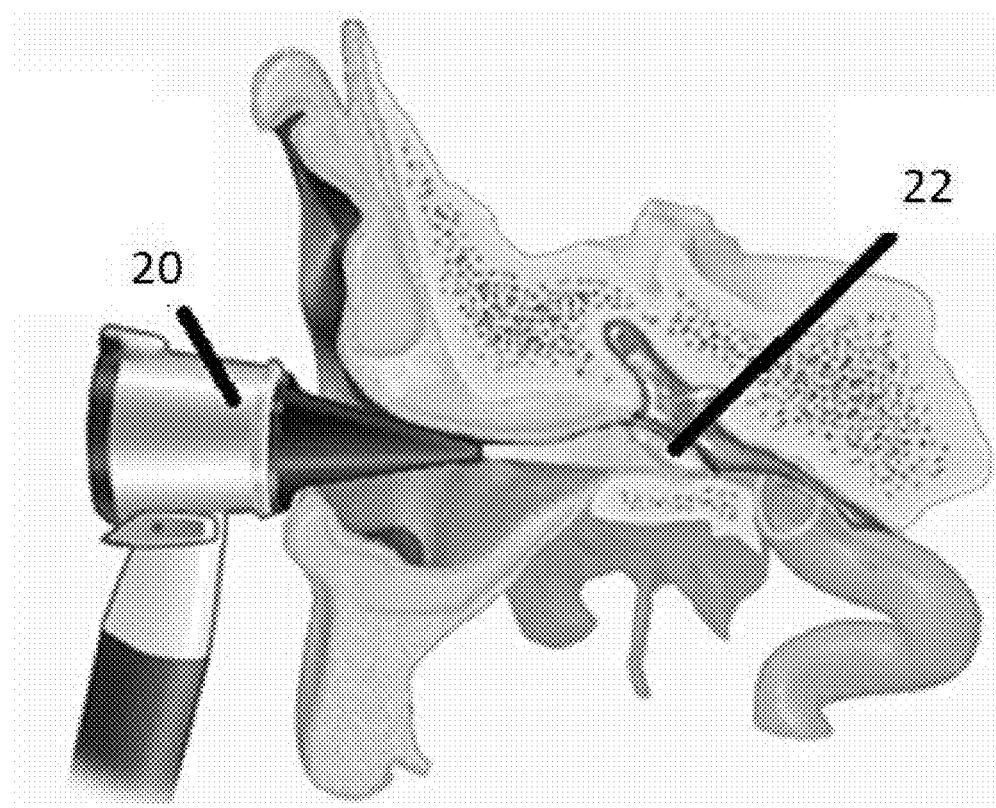
FIG. 3A shows an exemplary scanner to scan ear structures.

A system to create a custom medical device insertable into the ear is described. The system uses an ear scanner to create a 3D model of the ear structure, and a 3D printer that reproduces the shape (or the negative of the shape) of the ear, wherein an ear insert can be formed from the shape of the ear. Suitable sensors and transducers are then added to the custom ear insert. The result custom ear insert is comfortable to wear and blocks out extraneous sound or noise.

FIG. 1 shows an exemplary process to form and use a custom ear insert as a hearing aid with vital sign monitoring. The process is as follows:

Scan ear (1)
Generate 3D model of ear structure (2)
3D Print a Negative of the ear structure with provisioned space for electronic module (3)
Form a flexible ear insert from the ear structure negative (4)
Insert or add amplifier to the provisioned space to the ear insert (5)
During use, snugly push the ear insert toward the ear canal (6)
Render sound (7)
Capture medical data as biomarkers including ECG, EGG, physical condition, heart rate, blood flow data, temperature (8)

FIGS. 2A-2B show an exemplary ear insert that is injection molded with a pliant material. In one embodiment, the material is a medical grade thermoplastic elastomer. The device can render sound for the user, and can also collect medical data such as oxygenation or other blood constituents or temperature, for example.

Turning now to FIG. 2A, an ear monitoring device 10 includes a customized shell 12 for reception in the ear canal of a person. The shell 12 has an opening 13 to receive the hearing aid 10 when mounted. In general, the shell 12 has the frontally facing part pointing outward from the person's ear canal when the shell is positioned therein and the frontally facing part has an opening 13 to receive an electronic module therein. The part of the shell 12 actually engaging the user's ear canal is denoted 11.

Ambient sound from the environment is picked up and amplified by the device of FIG. 2A-2B. Based on a hearing test, the amplifier frequency response is enhanced based on the ear structure and the user's hearing deficiencies. For example, certain sound frequencies are not perceived well by certain users, and the system would compensate for such frequency hearing deficiency. Moreover, at user request, the frequency bandwidth can be adjusted to specific situations, for example, to selectively focus on bird sounds or voice from a particular person or species. The enhanced or amplified sound moves through the ear canal and causes the eardrum to move. The eardrum vibrates with sound. Sound vibrations move through the ossicles to the cochlea. Sound vibrations cause the fluid in the cochlea to move. Fluid movement causes the hair cells to bend. Hair cells create neural signals which are picked up by the auditory nerve. Hair cells at one end of the cochlea send low pitch sound information and hair cells at the other end send high pitch sound information. The auditory nerve sends signals to the brain where they are interpreted as sounds.

The body of the device may be generated using suitable 3D printing techniques including printing of a positive or negative of the ear using stereo lithography ("SLA") or stereo laser sintering ("SLS") production methods and/or injection molding techniques. In one embodiment, a negative of the body is 3D printed and silicone or rubber is provided using injection molding. While an electronic module can be snap fit into the opening 13 and occupy the provisioned space, the module can be secured with an intermediary frame. This frame may be fixed in the opening 13 by any suitable means, such as adhesives, welding (laser welding, heat welding), soldering, or as a press fit. The intermediary frame may be permanently or removably fixed in the opening 13. Any dimensional slack between the intermediary frame and the opening 13 may be filled by adhesive or by a sealing member of any suitable type (foam, rubber or other resilient material or the like). An electronic module (not shown) is adapted to be removably fixed in the intermediary frame in order to facilitate replacement or repair thereof. The electronics module can be flexible electronics, as detailed in commonly owned application Ser. No. 16/237,697, the content of which is incorporated by reference. This insertion of the electronic module may be a click fixing or a combination of a clicking of a rod or axis into the intermediary frame and a subsequent rotation and fixing of the electronic module in the intermediary frame. This manner of fixing may be that normally used in the prior art when fixing an electronic module to a shell.

The discussion already given above in the introduction to the specification provide the expert with a large number of designs, depending on the ear hearing aid and monitoring device or its configuration, to jointly manufacture two or more pertinent elements by two- or multi-component injection molding, in particular also by overmolding and then to assemble them jointly into an integral part.

Figure 3B:
FIG. 3B shows a smart-phone scanner.

FIG. 3A shows an exemplary ear scanner 30 with a camera mounted on a tip that is inserted into the ear canal that terminates at an ear drum 32. The camera captures images that are converted into point cloud, as shown in FIG. 3B. In one embodiment, as the user or operator passes the camera of the scanner in the ear, a point cloud is generated and a 3D model of the ear is constructed. The 3D model is used to construct the device of FIG. 2, and further used in the sound modeling process to optimize electronic performance for hearing.

The scanner 20 has camera(s) that pick up a plurality of images which are then used to reconstruct a 3D model of the ear structure. The tip of the scanner 20 is made sufficiently large that it cannot accidentally be inserted too far into the ear canal as to puncture the ear drum or otherwise harm the ear. The optics of the scanner 20 has a lamp and a lens and the camera view angle provides at least one eccentric observation point and/or at least one light source (preferably both) into an ear canal of a subject's outer ear and capturing imaged from the eccentric position. In particular, an optical axis does not have to correspond to the longitudinal axis of the head portion. Instead, an optical axis of the electronic imaging unit may be arranged radially offset.

In particular, in many cases, the ear canal of the outer ear is not straight-lined, but exhibits at least one curvature, especially at a transition area or transition point between soft connective tissue and hard bone confining the ear canal. The "corner" is provided by this curvature and the requirement to deform the subject's ear is eliminated or greatly reduced. Furthermore, the inventive method avoids the risk of injury to the ear canal, in particular the bony part of the ear canal, or to the eardrum by allowing the use of otoscopes with a tip of the head portion that exhibit significantly larger dimensions as compared to an otoscope according to the art. Thus, the risk of introducing the head portion of the camera too deeply into the subject's ear canal is considerably reduced so that cell phone user or a layperson can to use the scanner 20. This cuts down on cost. An eccentric position or observation point allows for "looking around the corner". In particular, the eardrum can be observed in its entirety, even in case the distal tip of the camera is introduced only as far as a transition area between soft connective tissue and hard bone confining the ear canal. The larger the radial offset, the better the view onto the eardrum, even in case a distal end of the camera is positioned only in a transition area between soft connective tissue and hard bone confining the ear canal. Preferably, capturing the at least one image is carried out from an eccentric observation point which is positioned closer than 1.5 mm, more preferable closer than 1.0 mm, further preferred closer than 0.8 mm or even closer than 0.7 mm or 0.6 mm to an inner lateral surface of the ear canal, especially with respect to a diameter of the ear canal in the range between 4.8 mm and 5.2 mm. A guide facility allows the camera in the ear canal to be pivoted, rotated and moved along the ear canal. The curved ear canal can thus be recorded in a desired fashion.

Once at least one image has been captured by the at least on electronic imaging unit, object recognition and unambiguous object identification (e.g. distinguishing objects, such as earwax, hair, and the eardrum) can be performed by determining brightness and/or color information of the pixels of the at least one captured image. Each pixel of the image obtained by the electronic imaging unit is characterized by a numerical value corresponding to the brightness of that pixel and—if the electronic imaging device comprises a color imaging device—also by a numerical value corresponding to the color of that pixel. Different objects can be identified e.g. by their typical color. The earwax or obstacles can be digitally removed from the 3D model, and the user can be notified to clean the ear. Alternatively, a vacuum embedded in the tip can be used to suction or remove wax, hair, and other debris from the ear structures to clean and capture the 3D model at the same time.

With these features, the electronic imaging unit is suitable to capture at least two images from different positions within the ear canal, e.g. by relocating one single electronic imaging unit when placed in the subject's ear canal and/or by providing images from two or more electronic imaging units positioned at different sites in the ear canal. Alternatively or additionally, the method may be based on the implementation of at least one illumination unit which is adapted to illuminate objects within the ear canal from different positions (e.g. from two or more positions). Preferably, a combination of both approaches is realized by the inventive method, which allows capturing images from different positions under differing illumination conditions. Such a mode of action allows for reliable identification of distinct objects (e.g. the eardrum, particles of earwax, hair, etc. in the subject's ear), as will be described in more detail below. Thereby, the risk of image misinterpretation and failure in object recognition is significantly reduced.

In one embodiment, a three-dimensional video may be created with a series of time-separated measurements. In another aspect, the camera may be moved (in a translation, a rotation, or some combination of these) in order to capture a larger area of interest or the entire ear structure, or in order to obtain measurements of occluded surfaces of the ear structure, or for any other reason. In such a motion-based imaging process, the relative positions of the camera, the ear structure, and/or the medium 106 may be physically tracked with motion sensors or the like, or the relative motion may be inferred using a three-dimensional registration process to spatially relate successive three-dimensional data sets to one another. Regardless of the particular methodology, it will be readily appreciated that individual spatial measurements, or groups of spatial measurements, may be combined to form a larger three-dimensional model, and all such techniques that would be apparent to one of ordinary skill in the art for creating a three-dimensional reconstruction are intended to fall within the scope of this disclosure.

In another aspect, a desktop computer may provide a user interface for control and operation of the system of FIG. 3A or 3B, as well as tools for displaying ear structure measurements, displaying or manipulating reconstructed three-dimensional models, and so forth. The computer may also support calibration of the camera in order to correct for, e.g., variations in the camera, and related optics, or variations in concentration of additives to the medium that absorb, scatter, attenuate, fluoresce, or otherwise impart various optical properties. For example and without limitation, it will be understood that one can characterize the camera using a calibration fixture or the like, prior to employing the camera. Calibration may, for example, include the use of an ear structure having a known shape and a known position, or the use of a container for the medium having a known shape. A variety of suitable calibration techniques will be readily appreciated based upon the use of known shapes, dimensions, surface patterns, and so forth, any of which may be adapted to use with the imaging systems described herein.

FIG. 3B shows a smart phone scanner embodiment. In this embodiment, scanned ear structures can be detected on any ARKit. When first run, the app displays a box that roughly estimates the size of whatever real-world objects appear centered in the camera view. Before scanning, the system determines a region of the world contains the ear structures. The ear is scanned, and the camera is moved to scan from different angles. The app highlights parts of the bounding box to indicate sufficient scanning to recognize the object from the corresponding direction.

To enable object detection in an AR session, load the reference objects as ARReferenceObject instances, provide those objects for the detectionObjects property of an ARWorldTrackingConfiguration, and run an ARSession with that configuration. When ARKit detects one of your reference ear structures, the session automatically adds a corresponding ARObjectAnchor to its list of anchors. To respond to an object being recognized, implement an appropriate ARSessionDelegate, ARSCNViewDelegate, or ARSKViewDelegate method that reports the new anchor being added to the session.

A reference object encodes a slice of the internal spatial-mapping data that ARKit uses to track a device's position and orientation. To enable the high-quality data collection required for object scanning, run a session with ARObjectScanningConfiguration:

let configuration=ARObjectScanningConfiguration( )
configuration.planeDetection=.horizontal
sceneView.session.run(configuration, options: .resetTracking)

During your object-scanning AR session, scan the object from various angles to make sure you collect enough spatial data to recognize it. (If you're building your own object-scanning tools, help users walk through the same steps this sample app provides.)

After scanning, call createReferenceObject(transform: center:extent:completionHandler:) to produce an ARReferenceObject from a region of the user environment mapped by the session:

```
// Extract the reference object based on the position & orientation of the bounding box.
sceneView.session.createReferenceObject(
    transform: boundingBox.simdWorldTransform,
    center: float3( ), extent: boundingBox.extent,
    completionHandler: { object, error in
        if let referenceObject = object {
            // Adjust the object's origin with the user-provided transform.
            self.scannedReferenceObject = referenceObject.applyingTransform(origin.simdTransform)
            self.scannedReferenceObject!.name = self.scannedObject.scanName
                        if let referenceObjectToMerge = ViewController.instance?.referenceObjectToMerge {
                ViewController.instance?.referenceObjectToMerge = nil
                            // Show activity indicator during the merge.
                ViewController.instance?.showAlert(title: "", message: "Merging previous scan into this scan...", buttonTitle: nil)
                            // Try to merge the object which was just scanned with the existing one.
                self.scannedReferenceObject?.mergeInBackground(with: referenceObjectToMerge, completion: { (mergedObject, error) in
                    if let mergedObject = mergedObject {
                        mergedObject.name = self.scannedReferenceObject?.name
                        self.scannedReferenceObject = mergedObject
                        ViewController.instance?.showAlert(title: "Merge successful",
                                message: "The previous scan has been merged into this scan.", buttonTitle: "OK")
                        creationFinishe(self.scannedReferenceObject)
                    } else {
                        print("Error: Failed to merge scans. \(error?.localizedDescription ?? "")")
                        let message = """
                                Merging the previous scan into this scan failed. Please make sure that
                                there is sufficient overlap between both scans and that the lighting
                                environment hasn't changed drastically.
                                Which scan do you want to use for testing?
                                """
                        let thisScan = UIAlertAction(title: "Use This Scan", style: .default) {_ in
                            creationFinished(self.scannedReferenceObject)
                        }
                        let previousScan = UIAlertAction(title: "Use Previous Scan", style: .default) {_ in
                            self.scannedReferenceObject = referenceObjectToMerge
                            creationFinished(self.scannedReferenceObject)
                        }
                        ViewController.instance?.showAlert(title: "Merge failed", message: message, actions: [thisScan, previousScan])
                    }
                })
            } else {
                creationFinished(self.scannedReferenceObject)
            }
        } else {
            print("Error: Failed to create reference object. \(error!.localizedDescription)")
            creationFinished(nil)
        }
    })
```

After getting an ARReferenceObject, the system can use it for detection and dimension determination.

Figure 3C:
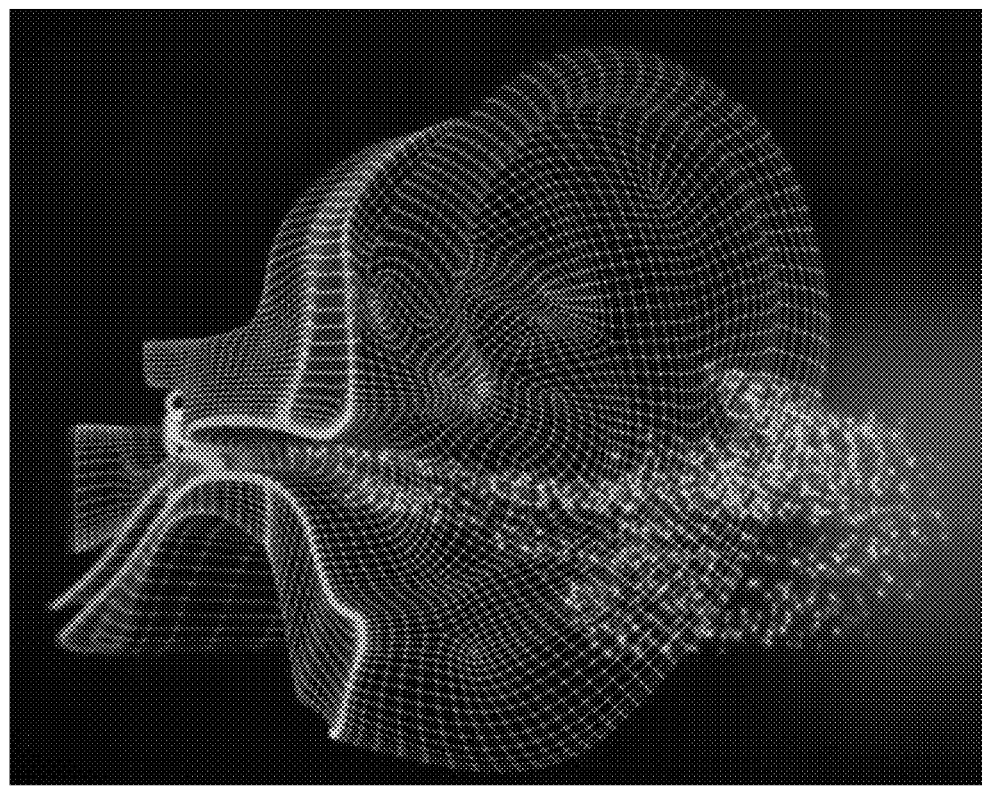
FIG. 3C shows exemplary point clouds from the camera(s).

As shown in the embodiment of FIG. 3C, a mesh model is formed from the dimensional data. The reconstruction starts with a rough alignment of a dummy mesh model to the point cloud data. In order to simplify integration of the ear model into a head model at a later stage, the dummy mesh model is prepared such that it includes part of the head as well. The mesh part of the head is cropped such that it comprises a rough ear plane, which can be matched with an ear plane of the point cloud. An exemplary dummy mesh model is represented in FIG. 3C.

The rough alignment of the dummy mesh model is split into two stages. First the model is aligned to the data in 3D. Then orientation and scale of the model ear are adapted to roughly match the data. The first stage preferably starts with extracting a bounding box for the ear. This can be done automatically using ear detection techniques. Alternatively, the ear bounding box extraction is achieved by simple user interaction. From one of the images used for reconstructing the ear, which contains a lateral view of the human head, the user selects a rectangle around the ear. Advantageously, the user also marks the top point of the ear on the helix. These simple interactions avoid having to apply involved ear detection techniques. From the cropping region a bounding box around the ear is extracted from the point cloud. From this cropped point cloud two planes are estimated, one plane HP for the head points and one plane EP for the points on the ear using a RANSAC plane fit process.

The ear plane is mainly used to compute the transformation necessary to align the ear plane of the mesh model with that of the point cloud. The fit enables a simple detection of whether the point cloud shows the left ear or the right ear based on the ear orientation (obtained, for example, from the user input) and the relative orientation of the ear plane and the head plane. In addition, the fit further allows extracting those points of the point cloud that are close to the ear plane. From these points the outer helix line can be extracted, which simplifies estimating the proper scale and the ear-center of the model. To this end, from the extracted points of the point cloud a depth map of the ear points is obtained. This depth map generally is quite good, but it may nonetheless contain a number of pixels without depth information. In order to reduce this number, the depth map is preferably filtered. For example, for each pixel without depth information the median value from the surrounding pixels may be computed, provided there are sufficient surrounding pixels with depth information. This median value will then be used as the depth value for the respective pixel. A useful property of this median filter is that it does not smooth the edges from the depth map, which is the information of interest. Edges are extracted from the filtered depth map. This may be done using a canny edge detector. From the detected edges connected lines are extracted. In order to finally extract the outer helix, the longest connected line on the right/left side for a left/right ear is taken as a starting line. This line is then down-sampled and only the longest part is taken. The longest part is determined by following the line as long as the angle between two consecutive edges, which are defined by three consecutive points, does not exceed a threshold. As a starting point, a small down-sampling factor is chosen and is then iteratively increased. Only the factor that gives the longest outer helix is kept. This technique allows "smoothing" the line, which could be corrupted by some outliers. It is further assumed that the helix is smooth and does not contain abrupt changes of the orientation of successive edges, which is enforced by the angle threshold. Depending on the quality of the data, the helix line can be broken. As a result, the first selected line may not span the entire helix bound.

With the foregoing information the rough alignment can be computed. To this end the model ear plane is aligned to the ear plane in the point cloud. Then the orientation of the model ear is aligned with that of the point cloud ear by a rotation in the ear plane. Following the rough alignment a finer elastic transformation is applied in order to fit the mesh model to the data points. This is a specific instance of a non-rigid registration technique. Since the ear is roughly planar and hence can be characterized well by its 2D structure, the elastic transformation is performed in two steps. First the ear is aligned according to 2D information, such as the helix line detected before. Then a guided 3D transformation is applied, which respects the 2D conditions. The two steps will be explained in more detail in the following. For model preparation an ear region of the mesh model is selected, e.g. by a user input. This selection allows classifying all mesh model vertices as belonging to the ear or to the head. An example of a selected ear region of a mesh model shows that the ear region is indicated by the non-transparent mesh.

For the non-rigid alignment the mesh model can be deformed to match the data points by minimizing a morphing energy consisting of: a point-to-point energy for a model vertex and its closest data-point; a point-to-plane energy for a model vertex, its closest data-point, and the normal of it; a global rigid transformation term; and a local rigid transformation term. This allows an elastic transformation. However, this energy is adapted for the present solution, as will be described below. Note that only the 2D locations of all the points in the ear plane are considered.

Next, sensors are detailed. An ear site has the advantage of more quickly and more accurately reflecting oxygenation changes in the body's core as compared to peripheral site measurements, such as a fingertip. Conventional ear sensors utilize a sensor clip on the ear lobe. However, significant variations in lobe size, shape and thickness and the general floppiness of the ear lobe render this site less suitable for central oxygen saturation measurements than the concha and the ear canal. Disclosed herein are various embodiments for obtaining noninvasive blood parameter measurements from concha 120 and ear canal 130 tissue sites.

In another embodiment, a hologram scanner can be used. The device for recording the spatial structure of at least one part of an ear canal or ear impression uses a holography unit with a light source and by means of which a hologram of the ear canal can be adjusted. A semitransparent disk in the ear is used for separating the light beam from the light source into an illumination beam and a reference beam. A sensor records an object beam, which is produced by reflection of the illumination beam onto the part of the ear canal, together with the reference beam. The hologram recording system can essentially be constructed within smaller dimensions than a conventional 3D scanner, which is based on the triangulation principle. The hologram recording system can be constructed within significantly smaller dimensions than the 3D scanner. The hologram sensor (CCD chip) does not require a front lens, since it does not record a mapping of an image, but instead interference patterns on its surface One aspect of an ear sensor optically measures physiological parameters related to blood constituents by transmitting multiple wavelengths of light into a concha site and receiving the light after attenuation by pulsatile blood flow within the concha site. The ear sensor comprises a sensor body, a sensor connector and a sensor cable interconnecting the sensor body and the sensor connector. The sensor body comprises a base, legs and an optical assembly. The legs extend from the base to detector and emitter housings. An optical assembly has an emitter and a detector. The emitter is disposed in the emitter housing and the detector is disposed in the detector housing. The legs have an unflexed position with the emitter housing proximate the detector housing and a flexed position with the emitter housing distal the detector housing. The legs are moved to the flexed position so as to position the detector housing and emitter housing over opposite sides of a concha site. The legs are released to the unflexed position so that the concha site is grasped between the detector housing and emitter housing.

Pulse oximetry systems for measuring constituents of circulating blood can be used in many monitoring scenarios. A pulse oximetry system has an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are in the ear insert, and the patient cable transmits drive signals to these emitters from the monitor. The emitters respond to the drive signals to transmit light into the fleshy tissue. The detector generates a signal responsive to the emitted light after attenuation by pulsatile blood flow within the fingertip. The patient cable transmits the detector signal to the monitor, which processes the signal to provide a numerical readout of physiological parameters such as oxygen saturation (SpO2) and pulse rate. Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), as a few examples. In other embodiments, the device has physiological monitors and corresponding multiple wavelength optical sensors capable of measuring parameters in addition to SpO2, such as HbCO, HbMet and Hbt are described in at least U.S. patent application Ser. No. 12/056,179, filed Mar. 26, 2008, titled Multiple Wavelength Optical Sensor and U.S. patent application Ser. No. 11/366,208, filed Mar. 1, 2006, titled Noninvasive Multi-Parameter Patient Monitor, both incorporated by reference herein. Further, noninvasive blood parameter monitors and corresponding multiple wavelength optical sensors to sense SpO2, pulse rate, perfusion index (PI), signal quality (SiQ), pulse variability index (PVI), HbCO and HbMet among other parameters.

Heart pulse can be detected by measuring the dilation and constriction of tiny blood vessels in the ear canal. In one embodiment, the dilation measurement is done optically and in another embodiment, a micromechanical MEMS sensor is used. ECG sensor can be used where the electrode can detect a full and clinically valid electrocardiogram, which records the electrical activity of the heart.

One example embodiment uses the Samsung Bio-Processor which integrates multiple AFEs (Analog Front Ends) to measure diverse biometrics, including bioelectrical impedance analysis (BIA), photoplethysmogram (PPG), electrocardiogram (ECG), skin temperature and galvanic skin response (GSR) in a single chip solution. With integrated microcontroller unit (MCU), digital signal processor (DSP) and real-time clock (RTC), the Bio-Processor can monitor data in the ear with low power requirement.

Impact sensors, or accelerometers, measure in real time the force and even the number of impacts that players sustain. Data collected is sent wirelessly via Bluetooth to a dedicated monitor on the sidelines, while the impact prompts a visual light or audio alert to signal players, coaches, officials, and the training or medical staff of the team. One such sensor example is the ADXL377 from Analog Devices, a small, thin and low-power 3-axis accelerometer that measures acceleration from motion, shock, or vibration. It features a full-scale range of ±200 g, which would encompass the full range of impact acceleration in sports, which typically does not exceed 150 g's. When a post-impact individual is removed from a game and not allowed to return until cleared by a concussion-savvy healthcare professional, most will recover quickly. If the injury is undetected, however, and an athlete continues playing, concussion recovery often takes much longer. Thus, the system avoids problems from delayed or unidentified injury can include: Early dementia, Depression, Rapid brain aging, and Death. The cumulative effects of repetitive head impacts (RHI) increases the risk of long-term neuro-degenerative diseases, such as Parkinson's disease, Alzheimer's, Mild Cognitive Impairment, and ALS or Lou Gehrig's disease. The sensors' most important role is to alert to dangerous concussions. Yet, the act of real-time monitoring brings these players to the attention of their coaches not only to monitor serious impacts but, based on the data provided by the sensors, also help to modify a player's technique so that they are not, for example, keeping their head low where they can sustain injury to the front and top of the skull. In the NFL there also has been an aggressive crackdown against hits to the head and neck—a response to the ongoing concussion crisis—resulting in immediate penalty to players using their helmets as a "weapon". Customized mouthguards also have sensors therein. A customized mouthguard has tested to be 99 percent accurate in predicting serious brain injury after near-concussive force, according to an Academy of General Dentistry study. Teeth absorb and scatter infrared light, which shows how much force is taking place at the moment of impact.

The device can use optical sensors for heart rate (HR) as a biomarker in heart failure (HF) both of diagnostic and prognostic values. HR is a determinant of myocardial oxygen demand, coronary blood flow, and myocardial performance and is central to the adaptation of cardiac output to metabolic needs. Increased HR can predict adverse outcome in the general population and in patients with chronic HF. Part of the ability of HR to predict risk is related to the forces driving it, namely, neurohormonal activation. HR relates to emotional arousal and reflects both sympathetic and parasympathetic nervous system activity. When measured at rest, HR relates to autonomic activity during a relaxing condition. HR reactivity is expressed as a change from resting or baseline that results after exposure to stimuli. These stress-regulating mechanisms prepare the body for fight or flight responses, and as such can explain individual differences to psychopathology. Thus, the device monitors HR as a biomarker of both diagnostic and prognostic values.

The HR output can be used to analyze heart-rate variability (HRV) (the time differences between one beat and the next) and HRV can be used to indicate the potential health benefits of food items. Reduced HRV is associated with the development of numerous conditions for example, diabetes, cardiovascular disease, inflammation, obesity and psychiatric disorders. Aspects of diet that are viewed as undesirable, for example high intakes of saturated or trans-fat and high glycaemic carbohydrates, have been found to reduce HRV. The consistent relationship between HRV, health and morbidity allows the system to use HRV as a biomarker when considering the influence of diet on mental and physical health. Further HRV can be used as a biomarker for aging. HRV can also act as biomarkers for:

Overtraining: "Cumulative or too intensive sporting activity (e.g. competition series, overtraining syndrome), however, brings about a decrease in HRV"

Physical Fitness: "People who have an active lifestyle and maintain a good or high level of physical fitness or above-average sporting activity can achieve an increase in their basic parasympathetic activity and thus an increase in their HRV."

Overweight: "an elevated body weight or elevated free-fat mass57 correlates with a decrease in HRV. Both active and passive smoking lead to an increase in HRV"

Alcohol Abuse: "Regular chronic alcohol abuse above the alcohol quantity of a standard drink for women or two standard drinks for men reduces HRV, while moderate alcohol consumption up to these quantities does not change the HRV and is not associated with an increase"

Smoking: "Both active and passive smoking lead to an increase in HRV"

Sleep: Another important factor that affects your HRV score is the amount and quality of sleep.

In one embodiment, the system determines a dynamical marker of sino-atrial instability, termed heart rate fragmentation (HRF) and is used a dynamical biomarker of adverse cardiovascular events (CVEs). In healthy adults at rest and during sleep, the highest frequency at which the sino-atrial node (SAN) rate fluctuates varies between ~0.15 and 0.40 Hz. These oscillations, referred to as respiratory sinus arrhythmia, are due to vagally-mediated coupling between the SAN and breathing. However, not all fluctuations in heart rate (HR) at or above the respiratory frequency are attributable to vagal tone modulation. Under pathologic conditions, an increased density of reversals in HR acceleration sign, not consistent with short-term parasympathetic control, can be observed.

The system captures ECG data as biomarkers for cardiac diseases such as myocardial infarction, cardiomyopathy, atrioventricular bundle branch block, and rhythm disorders. The ECG data is cleaned up, and the system extracts features by taking quantiles of the distributions of measures on ECGs, while commonly used characterizing feature is the mean. The system applies commonly used measurement variables on ECGs without preselection and use dimension reduction methods to identify biomarkers, which is useful when the number of input variables is large and no prior information is available on which ones are more important. Three frequently used classifiers are used on all features and to dimension-reduced features by PCA. The three methods are from classical to modern: stepwise discriminant analysis (SDA), SVM, and LASSO logistic regression.

In one embodiment, four types of features are considered as input variables for classification: T wave type, time span measurements, amplitude measurements, and the slopes of waveforms for features such as (1) T Wave Type. The ECGPUWAVE function labels 6 types of T waves for each beat: Normal, Inverted, Positive Monophasic, Negative Monophasic, Biphasic Negative-Positive, and Biphasic Positive-Negative based on the T wave morphology. This is the only categorical variable considered.

(2) Time Span Measurements. Six commonly used time span measurements are considered: the length of the RR interval, PR interval, QT interval, P wave, QRS wave, and T wave.

(3) Amplitude Measurements. The amplitudes of P wave, R-peak, and T wave are used as input variables. To measure the P wave amplitude, we first estimate the baseline by taking the mean of the values in the PR segment, ST segment, and TP segment (from the end of the T wave to the start of the P wave of the next heartbeat), then subtract the maximum and minimum values of the P wave by the estimated baseline, and take the one with a bigger absolute value as the amplitude of P wave. Other amplitude measurements are obtained similarly.

(4) The Slopes of Waveforms. The slopes of waveforms are also considered to measure the dynamic features of a heartbeat. Each heartbeat is split into nine segments and the slope of the waveform in each segment is estimated by simple linear regression.

The device can include EEG sensors which measure a variety of EEG responses—alpha rhythm, ASSR, SSVEP and VEP—as well as multiple mechanical signals associated with cardiac activity, speech and breathing. EEG sensors can be used where electrodes provide low contact impedance with the skin over a prolonged period of time. A low impedance stretchable fabric is used as electrodes. The system captures various EEG paradigms: ASSR, steady-state visual evoked potential (SSVEP), transient response to visual stimulus (VEP), and alpha rhythm. The EEG sensors can predict and assess the fatigue based on the neural activity in the alpha band which is usually associated with the state of wakeful relaxation and manifests itself in the EEG oscillations in the 8-12 Hz frequency range, centered around 10 Hz. The loss of alpha rhythm is also one of the key features used by clinicians to define the onset of sleep. A mechanical transducer (electret condenser microphone) within its multimodal electro-mechanical sensor, which can be used as a reference for single-channel digital denoising of physiological signals such as jaw clenching and for removing real-world motion artifacts from ear-EEG. In one embodiment, a microphone at the tip of the earpiece facing towards the eardrum can directly capture acoustic energy traveling from the vocal chords via auditory tube to the ear canal. The output of such a microphone would be expected to provide better speech quality than the sealed microphone within the multimodal sensor.

The system can detect auditory steady-state response (ASSR) as a biomarker a type of ERP which can test the integrity of auditory pathways and the capacity of these pathways to generate synchronous activity at specific frequencies. ASSRs are elicited by temporally modulated auditory stimulation, such as a train of clicks with a fixed inter-click interval, or an amplitude modulated (AM) tone. After the onset of the stimulus, the EEG or MEG rapidly entrains to the frequency and phase of the stimulus. The ASSR is generated by activity within the auditory pathway. The ASSR for modulation frequencies up to 50 Hz is generated from the auditory cortex based on EEG. Higher frequencies of modulation (>80 Hz) are thought to originate from brainstem areas. The type of stimulus may also affect the region of activation within the auditory cortex. Amplitude modulated (AM) tones and click train stimuli are commonly used stimuli to evoke the ASSR.

The EEG sensor can be used as a brain-computer interface (BCI) and provides a direct communication pathway between the brain and the external world by translating signals from brain activities into machine codes or commands to control different types of external devices, such as a computer cursor, cellphone, home equipment or a wheelchair. SSVEP can be used in BCI due to high information transfer rate (ITR), little training and high reliability. The use of in-ear EEG acquisition makes BCI convenient, and highly efficient artifact removal techniques can be used to derive clean EEG signals.

The system can measure visually evoked potential (VEP), visually evoked response (VER) or visually evoked cortical potential (VECP). They refer to electrical potentials, initiated by brief visual stimuli, which are recorded from the scalp overlying visual cortex, VEP waveforms are extracted from the electro-encephalogram (EEG) by signal averaging. VEPs are used primarily to measure the functional integrity of the visual pathways from retina via the optic nerves to the visual cortex of the brain. VEPs better quantify functional integrity of the optic pathways than scanning techniques such as magnetic resonance imaging (MRI). Any abnormality that affects the visual pathways or visual cortex in the brain can affect the VEP. Examples are cortical blindness due to meningitis or anoxia, optic neuritis as a consequence of demyelination, optic atrophy, stroke, and compression of the optic pathways by tumors, amblyopia, and neurofibromatosis. In general, myelin plaques common in multiple sclerosis slow the speed of VEP wave peaks. Compression of the optic pathways such as from hydrocephalus or a tumor also reduces amplitude of wave peaks.

A bioimpedance (BI) sensor can be used to determine a biomarker of total body fluid content. The BIA is a noninvasive method for evaluation of body composition, easy to perform, and fast, reproducible, and economical and indicates nutritional status of patients by estimating the amount of lean body mass, fat mass, body water, and cell mass. The method also allows the assessment of patient's prognosis through the PA, which has been applied in patients with various diseases, including chronic liver disease. The phase angle varies according to the population and can be used for prognosis.

In another embodiment, the BI sensor can estimate glucose level. This is done by measuring the bioimpedance at various frequencies, where high frequency Bi is related to fluid volume of the body and low frequency BI is used to estimate the volume of extracellular fluid in the tissues.

The step of determining the amount of glucose can include comparing the measured impedance with a predetermined relationship between impedance and blood glucose level. In a particular embodiment, the step of determining the blood glucose level of a subject includes ascertaining the sum of a fraction of the magnitude of the measured impedance and a fraction of the phase of the measured impedance. The amount of blood glucose, in one embodiment, is determined according to the equation: Predicted glucose=(0.31) Magnitude+(0.24)Phase where the impedance is measured at 20 kHz. In certain embodiments, impedance is measured at a plurality of frequencies, and the method includes determining the ratio of one or more pairs of measurements and determining the amount of glucose in the body fluid includes comparing the determined ratio(s) with corresponding predetermined ratio(s), i.e., that have been previously correlated with directly measured glucose levels. In embodiments, the process includes measuring impedance at two frequencies and determining the amount of glucose further includes determining a predetermined index, the index including a ratio of first and second numbers obtained from first and second of the impedance measurements. The first and second numbers can include a component of said first and second impedance measurements, respectively. The first number can be the real part of the complex electrical impedance at the first frequency and the second number can be the magnitude of the complex electrical impedance at the second frequency. The first number can be the imaginary part of the complex electrical impedance at the first frequency and the second number can be the magnitude of the complex electrical impedance at the second frequency. The first number can be the magnitude of the complex electrical impedance at the first frequency and the second number can be the magnitude of the complex electrical impedance at the second frequency. In another embodiment, determining the amount of glucose further includes determining a predetermined index in which the index includes a difference between first and second numbers obtained from first and second of said impedance measurements. The first number can be the phase angle of the complex electrical impedance at the first frequency and said second number can be the phase angle of the complex electrical impedance at the second frequency.

The electrodes can be in operative connection with the processor programmed to determine the amount of glucose in the body fluid based upon the measured impedance. In certain embodiments, the processor wireless communicates with an insulin pump programmed to adjust the amount of insulin flow via the pump to the subject in response to the determined amount of glucose. The BIA electrodes can be spaced between about 0.2 mm and about 2 cm from each other.

In another aspect, the BI sensor provides non-invasive monitoring of glucose in a body fluid of a subject. The apparatus includes means for measuring impedance of skin tissue in response to a voltage applied thereto and a microprocessor operatively connected to the means for measuring impedance, for determining the amount of glucose in the body fluid based upon the impedance measurement(s). The means for measuring impedance of skin tissue can include a pair of spaced apart electrodes for electrically conductive contact with a skin surface. The microprocessor can be programmed to compare the measured impedance with a predetermined correlation between impedance and blood glucose level. The apparatus can include means for measuring impedance at a plurality of frequencies of the applied voltage and the program can include means for determining the ratio of one or more pairs of the impedance measurements and means for comparing the determined ratio(s) with corresponding predetermined ratio(s) to determine the amount of glucose in the body fluid.

In a particular embodiment, the apparatus includes means for calibrating the apparatus against a directly measured glucose level of a said subject. The apparatus can thus include means for inputting the value of the directly measured glucose level in conjunction with impedance measured about the same time, for use by the program to determine the blood glucose level of that subject at a later time based solely on subsequent impedance measurements.

One embodiment measures BI at 31 different frequencies logarithmically distributed in the range of 1 kHz to 1 Mhz (10 frequencies per decade). Another embodiment measures BI a t two of the frequencies: 20 and 500 kHz; and in the second set of experiments, 20 kHz only. It may be found in the future that there is a more optimal frequency or frequencies. It is quite possible, in a commercially acceptable instrument that impedance will be determined at at least two frequencies, rather than only one. For practical reasons of instrumentation, the upper frequency at which impedance is measured is likely to be about 500 kHz, but higher frequencies, even has high as 5 MHz or higher are possible and are considered to be within the scope of this invention. Relationships may be established using data obtained at one, two or more frequencies.

One embodiment, specifically for determining glucose levels of a subject, includes a 2-pole BI measurement configuration that measures impedance at multiple frequencies, preferably two well spaced apart frequencies. The instrument includes a computer which also calculates the index or indices that correlate with blood glucose levels and determines the glucose levels based on the correlation(s). an artificial neural network to perform a non-linear regression.

In another embodiment, a BI sensor can estimate sugar content in human blood based on variation of dielectric permeability of a finger placed in the electrical field of transducer. The amount of sugar in human blood can also be estimate by changing the reactance of oscillating circuits included in the secondary circuits of high-frequency generator via direct action of human upon oscillating circuits elements. With this method, the amount of sugar in blood is determined based on variation of current in the secondary circuits of high-frequency generator. In another embodiment, a spectral analysis of high-frequency radiation reflected by human body or passing through the human body is conducted. The phase shift between direct and reflected (or transmitted) waves, which characterizes the reactive component of electrical impedance, represents a parameter to be measured by this method. The concentration of substances contained in the blood (in particular, glucose concentration) is determined based on measured parameters of phase spectrum. In another embodiment, glucose concentration is determined by this device based on measurement of human body region impedance at two frequencies, determining capacitive component of impedance and converting the obtained value of capacitive component into glucose concentration in patient's blood. Another embodiment measures impedance between two electrodes at a number of frequencies and deriving the value of glucose concentration on the basis of measured values. In another embodiment, the concentration of glucose in blood is determined based mathematical model.

The microphone can also detect respiration. Breathing creates turbulence within the airways, so that the turbulent airflow can be measured using a microphone placed externally on the upper chest at the suprasternal notch. The respiratory signals recorded inside the ear canal are weak, and are affected by motion artifacts arising from a significant movement of the earpiece inside the ear canal. A control loop involving knowledge of the degree of artifacts and total output power from the microphones can be used for denoising purposes from jaw movements. Denoising can be done for EEG, ECG, PPG waveforms.

An infrared sensor unit can detect temperature detection in conjunction with an optical identification of objects allows for more reliable identification of the objects, e.g. of the eardrum. Providing the device additionally with an infrared sensor unit, especially arranged centrically at the distal tip, allows for minimizing any risk of misdiagnosis.

In one implementation information relating to characteristics of the patient's tympanic cavity can be evaluated or processed. In this case the electronics includes a camera that detects serous or mucous fluid within the tympanic cavity can be an indicator of the eardrum itself, and can be an indicator of a pathologic condition in the middle ear. Within the ear canal, only behind the eardrum, such body fluid can be identified. Thus, evidence of any body fluid can provide evidence of the eardrum itself, as well as evidence of a pathologic condition, e.g. OME.

In a method according to the preferred embodiment, preferably, an intensity of illumination provided by the at least one light source is adjusted such that light emitted by the at least one light source is arranged for at least partially transilluminating the eardrum in such a way that it can be reflected at least partially by any object or body fluid within the subject's tympanic cavity arranged behind the eardrum.

The preferred embodiment is based on the finding that translucent characteristics of the eardrum can be evaluated in order to distinguish between different objects within the ear canal, especially in order to identify the eardrum more reliably. Thereby, illumination can be adjusted such that tissue or hard bone confining the ear canal is overexposed, providing reflections (reflected radiation or light), especially reflections within a known spectrum, which can be ignored, i.e. automatically subtracted out. Such a method enables identification of the eardrum more reliably.

In particular, the degree of reddishness or reflectivity of light in the red spectral range can be determined at different illumination intensities. It can therefore be distinguished more reliably between light reflected by the eardrum itself, or by objects or fluids behind the eardrum, or by the mucosal covering the tympanic cavity wall. The reflectivity of light may be evaluated with respect to reflectivity within e.g. the green or blue spectral range. Typical spectral wavelength maxima are 450 nm (blue light), 550 nm (green light), and 600 nm (red light) for a respective (color) channel. The electronic imaging unit, e.g. comprising a color video camera, or any color sensitive sensor, may record images with respect to the red, green or blue spectral range, respectively. A logic unit may calculate, compare and normalize brightness values for each read, green and blue image, especially with respect to each separate pixel of the respective image. Such an evaluation may also facilitate medical characterization of the eardrum. In particular, the healthy eardrum is a thin, semitransparent membrane containing only few relatively small blood vessels. In contrast, an inflamed eardrum may exhibit thickening and/or increased vascularization. Also, any skin or tissue confining the ear canal as well as any mucosa in the middle ear may be heavily vascularized. In other words: The reflectivity in the different spectral ranges varies considerably between the different structures or objects as well as between healthy and inflamed tissue. Thus, referring to the spectral range enables more reliable differentiation between light reflected by the eardrum itself, or by objects or any fluid behind the eardrum, or by the tympanic cavity wall covered by mucosa.

Thereby, the risk of confounding any red (inflamed) section of the ear canal and the eardrum can be minimized. Also, the eardrum can be identified indirectly by identifying the tympanic cavity. In particular, any opaque fluid, especially amber fluid containing leukocytes and proteins, within the tympanic cavity may influence the spectrum of reflected light, depending on the intensity of illumination. At a relatively high intensity of illumination, the spectrum of reflected light will be typical for scattering in serous or mucous fluid containing particles like leukocytes, as light transmits the eardrum and is at least partially reflected by the opaque fluid. At a relatively low intensity of illumination, the spectrum of reflected light will be dominated by the eardrum itself, as a considerable fraction of the light does not transmit the eardrum, but is directly reflected by the eardrum. Thus, information relating to the tympanic cavity, especially more detailed color information, can facilitate identification of the eardrum as well as of pathologic conditions in the middle ear.

Transilluminating the eardrum can provide supplemental information with respect to the characteristics of the eardrum (e.g. the shape, especially a convexity of the eardrum), and/or with respect to the presence of any fluid within the tympanic cavity. Spectral patterns of reflected light which are typical for eardrum reflection and tympanic cavity reflection can be use to determine the area of interest as well as a physiologic or pathologic condition of the eardrum and the tympanic cavity, especially in conjunction with feedback controlled illumination.

Any fluid within the tympanic cavity evokes a higher degree of reflection than the physiologically present air. The fluid increases reflectance. In contrast, in case the tympanic cavity is filled with air, any light transilluminating the eardrum is only reflected with inferior intensity, as most of the light is absorbed within the tympanic cavity. In other words: transilluminating the eardrum and evaluating reflected light in dependence on the intensity of illumination can facilitate determining specific characteristics of the eardrum, e.g. an absolute degree of reflectivity in dependence on different wavelengths and intensities, providing more information or more certain information with respect to the type of tissue and its condition. Evaluating reflected light can comprise spectral analysis of translucent reflection, especially at different illumination intensities.

The degree of reflection in the red spectrum from the area of the eardrum may depend on the illumination level, i.e. the intensity of illumination. In particular, the red channel reflection can increase with increasing intensity of illumination. The higher the intensity of illumination, the higher the red channel reflection intensity. Also, it has been found that at relatively high intensities of illumination, not only the eardrum, but also any other tissue will reflect more light in the red spectrum. Therefore, on the one hand, providing a control or logic unit which is arranged for adjusting the intensity of illumination can facilitate identification of the eardrum. On the other hand, it can facilitate determining specific characteristics of the eardrum, e.g. an absolute degree of red channel reflection, such that the red channel reflection provides more information or more certain information with respect to the type of tissue and state of the tissue.

The degree of red channel reflection does not increase in the same manner with increasing intensity of illumination, depending on the presence of body fluid behind the eardrum. It has been found that in case there is body fluid within the tympanic cavity, with increasing intensity of illumination, the degree of red channel reflection does not increase as strongly as if the tympanic cavity was empty. Thus, based on the (absolute) degree of red channel reflection, the presence of fluid behind the eardrum can be evaluated. This may facilitate determination of pathologic conditions, e.g. OME.

The camera and process can identify pattern recognition of geometrical patterns, especially circular or ellipsoid shapes, or geometrical patterns characterizing the malleus bone, or further anatomical characteristics of the outer ear or the middle ear. Pattern recognition allows for more reliable identification of the eardrum. Pattern recognition can comprise recognition based on features and shapes such as the shape of e.g. the malleus, the malleus handle, the eardrum or specific portions of the eardrum such as the pasr flaccida or the fibrocartilagenous ring. In particular, pattern recognition may comprise edge detection and/or spectral analysis, especially shape detection of a circular or ellipsoid shape with an angular interruption at the malleus bone or pars flaccida.

In a method according to the preferred embodiment, preferably, the method further comprises calibrating a spectral sensitivity of the electronic imaging unit and/or calibrating color and/or brightness of the at least one light source. Calibration allows for more reliable identification of objects. It has been found that in case the light intensity is very high allowing for passing light through a healthy eardrum, which is semitransparent, a considerable amount of light within the red spectrum can be reflected by the tympanic cavity (especially due to illumination of red mucosa confining the middle ear). Thus, calibrating brightness or the intensity of emitted light enables more accurate evaluation of the (absolute) degree of red channel reflection and its source. In other words, spectral calibration of the imaging sensor in combination with spectral calibration of the illumination means allows for the evaluation of the tissue types and conditions.

Calibration can be carried out e.g. based on feedback illumination control with respect to different objects or different kinds of tissue, once the respective object or tissue has been identified. Thereby, spectral norm curves with respect to different light intensities provide further data based on which calibration can be carried out.

Figure 3D:
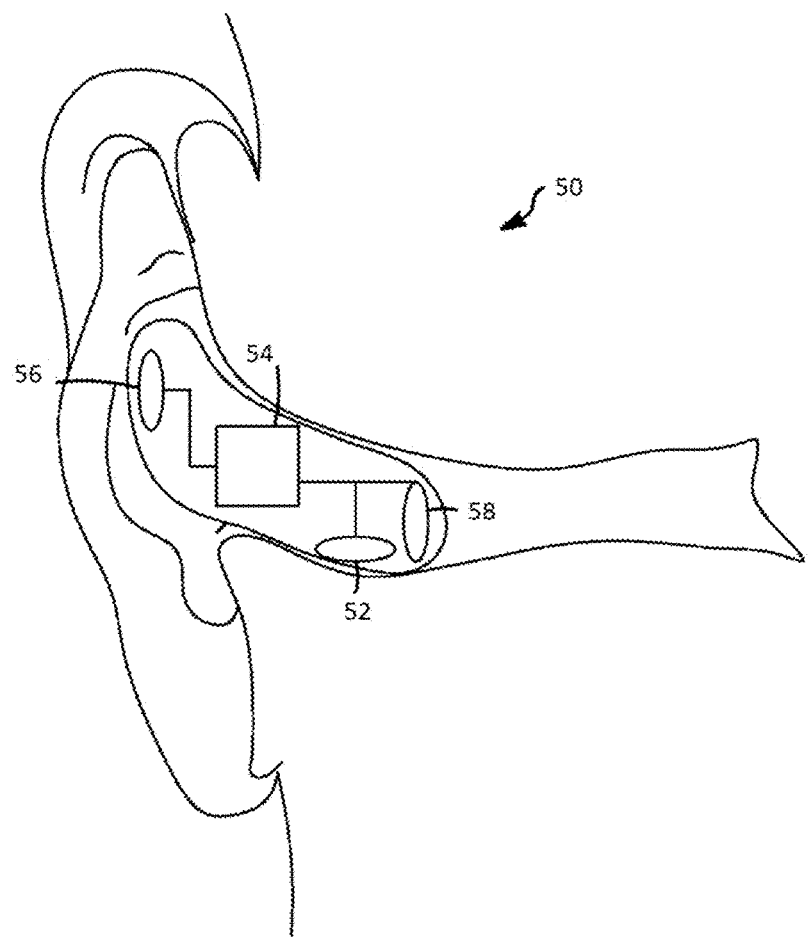
FIG. 3D shows another custom hearing aid and monitoring device.

FIG. 3D shows an earpiece 50 that has one or more sensors 52, a processor 54, a microphone 56, and a speaker 58. The earpiece 50 may be shaped and sized for an ear canal of a subject. The transducer 52 may be any of the previously discussed sensors (EEG, ECG, camera, temperature, pressure, among others). In general, the sensor 52 may be positioned within the earpiece at a position that, when the earpiece 50 is placed for use in the ear canal, corresponds to a location on a surface of the ear canal that exhibits a substantial shape change correlated to a musculoskeletal movement of the subject. The position depicted in FIG. 3B is provided by way of example only, and it will be understood that any position exhibiting substantial displacement may be used to position the sensor(s) 52 for use as contemplated herein. In one aspect, the sensor 52 may be positioned at a position that, when the earpiece is placed for use in the ear canal, corresponds to a location on a surface of the ear canal that exhibits a maximum surface displacement from a neutral position in response to the musculoskeletal movement of the subject. In another aspect, the transducer 52 may be positioned at a position that, when the earpiece is placed for use in the ear canal, corresponds to a location on a surface of the ear canal that exceeds an average surface displacement from a neutral position in response to the musculoskeletal movement of the subject. It will be understood that, while a single transducer 52 is depicted, a number of transducers may be included, which may detect different musculoskeletal movements, or may be coordinated to more accurately detect a single musculoskeletal movement.

The processor 54 may be coupled to the microphone 56, speaker 58, and sensor(s) 52, and may be configured to detect the musculoskeletal movement of the subject based upon a pressure change signal from the transducer 52, and to generate a predetermined control signal in response to the musculoskeletal movement. The predetermined control signal may, for example, be a mute signal for the earpiece, a volume change signal for the earpiece, or, where the earpiece is an earbud for an audio player (in which case the microphone 56 may optionally be omitted), a track change signal for the audio player coupled to the earpiece.

Power for the unit can be from a battery or scavenged from the environment using solar or temperature differential power generation. In one embodiment, a biological battery can be tapped. Located in the part of the ear called the cochlea, the battery chamber is divided by a membrane, some of whose cells are specialized to pump ions. An imbalance of potassium and sodium ions on opposite sides of the membrane, together with the particular arrangement of the pumps, creates an electrical voltage. A storage device receives charge that gradually builds up charge in a capacitor. The voltage of the biological battery fluctuates, for example one circuit needs between 40 seconds and four minutes to amass enough charge to power a radio. The frequency of the signal was thus itself an indication of the electrochemical properties of the inner ear.

FIG. 4A shows a deployed device 30 that is plugged into a sound cable. The device has an outer face 32 that includes a microphone or microphone array and energy scavenger on one side. The other side is an output port 34 that is snugged fitted to the ear canal using a custom ear insert such as that of FIG. 2A-2B.

FIG. 4B shows in more detail the device 30 having an outer face 32 that can include microphone or microphone array. Further, the device can harvest energy with solar cells on the face 32. The unit can optionally connect to a remote microphone, camera, cellular transceiver, and/or battery via cable 34. The cable or output port 34 can be connected to a behind-the-ear clip-on housing, for example. The device 30 has a custom form protrusion or extension 36 that is custom to the wearer's ear structures. The extension 36 can include hearing aid electronics and/or body sensors as detailed above. The sensors can help detect ear issues such as:

Chronic disease. Some cases of hearing loss are not caused by a problem with the ear, but by an interruption of blood flow to the ear or brain. Strokes, heart disease, high blood pressure, diabetes, and rheumatoid arthritis can all cause mild to moderate hearing loss.

Meniere's disease. If the user is experiencing extreme dizziness, loss of balance, and nausea, a hearing screening could lead to a diagnosis of Meniere's disease. This condition is caused by an imbalance of fluids in the inner ear, causing a ringing in the ears (tinnitus), a blocked feeling or hearing loss in one or both ears, and severe vertigo.

Paget's disease. This bone disorder may have no early symptoms, and cause lifelong injuries and medical conditions in the patient. As time goes on, patients with Paget's disease may suffer hearing loss and chronic headaches, as well as nerve, bone, and joint pain. In severe cases, patients may have abnormally large head sizes, improper spine curvature, or severe bowing of the arms and legs.

Pendred syndrome. Pendred syndrome is a genetic condition that causes hearing loss, thyroid dysfunction, and balance problems in children. A child who is born with Pendred syndrome is likely to lose hearing function early in life, in some cases before the child reaches three years old. Hearing loss caused by Pendred syndrome will usually worsen over time, and can lead to total deafness.

Otosclerosis. This disease causes the bones in the middle ear to harden, preventing them from conducting sound into the inner ear. Otosclerosis can often be treated or even reversed with surgery.

In one particular variation for treating tinnitus, device may utilize an audio signal, such as music and in particular music having a dynamic signal with intensities varying over time with multiple peaks and troughs throughout the signal. Other audio signals such as various sounds of nature, e.g., rainfall, wind, waves, etc., or other signals such as voice or speech may alternatively be used so long as the audio signal is dynamic. This audio signal may be modified according to a masking algorithm and applied through the device 14 and to the patient to partially mask the patient's tinnitus. An example of how an audio signal may be modified is described in detail in U.S. Pat. No. 6,682,472 (Davis), which is incorporated herein by reference in its entirety and describes a tinnitus treatment which utilizes software to spectrally modify the audio signal in accordance with a predetermined masking algorithm which modifies the intensity of the audio signal at selected frequencies. The described predetermined masking algorithm provides intermittent masking of the tinnitus where the tinnitus is completely masked during peaks in the audio signal and where the perceived tinnitus is detectable to the patient during troughs in the audio signal. Such an algorithm provides for training and habituation by the patient of their tinnitus. Accordingly, the intensity of the audio signal may be modified across the spectrum of the signal and may also be modified to account for any hearing loss that the patient may have incurred. The audio signal having a dynamic spectrum with varying intensities. The audio signal may completely mask the patient's tinnitus during peaks in the signal while during troughs in the audio signal, the tinnitus may be perceived by the patient. Moreover, the masking algorithm may be modified to account for any hearing loss of the patient.

FIGS. 5A-5B show an AR version where the earpiece 30 includes a 5G transceiver in the unit 30 that is connected to antenna, mike and camera in an extension 39, which in turn projects from the outer face 32. The extension 39 is semi-rigid and can be adjusted by the user to aim at predetermined areas. In one embodiment, a plurality of extensions 39 extend like whiskers or hairs that provides signal reception but hard to see. In other embodiments, a single extension 39 includes antenna(s) wrapped on the outside of the extension while images can be captured and transmitted over fiber optics to a high resolution imager. Sound vibration can also be optically captured where incident sound waves modulate the light guided in optical fibers without the help of electricity. Intensity modulation by beam deflection at a moving membrane. For example, an optical mike from PKI can be used.

To supplement the whisker antenna, the front and edge of the earpiece 30 has 3D printed MIMO antennas for Wifi, Bluetooth, and 5G signals. The extension 39 further includes a microphone and camera at the tip to capture audio visual information to aid the user as an augmented reality system. The earpiece contains an inertial measurement unit (IMU) coupled to the intelligent earpiece. The IMU is configured to detect inertial measurement data that corresponds to a positioning, velocity, or acceleration of the intelligent earpiece. The earpiece also contains a global positioning system (GPS) unit coupled to the earpiece that is configured to detect location data corresponding to a location of the intelligent earpiece. At least one camera is coupled to the intelligent earpiece and is configured to detect image data corresponding to a surrounding environment of the intelligent guidance device.

In one embodiment, the earpiece 30 is a standalone 5G phone controlled by a machine computer interface through the EEG sensor as detailed above. In another variation, voice command can be issued to the 5G phone. In another variation, a foldable display is provided with a larger battery and 5G transceiver. When the user opens the foldable display, the data processing including deep learning operations, 5G transceiver communication, IMU and GPS operations are automatically transferred to the foldable display to conserve power.

The earpiece for providing social and environmental awareness can continuously observe the user and his surroundings as well as store preference information, such as calendars and schedules, and access remote databases. Based on this observed data, the earpiece can proactively provide feedback to the user. Proactive functions can, for example, remind a user where he should be, inform the user of the name of a person he is speaking with, warn the user when the user may be approaching a hazardous situation, etc. This is advantageous over the state of the art because the user of the earpiece can be provided information without having to request it. This can result in the user being provided feedback that he may not have known he could receive. Additionally, it allows the user to receive feedback without wasting extra time or effort. In some circumstances, this proactive feedback can prevent potential embarrassment for the user (for example, he need not ask the earpiece the name of a person he is speaking with). When left and right earpieces are deployed, the stereo microphones and cameras of the system provide depth and distance information to the device. The device can then use this information to better determine social and environmental elements around the user. The combination of the global positioning system (GPS), the inertial measurement unit (IMU) and the camera is advantageous as the combination can provide more accurate feedback to the user. In one embodiment, the earpiece relies on the GPS and IMU and 5G streams from a smart phone to minimize size and power consumption. The earpiece can use smart phone memory to store object data regarding previously determined objects. The memory also stores previously determined user data associated with the user. The earpiece also includes a processor connected to the IMU, the GPS unit and the at least one camera. The processor is configured to recognize an object in the surrounding environment. This is done by analyzing the image data based on the stored object data and at least one of the inertial measurement data or the location data. The processor is also configured to determine a desirable event or action based on the recognized object, the previously determined user data, and a current time or day. The processor is also configured to determine a destination based on the determined desirable event or action. The processor is also configured to determine a navigation path for navigating the intelligent guidance device to the destination. This is determined based on the determined destination, the image data, and at least one of the inertial measurement data or the location data. The processor is also configured to determine output data based on the determined navigation path. A speaker is included that is configured to provide audio information to the user based on at least one of the recognized object, determined desirable event or action, or navigation path. The AR system provides continuous social and environmental awareness by the earpiece. The method includes detecting, via an inertial measurement unit (IMU), a global position system unit (GPS) or a camera, inertial measurement data corresponding to a positioning, velocity, or acceleration of the earpiece. Location data corresponding to a location of the earpiece or image data corresponding to a surrounding environment of the earpiece is also determined. The method also includes storing, in a memory, object data regarding previously determined objects and previously determined user data regarding the user. The method also includes recognizing, by a processor, an object in the surrounding environment by analyzing the image data based on the stored object data and at least one of the inertial measurement data or the location data. The method further includes determining, by the processor, a desirable event or action based on the recognized object, the previously determined user data, and a current time or day. The processor also determines a destination based on the determined desirable event or action. The processor may determine a navigation path for navigating the intelligent guidance device to the destination based on the determined destination, the image data, and at least one of the inertial measurement data or the location data. The processor may determine output data based on the determined navigation path. The method further includes providing, via a speaker or a vibration unit, audio or haptic information to the user based on at least one of the recognized object, the determined desirable event or action, or the navigation path. In one embodiment, the earpiece of FIGS. 5A-5B also includes an antenna configured to transmit the image data, the inertial measurement data, the location data and the object data to a remote processor and to receive processed data from the remote processor (such as a 5G smart phone or a remote server array, among others). The remote processor is configured to recognize an object in the surrounding environment by analyzing the image data based on the stored object data and at least one of the inertial measurement data or the location data. The remote processor is also configured to determine a desirable event or action based on the recognized object, the previously determined user data, and a current time or day. The remote processor is also configured to determine a destination based on the determined desirable event or action. The remote processor is also configured to determine a navigation path for navigating the intelligent guidance device to the destination based on the determined destination, the image data, and at least one of the inertial measurement data or the location data. The remote processor is further configured to determine output data based on the determined navigation path. The earpiece also includes a speaker configured to provide audio information to the user based on at least one of the recognized object, determined desirable event or action, or navigation path. For example, the user may give a voice command, "Take me to building X in Y campus." The earpiece may instruct the smart phone download a relevant map if not already stored, or may navigate based on perceived images from the stereo cameras. As the user follows the navigation commands from the earpiece 30, the user may walk by a coffee shop in the morning, and the earpiece 100 would recognize the coffee shop and the time of day, along with the user's habits, and appropriately alert the user. The earpiece 30 may verbally alert the user through the speaker. The user may use an input device or a web page to adjust settings, which for example may control the types of alerts, what details to announce, and other parameters which may relate to object recognition or alert settings. The user may turn on or off certain features as needed. When navigating indoors, the GPS may not provide enough information to a blind user to navigate around obstacles and reach desired locations or features. The earpiece cameras may recognize, for instance, stairs, exits, and restrooms and appropriately match the images with the GPS mapping system to provide better guidance.

The earpiece 30 can respond to a request which may be, for example, a request to identify a person, identify a room, identify an object, identify any other place, navigate to a certain location such as an address or a particular room in a building, to remind the user of his current action, what color an object is, if an outfit matches, where another person is pointing or looking. For other example, when the detected data suggests that the user requires an opinion of another person, a communication channel may be established with a device of another person. For example, when the detected speech regarding an outfit of the user, facial recognition data regarding the user being indecisive or wondering about what to wear, and/or perceived action of a user in front of a mirror indicate that the user needs fashion advice from another person, a video teleconference between the user and a friend of the user may be established. From prior conversations/interactions, the earpiece may have previously stored a user's friend's contact information. The processor may categorize types of friends of the user and recognize that this communication needs to be with a friend that the user is comfortable with. The processor may output data to the user letting the user know that a video conference or teleconference will be established with the friend. The earpiece 30 may provide a video connection to a friend of the user or send a picture of the outfit to a friend of the user. In this example, the friend may provide a response as to whether or not the outfit matches. The friend may also assist the user in finding an alternate outfit that matches.

In order to program a hearing aid to be tailored to the user's hearing needs, the user's hearing threshold may be measured using a sound-stimulus-producing device and calibrated headphone. The measurement of the hearing threshold may take place in a sound-isolating room. For example, the measurement may occur in a room where there is very little audible noise. The sound-stimulus-producing device and the calibrated headphones may be referred to as an audiometer.

Figure 6:
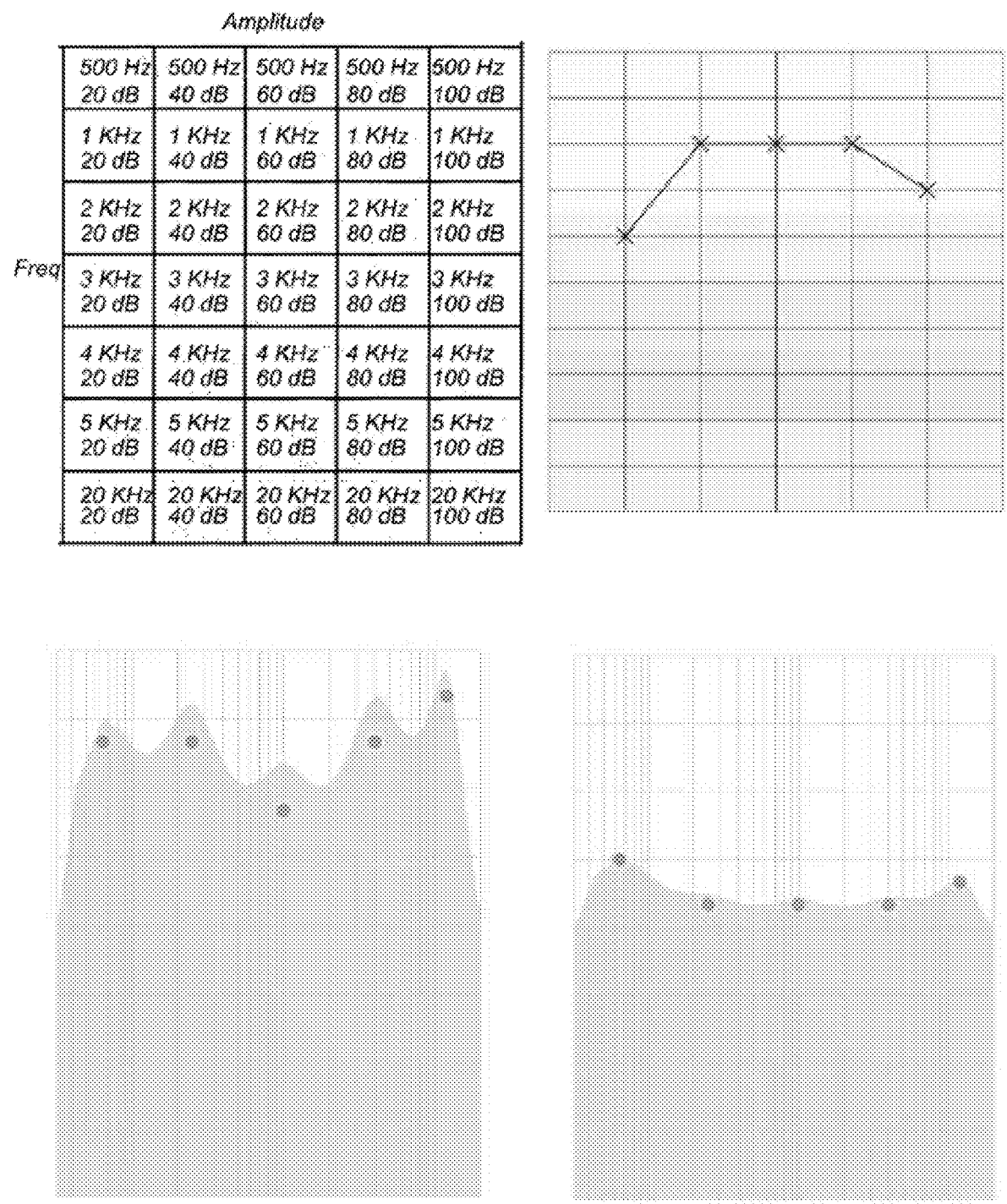
FIG. 6 shows exemplary audiogram test flow and user interface designs.

As shown in FIG. 6, the audiometer may generate pure tones at various frequencies between 125 Hz and 12,000 Hz that are representative of the frequency bands in which the tones are included. These tones may be transmitted through the headphones of the audiometer to the individual being tested. The intensity or volume of the pure tones is varied until the individual can just barely detect the presence of the tone. For each pure tone, the intensity of the tone at which the individual can just barely detect the presence of the tone is known as the individual's air conduction threshold of hearing. The collection of the thresholds of hearing at each of the various pure tone frequencies is known as an audiogram and may be presented in graphical form.

After audio equipment calibration, each frequency will be tested separately, at increasing levels. In one embodiment, the system starts with the lowest amplitude (quietest file at −5 dbHL for example) and stop when a user hearing threshold level has been reached. Files labelled 70 dBHL and above, are meant to detect severe hearing losses, and will play very loud for a normal hearing person. The equipment captures responses used to generate an audiogram which is a graph that shows the softest sounds a person can hear at different frequencies. It plots the threshold of hearing relative to an average 'normal' hearing. In this test, the ISO 389-7:2005 standard is used. Levels are expressed in deciBels Hearing Level (dBHL). The system saves the measurements and corresponding plots of Audiogram, Distortion, Time Analysis, Spectrogram, Audibility Spectrogram, 2-cc Curve, Occlusion Effects, and Feedback Analysis. A hearing aid prescription based on a selected fitting prescription formula/rational can be filled. The selected hearing aid can be adjusted and results analyzed and plotted with or without the involvement of the hearing-impaired individual. The system can optimize, objectively and subjectively, the performance of a selected hearing aid according to measured in-the-ear-canal probe response as a function of the selected signal model, hearing aid parameter set, the individual's measured hearing profile, and subjective responses to the presented audible signal. The system can determine the characteristics of a simulated monaural or binaural hearing aid system that produces natural sound perception and improved sound localization ability to the hearing impaired individual. This is accomplished by selecting a simulated hearing aid transfer function that produces, in conjunction with the face-plate transfer function, a combined transfer function that matches that of the unaided transfer function for each ear. The matching requirement typically involves frequency and phase responses. However, the magnitude response is expected to vary because most hearing impaired individuals require amplification to compensate for their hearing losses.

Based on the audiogram, amplifier parameters can be adjusted to improve hearing. In one embodiment for obtaining hearing enhancement fittings for a hearing aid device is described. In one embodiment, a plurality of audiograms is divided into one or more sets of audiograms. A representative audiogram is created for each set of audiograms. A hearing enhancement fitting is computed from each representative audiogram. A hearing aid device is programmed with one or more hearing enhancement fittings computed from each representative audiogram. In one embodiment, the one or more sets of audiograms may be subdivided into one or more subsets until a termination condition is satisfied. In one configuration, one or more audiograms may be filtered from the plurality of audiograms. For example, one or more audiograms may be filtered from the plurality of audiograms that exceed a specified fitting range for the hearing aid device. In one embodiment, a mean hearing threshold may be determined at each measured frequency of each audiogram within the plurality of audiograms. Prototype audiograms may be created from the mean hearing threshold. In addition, each prototype audiogram may be associated with a set of audiograms. In one configuration, an audiogram may be placed in the set of audiograms if the audiogram is similar to the prototype audiogram associated with the set. In one embodiment, the creation of a representative audiogram for each set of audiograms may include calculating a mean of each audiogram in a set of audiograms. When the threshold of hearing in each frequency band has been determined, this threshold may be used to estimate the amount of amplification, compression, and/or other adjustment that will be employed in the hearing aid device to compensate for the individual's loss of hearing. In the example of FIG. 6, the system will start at 500 Hz with progressing loudness before going to the next row at 1 kHz, 2, 3, 4, 5 and 20 kHz, respectively.

In one aspect, a method includes providing an in-ear device to a user anatomy; determine an audio response chart for a user based on a plurality of environments (restaurant, office, home, theater, party, concert, among others), determining a current environment, and updating the hearing aid parameters to optimize the amplifier response to the specific environment. The environment can be auto detected based on GPS position data or external data such as calendaring data or can be user selected using voice command, for example. In another embodiment, a learning machine automatically selects an optimal set of hearing aid parameters based on ambient sound and other confirmatory data.

In the example of FIG. 6, the system will start at 500 Hz with progressing loudness before going to the next row at 1 kHz, 2, 3, 4, 5 and 20 kHz, respectively, and then repeats the test in different ambient environments such as restaurant, office, home, theater, party, concert, among others and records the best audio responses in view of the "noise". This is how the learning machine or neural network learns the optimum settings based on the specific setting. Moreover, as the user operates the device, the learning system improves its performance. The user can train the device to provide optimal variable processing factors for different listening criteria, such as to maximize speech intelligibility, listening comfort, or pleasantness.

In one embodiment, based on the detected environment, the learning machine can adjust amplification and gain control. It can optimize the gain at each or every frequency of the amplifier in a particular acoustic environment. The variable processing factor is can be the amplifier gain at each or every frequency. For example, gain at each or every frequency of the amplifier can be a function of sound pressure level at the microphone in band i; SNRi=signal to noise ratio in band i; and SNRav=average SNR in all bands. Other acoustic or psychoacoustic parameters, such as higher-order moments of the spectrum of the signal and variations of these moments with time, or other statistical parameters or estimates of the acoustic signal or combinations of these parameters, and optionally with other additional coefficients, can be used to calculate the gain or processing factors other than gain, such as the speed at which the device reacts to change in the acoustic environment. In another example, the learning machine can adjust parameters based on the environment by: (i) the volume of the output signal; (ii) the gain of the output signal at particular frequencies relative to other frequencies, for example the mid frequency gain can be boosted or attenuated with respect to the low or high band frequencies of the output signal; and (iii) a slope control where the low and high frequency band gains are adjusted in opposing directions while the mid band gain is unchanged. In one embodiment, the learning machine can detect and adjust acoustic environment or psychoacoustic parameters that are highly correlated to a particular listening criterion, such as maximizing speech intelligibility or listening comfort. The variable processing factors may automatically adapt for the predicted weighted combination of listening criteria as determined by the values of the coefficients and the acoustic environment and/or psychoacoustic parameters used by the learning system. The system further eventually allows the user to 'train' the device to adjust its operation automatically. This has a number of advantages including: (1) greater levels of user satisfaction for both hearing aids and, because of the better control users have over their hearing; (2) improved listening comfort, and/or speech intelligibility and/or subjective sound quality, because processing parameters are optimized by each user to the personal preference and needs of each user; (3) the ability to generalize the 'training' algorithm to work effectively with future devices that have different, or additional, parameters that require adjustment; (4) because the training is carried out by the user in daily life, expensive clinical time is not required to achieve adjustment of the hearing aid and as adjustment is carried out in real life conditions, the adjustment better relates to actual performance of the device, rather than ideal clinical conditions; and (5) The ability to generalize the training algorithm to work effectively in environments for which no training has been provided by the user, by automatically applying the general relationships between preferred variable processing factors and acoustic characteristics that have been established by the training.

FIG. 7A shows an exemplary learning machine such as a n artificial neural network (ANN) that can be trained on optimizing hearing assistance for the user. The ANN or connectionist systems are computing systems vaguely inspired by the biological neural networks that constitute animal brains. Such systems "learn" to perform tasks by considering examples, generally without being programmed with any task-specific rules. An ANN is based on a collection of connected units or nodes called artificial neurons, which loosely model the neurons in a biological brain. Each connection, like the synapses in a biological brain, can transmit a signal from one artificial neuron to another. An artificial neuron that receives a signal can process it and then signal additional artificial neurons connected to it. Neural networks come in many shapes and sizes and with varying degrees of complexity. Deep neural networks are defined as having at least two "hidden" processing layers, which are not directly connected to a system's input or output. Each hidden layer refines the results fed to it by previous layers, adding in new considerations based on prior knowledge.

In one embodiment, machine learning is used for segregating sounds. A digital filter that not only amplifies sound but can also isolate speech from background noise and automatically adjust the volumes of each separately. The system extract features that could distinguish voices from noise based on common changes in amplitude, frequency, and the modulations of each. For example, the features can cover frequencies of the sounds and their intensities (loud or soft). The deep neural network uses the features during an unsupervised training to distinguish speech from noise and adjusts the amplifier control settings. During operation and based on user responses under supervised training, the neural network learns from its success and failures and improves on the amplifier settings. This iteratively learning of noise in different environments enables users to understand spoken words obscured by noise. Because it's not necessary for listeners to understand every word in a phrase to gather its meaning, this improvement frequently meant the difference between comprehending a sentence or not.

The deep learning network can also be used to identify user health. In embodiments that measure user health with heart rate, BI, ECG, EEG, temperature, or other health parameters, if an outlier situation exists, the system can flag to the user to follow up as an unusual sustained variation from normal health parameters. While this approach may not identify exact causes of the variation, the user can seek help early. FIG. 7B shows an exemplary analysis with normal targets and outliers as warning labels. For example, a patient may be mostly healthy, but when he or she is sick, the information pops out as outliers from the usual data. Such outliers can be used to scrutinize and predict patient health. The data can be population based, namely that if a population spatially or temporally has the same symptoms, and upon checking with the medical hospitals or doctors to confirm the prediction, public health warnings can be generated. There are two main kinds of machine learning techniques: Supervised learning: in this approach, a training data sample with known relationships between variables is submitted iteratively to the learning algorithm until quantitative evidence ("error convergence") indicates that it was able to find a solution which minimizes classification error. Several types of artificial neural networks work according to this principle; and Unsupervised learning: in this approach, the data sample is analyzed according to some statistical technique, such as multivariate regression analysis, principal components analysis, cluster analysis, etc., and automatic classification of the data objects into subclasses might be achieved, without the need for a training data set.

Medical prognosis can be used to predict the future evolution of disease on the basis of data extracted from known cases such as the prediction of mortality of patients admitted to the Intensive Care Unit, using physiological and pathological variables collected at admission. Medical diagnosis can be done, where ML is used to learn the relationship between several input variables (such as signs, symptoms, patient history, lab tests, images, etc.) and several output variables (the diagnosis categories). An example from my research: using symptoms related by patients with psychosis, an automatic classification system was devised to propose diagnoses of a particular disease. Medical therapeutic decisions can be done where ML is used to propose different therapies or patient management strategies, drugs, etc., for a given health condition or diagnosis. Example from my research: patients with different types of brain hematomas (internal bleeding) were used to train a neural network so that a precise indication for surgery was given after having learned the relationships between several input variables and the outcome. Signal or image analysis can be done, where ML is used to learn how features extracted from physiological signals (such as an EKG) or images (such as an x-ray, tomography, etc.) are associated to some diagnoses. ML can even be used to extract features from signals or images, for example, in the so-called "signal segmentation". Example from my research: non-supervised algorithms were used to extract different image textures from brain MRIs (magnetic resonance imaging), such as bone, meninges, white matter, gray matter, vases, ventricles, etc., and then classifying automatically unknown images, painting each identified region with a different color. In another example large data sets containing multiple variables obtained from individuals in a given population (e.g., those living in a community, or who have a given health care plan, hospital, etc.), are used to train ML algorithms, so as to discover risk associations and predictions (for instance, what patients have a higher risk of emergency risk readmissions or complications from diabetes. Public health can apply ML to predict, for instance, when and where epidemics are going to happen in the future, such as food poisoning, infectious diseases, bouts of environmental diseases, and so on.

FIG. 7C shows an exemplary system to collect lifestyle and genetic data from various populations for subsequent prediction and recommendation to similarly situated users. The system collects attributes associated with individuals that co-occur (i.e., co-associate, co-aggregate) with attributes of interest, such as specific disorders, behaviors and traits. The system can identify combinations of attributes that predispose individuals toward having or developing specific disorders, behaviors and traits of interest, determining the level of predisposition of an individual towards such attributes, and revealing which attribute associations can be added or eliminated to effectively modify his or her lifestyle to avoid medical complications. Details captured can be used for improving individualized diagnoses, choosing the most effective therapeutic regimens, making beneficial lifestyle changes that prevent disease and promote health, and reducing associated health care expenditures. It is also desirable to determine those combinations of attributes that promote certain behaviors and traits such as success in sports, music, school, leadership, career and relationships. For example, the system captures information on epigenetic modifications that may be altered due to environmental conditions, life experiences and aging. Along with a collection of diverse nongenetic attributes including physical, behavioral, situational and historical attributes, the system can predict a predisposition of a user toward developing a specific attribute of interest. In addition to genetic and epigenetic attributes, which can be referred to collectively as pangenetic attributes, numerous other attributes likely influence the development of traits and disorders. These other attributes, which can be referred to collectively as non-pangenetic attributes, can be categorized individually as physical, behavioral, or situational attributes.

FIG. 7C displays one embodiment of the attribute categories and their interrelationships according to the one embodiment and illustrates that physical and behavioral attributes can be collectively equivalent to the broadest classical definition of phenotype, while situational attributes can be equivalent to those typically classified as environmental. In one embodiment, historical attributes can be viewed as a separate category containing a mixture of genetic, epigenetic, physical, behavioral and situational attributes that occurred in the past. Alternatively, historical attributes can be integrated within the genetic, epigenetic, physical, behavioral and situational categories provided they are made readily distinguishable from those attributes that describe the individual's current state. In one embodiment, the historical nature of an attribute is accounted for via a time stamp or other time-based marker associated with the attribute. As such, there are no explicit historical attributes, but through use of time stamping, the time associated with the attribute can be used to make a determination as to whether the attribute is occurring in what would be considered the present, or if it has occurred in the past. Traditional demographic factors are typically a small subset of attributes derived from the phenotype and environmental categories and can be therefore represented within the physical, behavioral and situational categories.

Since the system captures information from various diverse populations, the data can be mined to discover combinations of attributes regardless of number or type, in a population of any size, that cause predisposition to an attribute of interest. The ability to accurately detect predisposing attribute combinations naturally benefits from being supplied with datasets representing large numbers of individuals and having a large number and variety of attributes for each. Nevertheless, the one embodiment will function properly with a minimal number of individuals and attributes. One embodiment of the one embodiment can be used to detect not only attributes that have a direct (causal) effect on an attribute of interest, but also those attributes that do not have a direct effect such as instrumental variables (i.e., correlative attributes), which are attributes that correlate with and can be used to predict predisposition for the attribute of interest but are not causal. For simplicity of terminology, both types of attributes are referred to herein as predisposing attributes, or simply attributes, that contribute toward predisposition toward the attribute of interest, regardless of whether the contribution or correlation is direct or indirect.

FIG. 7D shows a deep learning machine using deep convolutionary neural networks for detecting genetic based drug-drug interaction. One embodiment uses an AlexNet: 8-layer architecture, while another embodiment uses a VGGNet: 16-layer architecture (each pooling layer and last 2 FC layers are applied as feature vector). In one embodiment for drugs, the indications of use and other drugs used capture most of many important covariates. One embodiment access data from SIDER (a text-mined database of drug package inserts), the Offsides database that contains information complementary to that found in SIDER and improves the prediction of protein targets and drug indications, and the Twosides database of mined putative DDIs also lists predicted adverse events, all available at the http://PharmGKB.org Web site.

The system of FIG. 7D receives data on adverse events strongly associated with indications for which the indication and the adverse event have a known causative relationship. A drug-event association is synthetic if it has a tight reporting correlation with the indication ($p \geq 0.1$) and a high relative reporting (RR) association score ($RR \geq 2$). Drugs reported frequently with these indications were 80.0 (95% CI, 14.2 to 3132.8; $P<0.0001$, Fisher's exact test) times as likely to have synthetic associations with indication events. Disease indications are a significant source of synthetic associations. The more disproportionately a drug is reported with an indication (x axis), the more likely that drug will be synthetically associated. For example, adverse events strongly associated with drugs are retrieved from the drug's package insert. These drug-event pairs represent a set of known strong positive associations. Adverse events related to sex and race are also analyzed. For example, for physiological reasons, certain events predominantly occur in males (for example, penile swelling and azoospermia). Drugs that are disproportionately reported as causing adverse events in males were more likely to be synthetically associated with these events. Similarly, adverse events that predominantly occur in either relatively young or relatively old patients are analyzed.

"Off-label" adverse event data is also analyzed, and off-label uses refer to any drug effect not already listed on the drug's package insert. For example, the SIDER database, extracted from drug package inserts, lists 48,577 drug-event associations for 620 drugs and 1092 adverse events that are also covered by the data mining. Offsides recovers 38.8% (18,842 drug-event associations) of SIDER associations from the adverse event reports. Thus, Offsides finds different associations from those reported during clinical trials before drug approval.

Polypharmacy side effects for pairs of drugs (Twosides) are also analyzed. These associations are limited to only those that cannot be clearly attributed to either drug alone (that is, those associations covered in Offsides). The database contains a significant association for which the drug pair has a higher side-effect association score, determined using the proportional reporting ratio (PRR), than those of the individual drugs alone. The system determines pairwise similarity metrics between all drugs in the Offsides and SIDER databases. The system can predict shared protein targets using drug-effect similarities. The side-effect similarity score between two drugs is linearly related to the number of targets that those drugs share.

The system can determine relationships between the proportion of shared indications between a pair of drugs and the similarity of their side-effect profiles in Offsides. The system can use side-effect profiles to suggest new uses for old drugs. While the preferred system predicts existing therapeutic indications of known drugs, the system can recommend drug repurposing using drug-effect similarities in Offsides. Corroboration of class-wide interaction effects with EMRs. The system can identify DDIs shared by an entire drug class. The class-class interaction analysis generates putative drug class interactions. The system analyzes laboratory reports commonly recorded in EMRs that may be used as markers of these class-specific DDIs.

In one embodiment, the knowledge-based repository may aggregate relevant clinical and/or behavioral knowledge from one or more sources. In an embodiment, one or more clinical and/or behavioral experts may manually specify the required knowledge. In another embodiment, an ontology-based approach may be used. For example, the knowledge-based repository may leverage the semantic web using techniques, such as statistical relational learning (SRL). SRL may expand probabilistic reasoning to complex relational domains, such as the semantic web. The SRL may achieve this using a combination of representational formalisms (e.g., logic and/or frame based systems with probabilistic models). For example, the SRL may employ Bayesian logic or Markov logic. For example, if there are two objects—'asian male' and 'smartness', they may be connected using the relationship 'Asian males are smart'. This relationship may be given a weight (e.g., 0.3). This relationship may vary from time to time (populations trend over years/decades). By leveraging the knowledge in the semantic web (e.g., all references and discussions on the web where 'blonde' and 'smartness' are used and associated) the degree of relationship may be interpreted from the sentiment of such references (e.g., positive sentiment: TRUE; negative sentiment: FALSE). Such sentiments and the volume of discussions may then be transformed into weights. Accordingly, although the system originally assigned a weight of 0.3, based on information from semantic web about Asian males and smartness, may be revised to 0.9.

In an embodiment, Markov logic may be applied to the semantic web using two objects: first-order formulae and their weights. The formulae may be acquired based on the semantics of the semantic web languages. In one embodiment, the SRL may acquire the weights based on probability values specified in ontologies. In another embodiment, where the ontologies contain individuals, the individuals can be used to learn weights by generative learning. In some embodiments, the SRL may learn the weights by matching and analyzing a predefined corpus of relevant objects and/or textual resources. These techniques may be used to not only to obtain first-order waited formulae for clinical parameters, but also general information. This information may then be used when making inferences.

For example, if the first order logic is 'obesity causes hypertension, there are two objects involved: obesity and hypertension. If data on patients with obesity and as to whether they were diagnosed with diabetes or not is available, then the weights for this relationship may be learnt from the data. This may be extended to non-clinical examples such as person's mood, beliefs etc.

The pattern recognizer may use the temporal dimension of data to learn representations. The pattern recognizer may include a pattern storage system that exploits hierarchy and analytical abilities using a hierarchical network of nodes. The nodes may operate on the input patterns one at a time. For every input pattern, the node may provide one of three operations: 1. Storing patterns, 2. Learning transition probabilities, and 3. Context specific grouping.

A node may have a memory that stores patterns within the field of view. This memory may permanently store patterns and give each pattern a distinct label (e.g. a pattern number). Patterns that occur in the input field of view of the node may be compared with patterns that are already stored in the memory. If an identical pattern is not in the memory, then the input pattern may be added to the memory and given a distinct pattern number. The pattern number may be arbitrarily assigned and may not reflect any properties of the pattern. In one embodiment, the pattern number may be encoded with one or more properties of the pattern.

In one embodiment, patterns may be stored in a node as rows of a matrix. In such an embodiment, C may represent a pattern memory matrix. In the pattern memory matrix, each row of C may be a different pattern. These different patterns may be referred to as C-1, C-2, etc., depending on the row in which the pattern is stored.

The nodes may construct and maintain a Markov graph. The Markov graph may include vertices that correspond to the store patterns. Each vertex may include a label of the pattern that it represents. As new patterns are added to the memory contents, the system may add new vertices to the Markov graph. The system may also create a link between to vertices to represent the number of transition events between the patterns corresponding to the vertices. For example, when an input pattern is followed by another input pattern j for the first time, a link may be introduced between the vertices i and j and the number of transition events on that link may be set to 1. System may then increment the number of transition counts on the link from i and j whenever a pattern from i to pattern j is observed. The system may normalize the Markov graph such that the links estimate the probability of a transaction. Normalization may be achieved by dividing the number of transition events on the outgoing links of each vertex by the total number of transition events from the vertex. This may be done for all vertices to obtain a normalized Markov graph. When normalization is completed, the sum of the transition probabilities for each node should add to 1. The system may update the Markov graph continuously to reflect new probability estimates.

The system may also perform context-specific grouping. To achieve this, the system may partition a set of vertices of the Markov graph into a set of temporal groups. Each temporal group may be a subset of that set of vertices of the Markov graph. The partitioning may be performed such that the vertices of the same temporal group are highly likely to follow one another.

The node may use Hierarchical Clustering (HC) to for the temporal groups. The HC algorithm may take a set of pattern labels and their pair-wise similarity measurements as inputs to produce clusters of pattern labels. The system may cluster the pattern labels such that patterns in the same cluster are similar to each other.

As data is fed into the pattern recognizer, the transition probabilities for each pattern and pattern-of-patterns may be updated based on the Markov graph. This may be achieved by updating the constructed transition probability matrix. This may be done for each pattern in every category of patterns. Those with higher probabilities may be chosen and placed in a separate column in the database called a prediction list.

Logical relationships among the patterns may be manually defined based on the clinical relevance. This relationship is specified as first-order logic predicates along with probabilities. These probabilities may be called beliefs. In one embodiment, a Bayesian Belief Network (BBN) may be used to make predictions using these beliefs. The BBN may be used to obtain the probability of each occurrence. These logical relationships may also be based on predicates stored the knowledge base.

The pattern recognizer may also perform optimization for the predictions. In one embodiment, this may be accomplished by comparing the predicted probability for a relationship with its actual occurrence. Then, the difference between the two may be calculated. This may be done for p occurrences of the logic and fed into a K-means clustering algorithm to plot the Euclidean distance between the points. A centroid may be obtained by the algorithm, forming the optimal increment to the difference. This increment may then be added to the (p+1)th occurrence. Then, the process may be repeated. This may be done until the pattern recognizer predicts logical relationships up to a specified accuracy threshold. Then, the results may be considered optimal.

When a node is at the first level of the hierarchy, its input may come directly from the data source, or after some preprocessing. The input to a node at a higher-level may be the concatenation of the outputs of the nodes that are directly connected to it from a lower level. Patterns in higher-level nodes may represent particular coincidences of their groups of children. This input may be obtained as a probability distribution function (PDF). From this PDF, the probability that a particular group is active may be calculated as the probability of the pattern that has the maximum likelihood among all the patterns belonging to that group.

The system can use an expert system that can assess hypertension in according with the guidelines. In addition, the expert system can use diagnostic information and apply the following rules to assess hypertension:

Hemoglobin/hematocrit: Assesses relationship of cells to fluid volume (viscosity) and may indicate risk factors such as hypercoagulability, anemia.

Blood urea nitrogen (BUN)/creatinine: Provides information about renal perfusion/function.

Glucose: Hyperglycemia (diabetes mellitus is a precipitator of hypertension) may result from elevated catecholamine levels (increases hypertension).

Serum potassium: Hypokalemia may indicate the presence of primary aldosteronism (cause) or be a side effect of diuretic-therapy.

Serum calcium: Imbalance may contribute to hypertension.

Lipid panel (total lipids, high-density lipoprotein [HDL], low-density lipoprotein [LDL], cholesterol, triglycerides, phospholipids): Elevated level may indicate predisposition for/presence of atheromatous plaques.

Thyroid studies: Hyperthyroidism may lead or contribute to vasoconstriction and hypertension.

Serum/urine aldosterone level: May be done to assess for primary aldosteronism (cause).

Urinalysis: May show blood, protein, or white blood cells; or glucose suggests renal dysfunction and/or presence of diabetes.

Creatinine clearance: May be reduced, reflecting renal damage.

Urine vanillylmandelic acid (VMA) (catecholamine metabolite): Elevation may indicate presence of pheochromocytoma (cause); 24-hour urine VMA may be done for assessment of pheochromocytoma if hypertension is intermittent.

Uric acid: Hyperuricemia has been implicated as a risk factor for the development of hypertension.

Renin: Elevated in renovascular and malignant hypertension, salt-wasting disorders.

Urine steroids: Elevation may indicate hyperadrenalism, pheochromocytoma, pituitary dysfunction, Cushing's syndrome.

Intravenous pyelogram (IVP): May identify cause of secondary hypertension, e.g., renal parenchymal disease, renal/ureteral-calculi.

Kidney and renography nuclear scan: Evaluates renal status (TOD).

Excretory urography: May reveal renal atrophy, indicating chronic renal disease.

Chest x-ray: May demonstrate obstructing calcification in valve areas; deposits in and/or notching of aorta; cardiac enlargement.

Computed tomography (CT) scan: Assesses for cerebral tumor, CVA, or encephalopathy or to rule out pheochromocytoma.

Electrocardiogram (ECG): May demonstrate enlarged heart, strain patterns, conduction disturbances. Note: Broad, notched P wave is one of the earliest signs of hypertensive heart disease.

The system may also be adaptive. In one embodiment, every level has a capability to obtain feedback information from higher levels. This feedback may inform about certain characteristics of information transmitted bottom-up through the network. Such a closed loop may be used to optimize each level's accuracy of inference as well as transmit more relevant information from the next instance.

The system may learn and correct its operational efficiency over time. This process is known as the maturity process of the system. The maturity process may include one or more of the following flow of steps:

a. Tracking patterns of input data and identifying predefined patterns (e.g. if the same pattern was observed several times earlier, the pattern would have already taken certain paths in the hierarchical node structure).

b. Scanning the possible data, other patterns (collectively called Input Sets (IS)) required for those paths. It also may check for any feedback that has come from higher levels of hierarchy. This feedback may be either positive or negative (e.g., the relevance of the information transmitted to the inferences at higher levels). Accordingly, the system may decide whether to send this pattern higher up the levels or not, and if so whether it should it send through a different path.

c. Checking for frequently required ISs and pick the top 'F' percentile of them.

d. Ensuring it keeps this data ready.

In one embodiment, information used at every node may act as agents reporting on the status of a hierarchical network. These agents are referred to as Information Entities (In En). In En may provide insight about the respective inference operation, the input, and the result which collectively is called knowledge.

This knowledge may be different from the KB. For example, the above described knowledge may include the dynamic creation of insights by the system based on its inference, whereas the KB may act as a reference for inference and/or analysis operations. The latter being an input to inference while the former is a product of inference. When this knowledge is subscribed to by a consumer (e.g. administering system or another node in a different layer) it is called "Knowledge-as-a-Service (KaaS)" One embodiment processes behavior models are classified into four categories as follows:

a. Outcome-based;
b. Behavior-based;
c. Determinant-based; and
d. Intervention-based.

One or more of the following rules of thumb may be applied during behavioral modeling:
One or more interventions affect determinants;
One or more determinants affect behavior; and
One or more behaviors affect outcome.

A behavior is defined to be a characteristic of an individual or a group towards certain aspects of their life such as health, social interactions, etc. These characteristics are displayed as their attitude towards such aspects. In analytical terms, a behavior can be considered similar to a habit. Hence, a behavior may be observed POP' for a given data from a user. An example of a behavior is dietary habits. Determinants may include causal factors for behaviors. They either cause someone to exhibit the same behavior or cause behavior change. Certain determinants are quantitative but most are qualitative. Examples include one's perception about a food, their beliefs, their confidence levels, etc. Interventions are actions that affect determinants. Indirectly they influence behaviors and hence outcomes. System may get both primary and secondary sources of data. Primary sources may be directly reported by the end-user and AU. Secondary data may be collected from sensors such as their mobile phones, cameras, microphone, as well as those collected from general sources such as the semantic web.

These data sources may inform the system about the respective interventions. For example, to influence a determinant called forgetfulness which relates to a behavior called medication, the system sends a reminder at an appropriate time, as the intervention. Then, feedback is obtained whether the user took the medication or not. This helps the system in confirming if the intervention was effective. The system may track a user's interactions and request feedback about their experience through assessments. The system may use this information as part of behavioral modeling to determine if the user interface and the content delivery mechanism have a significant effect on behavior change with the user. The system may use this information to optimize its user interface to make it more personalized over time to best suit the users, as well as to best suit the desired outcome.

The system also may accommodate data obtained directly from the end-user, such as assessments, surveys, etc. This enables users to share their views on interventions, their effectiveness, possible causes, etc. The system's understanding of the same aspects is obtained by way of analysis and service by the pattern recognizer.

Both system-perceived and end user-perceived measures of behavioral factors may be used in a process called Perception Scoring (PS). In this process, hybrid scores may be designed to accommodate both above mentioned aspects of behavioral factors. Belief is the measure of confidence the system has, when communicating or inferring on information. Initially higher beliefs may be set for user-perceived measures.

Over time, as the system finds increasing patterns as well as obtains feedback in pattern recognizer, the system may evaluate the effectiveness of intervention(s). If the system triggers an intervention based on user-perceived measures and it doesn't have significant effect on the behavior change, the system may then start reducing its belief for user-perceived measures and instead will increase its belief for system-perceived ones. In other words, the system starts believing less in the user and starts believing more in itself. Eventually this reaches a stage where system can understand end-users and their behavioral health better than end-users themselves. When perception scoring is done for each intervention, it may result in a score called Intervention Effectiveness Score (IES).

Perception scoring may be done for both end-users as well as AU. Such scores may be included as part of behavior models during cause-effect analysis.

Causes may be mapped with interventions, determinants, and behavior respectively in order of the relevance. Mapping causes with interventions helps in back-tracking the respective AU for that cause. In simple terms, it may help in identifying whose actions have had a pronounced effect on the end-user's outcome, by how much and using which intervention. This is very useful in identifying AUs who are very effective with specific interventions as well as during certain event context. Accordingly, they may be provided a score called Associated User Influence Score. This encompasses information for a given end-user, considering all interventions and possible contexts relevant to the user's case.

The system may construct one or plans including one or more interventions based on analysis performed, and may be implemented. For example, the system may analyze eligibility of an intervention for a given scenario, evaluating eligibility of two or more interventions based on combinatorial effect, prioritizing interventions to be applied, based on occurrence of patterns (from pattern recognizer), and/or submitting an intervention plan to the user or doctor in a format readily usable for execution.

This system may rely on the cause-effect analysis for its planning operations. A plan consists of interventions and a respective implementation schedule. Every plan may have several versions based on the users involved in it. For example, the system may have a separate version for the physician as compared to a patient. They will in turn do the task and report back to the system. This can be done either directly or the system may indirectly find it based on whether a desired outcome with the end user was observed or not.

The methodology may be predefined by an analyst. For every cause, which can be an intervention(s), determinant(s), behavior(s) or combinations of the same, the analyst may specify one or more remedial actions. This may be specified from the causal perspective and not the contextual perspective. Accordingly, the system may send a variety of data and information to pattern recognizer and other services, as feedback, for these services to understand about the users. This understanding may affect their next set of plans which in turn becomes an infinite cyclic system where system affects the users while getting affected by them at the same time. Such a system is called a reflexive-feedback enabled system. The system may user both positive and negative reflexive-feedback, though the negative feedback aspect may predominantly be used for identifying gaps that the system needs to address. The system may provide information, such as one or more newly identified patterns, to an analyst (e.g., clinical analyst or doctor). In the use case, the doctor may be presented with one or more notifications to address the relationship between carbohydrates and the medication that the patient is taking. One embodiment of the system operation includes receiving feedback relating to the plan, and revising the plan based on the feedback; the feedback being one or more patient behaviors that occur after the plan; the revised plan including one or more additional interventions selected based on the feedback; the one or more patient behaviors that occur after the plan include a behavior transition; determining one or more persons to associate with the identified intervention; automatically revising probabilities from the collected information; storing the revised probabilities, wherein the revised probabilities are used to determine the plan; and/or automatically make one or more inferences based on machine learning using one or more of the clinical information, behavior information, or personal information. Hypertension metrics may be one type of metrics utilized within the principles of the present disclosure. A hypertension score can be based on any type of alpha-numeric or visual analog scale. Hypertension scales may or may not be clinically validated and may use any scale (e.g. 1-100, 1-10, 1-4), picture, symbol, color, character, number, sound, letter, or written description of hypertension to facilitate the communication of a patient's hypertension level. The type of hypertension scale used may be determined according to a patient's and/or healthcare provider's preferences, and may also be determined based on the needs of a patient including, for example, the patient's age and/or communication capability. In further embodiments, the selected hypertension scale(s) may be determined by a service provider, such as, e.g., an organization implementing the principles of the present disclosure via a suitable software program or application.

Another metric may include a functionality score. A functionality score can be based on any type of alpha-numeric or visual analog scale. Non-limiting examples include the American Chronic Pain Association Quality of Life (ACPA QoL) Scale, Global Assessment of Functioning (GAF) Scale, and Short Form SF-36 Health Survey. Functionality scales may or may not be clinically validated and may use any picture, symbol, color, character, number, sound, letter, written description of quality of life, or physical functioning to facilitate communication of a patient's functionality level. The functionality score may be, e.g., based on an assessment of a patient's ability to exercise as well as perform daily tasks and/or perform routine tasks such as, e.g., getting dressed, grocery shopping, cooking, cleaning, climbing stairs, etc. In some embodiments, the selected functionality scale(s) may be determined by a service provider, such as, e.g., an organization implementing the principles of the present disclosure via a suitable software program or application.

A further metric may include a patient's medication usage. Medication use encompasses pharmacologic and therapeutic agents used to treat, control, and/or alleviate hypertension, including prescription drugs as well as over-the-counter medications, therapeutic agents, and other non-prescription agents. Medication use may include different classes of pharmacologic agents. Medication use can be reported in any appropriate units, such as number of doses taken, percentage of treatment plan completed, frequency of doses, and/or dose strength; and may also specify additional information such as the type of formulation taken and the route of administration (oral, enteral, topical, transdermal, parenteral, sublingual etc.). Molecular alternatives (e.g., acid, salt, solvate, complex, and pro-drug forms, etc.) and formulations (e.g., solid, liquid, powder, gel, and suspensions, etc.) are further contemplated. Reported medication use may, for example, include the number of doses and types of medication taken since a previous reported medication use, and may also indicate the number of closes and types of medication taken within a period of time, such as within, the previous 2 hours, 4 hours, 6 hours, 12 hours, 18 hours, 24 hours, 36 hours, or 48 hours. In some embodiments, for example, medication use may be reported in terms of dosage units recommended by a manufacturer or healthcare provider for a given medication (e.g., minimum, maximum, or range of appropriate unit dosage per unit time).

Reported medication use may allow for tracking compliance with a treatment regime. For example, a record of reported medication use may assist a healthcare provider in evaluating medication efficacy, adjusting dosage, and/or adding other medications as necessary.

In some embodiments of the present disclosure, a patient or healthcare provider may create a patient profile comprising, e.g., identifying, characterizing, and/or medical information, including information about a patient's medical history, profession, and/or lifestyle. Further examples of information that may be stored in a patient profile includes diagnostic information such as family medical history, medical symptoms, duration of hypertension, localized vs. general hypertension, etc. Further contemplated as part of a patient profile are non-pharmacologic treatment(s) (e.g., chiropractic, radiation, holistic, psychological, acupuncture, etc.), lifestyle characteristics (e.g., diet, alcohol intake, smoking habits), cognitive condition, behavioral health, and social well-being.

A patient profile may, for example, be stored in a database and accessible for analysis of the patient's reported hypertension metrics. In some embodiments, a patient profile may be created before collecting and/or transmitting a set of hypertension metrics to be received by a server and/or database in other embodiments, a patient profile may be created concurrently with, or even after transmitting/receiving one or more hypertension metrics. In some embodiments a patient profile may be used to establish one or more hypertension metric e and/or reference values. A patient profile may, for example, allow for setting threshold values or ranges, wherein reported hypertension metrics that fall outside of those limits trigger an alert to be sent to the patient or a healthcare provider. Threshold values, limits, or ranges may also be set without reference to a patient profile. In some embodiments, one or more target value(s) (e.g., hypertension metric value(s)) may be set to determine how the reported hypertension metrics compare with the target value(s).

The methods and systems disclosed herein may rely on one or more algorithm(s) to analyze one or more of the described metrics. The algorithm(s) may comprise analysis of data reported in real-time, and may also analyze data reported in real-time in conjunction with auxiliary data stored in a hypertension management database. Such auxiliary data may comprise, for example, historical patient data such as previously-reported hypertension metrics (e.g., hypertension scores, functionality scores, medication use), personal medical history, and/or family medical history. In some embodiments, for example, the auxiliary data includes at least one set of hypertension metrics previously reported and stored for a patient. In some embodiments, the auxiliary data includes a patient profile such as, e.g., the patient profile described above. Auxiliary data may also include statistical data, such as hypertension metrics pooled for a plurality of patients within a similar group or subgroup. Further, auxiliary data may include clinical guidelines such as guidelines relating to hypertension management, including evidence-based clinical practice guidelines on the management of acute and/or chronic hypertension or other chronic conditions.

Analysis of a set of hypertension metrics according to the present disclosure may allow for calibration of the level, degree, and/or quality of hypertension experienced by providing greater context to patient-reported data. For example, associating a hypertension score of 7 out of 10 with high functionality for a first patient, and the same score with low functionality for a second patient may indicate a relatively greater debilitating effect of hypertension on the second patient than the first patient. Further, a high hypertension score reported by a patient taking a particular medication such as opioid analgesics may indicate a need to adjust the patient's treatment plan. Further, the methods and systems disclosed herein may provide a means of assessing relative changes in a patient's distress due to hypertension over time. For example, a hypertension score of 5 out of 10 for a patient who previously reported consistently lower hypertension scores, e.g., 1 out of 10, may indicate a serious issue requiring immediate medical attention.

Any combination(s) of hypertension metrics may be used for analysis in the systems and methods disclosed. In some embodiments, for example, the set of hypertension metrics comprises at least one hypertension score and at least one functionality score. In other embodiments, the set of hypertension metrics may comprise at least one hypertension score, at least one functionality score, and medication use. More than one set of hypertension metrics may be reported and analyzed at a given time. For example, a first set of hypertension metrics recording a patient's current status and a second set of hypertension metrics recording the patient's status at an earlier time may both be analyzed and may also be used to generate one or more recommended actions.

Each hypertension metric may be given equal weight in the analysis, or may also be given greater or less weight than other hypertension metrics included in the analysis. For example, a functionality score may be given greater or less weight with respect to a hypertension score and/or medication use. Whether and/or how to weigh a given hypertension metric may be determined according to the characteristics or needs of a particular patient. As an example, Patient A reports a hypertension score of 8 (on a scale of 1 to 10 where 10 is the most severe hypertension) and a functionality score of 9 (on a scale of 1 to 10 where 10 is highest functioning), while Patient B reports a hypertension score of 8 but a functionality score of 4. The present disclosure provides for the collection, analysis, and reporting of this information, taking into account the differential impact of one hypertension score on a patient's functionality versus that same hypertension score's impact on the functionality of a different patient.

Hypertension metrics may undergo a pre-analysis before inclusion in a set of hypertension metrics and subsequent application of one or more algorithms. For example, a raw score may be converted or scaled according to one or more algorithm(s) developed for a particular patient. In some embodiments, for example, a non-numerical raw score may be converted to a numerical score or otherwise quantified prior to the application of one or more algorithms. Patients and healthcare providers may retain access to raw data (e.g., hypertension metric data prior to any analysis)

Algorithm(s) according, to the present disclosure may analyze the set of hypertension metrics according to any suitable methods known in the art. Analysis may comprise, for example, calculation of statistical averages, pattern recognition, application of mathematical models, factor analysis, correlation, and/or regression analysis. Examples of analyses that may be used herein include, but are not limited to, those disclosed in U.S. Patent Application Publication No. 2012/0246102 A1 the entirety of which is incorporated herein by reference.

The present disclosure further provides for the determination of an aggregated hypertension assessment score. In some embodiments, for example, a set of pairs metrics may be analyzed to generate a comprehensive and/or individualized assessment of hypertension by generating a composite or aggregated score. In such embodiments, the aggregated score may include a combination of at least one hypertension score, at least one functionality score, and medication use. Additional metrics may also be included in the aggregated score. Such metrics may include, but are not limited to, exercise habits, mental well-being, depression, cognitive functioning, medication side effects, etc. Any of the aforementioned types of analyses may be used in determining an aggregated score.

The algorithm(s) may include a software program that may be available for download to an input device in various versions. In some embodiments, for example, the algorithm(s) may be directly downloaded through the Internet or other suitable communications means to provide the capability to troubleshoot a health issue in real-time. The algorithm(s) may also be periodically updated, e.g., provided content changes, and may also be made available for download to an input device.

The methods presently disclosed may provide a healthcare provider with a more complete record of a patient's day-to-day status. By having access to a consistent data stream of hypertension metrics for a patient, a healthcare provider may be able to provide the patient with timely advice and real-time coaching on hypertension management options and solutions. A patient may, for example, seek and/or receive feedback on hypertension management without waiting for an upcoming appointment with a healthcare provider or scheduling a new appointment. Such real-time communication capability may be especially beneficial to provide patients with guidance and treatment options during intervals between appointments with a healthcare provider. Healthcare providers may also be able to monitor a patient's status between appointments to timely initiate, modify, or terminate a treatment plan as necessary. For example, a patient's reported medication use may convey whether the patient is taking too little or too much medication. In some embodiments, an alert may be triggered to notify the patient and/or a healthcare provider of the amount of medication taken, e.g., in comparison to a prescribed treatment plan. The healthcare provider could, for example, contact the patient to discuss the treatment plan. The methods disclosed herein may also provide a healthcare provider with a longitudinal review of how a patient responds to hypertension over time. For example, a healthcare provider may be able to determine whether a given treatment plan adequately addresses a patient's needs based on review of the patient's reported hypertension metrics and analysis thereof according to the present disclosure. Analysis of patient data according to the methods presently disclosed may generate one or more recommended actions that may be transmitted and displayed on an output device. In some embodiments, the analysis recommends that a patient make no changes to his/her treatment plan or routine. In other embodiments, the analysis generates a recommendation that the patient seek further consultation with a healthcare provider and/or establish compliance with a prescribed treatment plan. In other embodiments, the analysis may encourage a patient to seek immediate medical attention. For example, the analysis may generate an alert to be transmitted to one or more output devices, e.g., a first output device belonging to the patient and a second output device belonging to a healthcare provider, indicating that the patient is in need of immediate medical treatment. In some embodiments, the analysis may not generate a recommended action. Other recommended actions consistent with the present disclosure may be contemplated and suitable according to the treatment plans, needs, and/or preferences for a given patient.

The present disclosure further provides a means for monitoring a patient's medication use to determine when his/her prescription will run out and require a refill. For example, a patient profile may be created that indicates a prescribed dosage and frequency of administration, as well as total number of dosages provided in a single prescription. As the patient reports medication use, those hypertension metrics may be transmitted to a server and stored in a database in connection with the patient profile. The patient profile stored on the database may thus continually update with each added metric and generate a notification to indicate when the prescription will run out based on the reported medication use. The notification may be transmitted and displayed on one or more output devices, e.g., to a patient and/or one or more healthcare providers. In some embodiments, the one or more healthcare providers may include a pharmacist. For example, a pharmacist may receive notification of the anticipated date a prescription will run out in order to ensure that the prescription may be timely refilled.

Patient data can be input for analysis according to the systems disclosed herein through any data-enabled device including, but not limited to, portable/mobile and stationary communication devices, and portable/mobile and stationary computing devices. Non-limiting examples of input devices suitable for the systems disclosed herein include smart phones, cell phones, laptop computers, netbooks, personal computers (PCs), tablet PCs, fax machines, personal digital assistants, and/or personal medical devices. The user interface of the input device may be web-based, such as a web page, or may also be a stand-alone application. Input devices may provide access to software applications via mobile and wireless platforms, and may also include web-based applications.

The input device may receive data by having a user, including, but not limited to, a patient, family member, friend, guardian, representative, healthcare provider, and/or caregiver, enter particular information via a user interface, such as by typing and/or speaking. In some embodiments, a server may send a request for particular information to be entered by the user via an input device. For example, an input device may prompt a user to enter sequentially a set of hypertension metrics, e.g., a hypertension score, a functionality score, and information regarding use of one or more medications (e.g., type of medication, dosage taken, time of day, route of administration, etc.). In other embodiments, the user may enter data into the input device without first receiving a prompt. For example, the user may initiate an application or web-based software program and select an option to enter one or more hypertension metrics. In some embodiments, one or more hypertension scales and/or functionality scales may be preselected by the application or software program. For example, a user may have the option of selecting the type of hypertension scale and/or functionality scale for reporting hypertension metrics within the application or software program. In other embodiments, an application or software program may not include preselected hypertension scales or functionality scales such that a user can employ any hypertension scale and/or functionality scale of choice.

The user interface of an input device may allow a user to associate hypertension metrics with a particular date and/or time of day. For example, a user may report one or more hypertension metrics to reflect a patient's present status. A user may also report one or more hypertension metrics to reflect a patient's status at an earlier time.

Patient data may be electronically transmitted from an input device over a wired or wireless medium to a server, e.g., a remote server. The server may provide access to a database for performing an analysis of the data transmitted, e.g., set of hypertension metrics. The database may comprise auxiliary data for use in the analysis as described above. In some embodiments, the analysis may be automated, and may also be capable of providing real-time feedback to patients and/or healthcare providers.

The analysis may generate one or more recommended actions, and may transmit the recommended action(s) over at wired or wireless medium for display on at least one output device. The at least one output device may include, e.g., portable/mobile and stationary communication devices, and portable/mobile and stationary computing devices. Non-limiting examples of output devices suitable for the systems disclosed herein include smart phones, cell phones, laptop computers, netbooks, personal computers (PCs), tablet PCs, fax machines, personal digital assistants, and/or personal medical devices. In some embodiments, the input device is the at least one output device. In other embodiments, the input device is one of multiple output devices. In some embodiments of the present disclosure, the one or more recommended actions are transmitted and displayed on each of two output devices. In such an example, one output device may belong to a patient and the other device may belong to a healthcare provider.

The present disclosure also contemplates methods and systems in a language suitable for communicating with the patient and/or healthcare provider, including languages other than English. A patient's medical data may be subject to confidentiality regulations and protection. Transmitting, analyzing, and/or storing information according to the methods and systems disclosed herein may be accomplished through secure means, including HIPPA-compliant procedures and use of password-protected devices, servers, and databases.

The systems and methods presently disclosed may be especially beneficial in outpatient, home, and/or on-the-go settings. The systems and methods disclosed herein may also be used as an inpatient tool and/or in controlled medication administration such as developing a personalized treatment plan. In addition to monitoring health parameters, the system can include interventional devices such as a defibrillator. The defibrillator function is enabled by providing electrical energy of a selected energy/power level/voltage/current level or intensity delivered for a selected duration upon sensing certain patterns of undesirable heart activity wherein said undesirable heart activity necessitates an external delivery of a controlled electrical energy pulse for stimulating a selected heart activity. The defibrillator function is enabled by an intelligent defibrillator appliance that operates in a manner similar to the functions of an intelligent ECG appliance with the additional capability of providing external electrical stimuli via for example a wireless contact system pasted on various locations of the torso. The electrical stimuli are delivered in conjunction with the intelligent defibrillator device or the mobile device performing the additional functions of an intelligent defibrillator appliance. The control actions for providing real time stimuli to the heart of electrical pulses, is enabled by the intelligent defibrillator appliance by itself or in conjunction with an external server/intelligent appliance where the protocols appropriate for the specific individual are resident. The defibrillation actions are controlled in conjunction with the real time ECG data for providing a comprehensive real-time solution to the individual suffering from abnormal or life-threatening heart activity/myocardial infraction. Additionally, by continuously wearing the paste on wireless contacts that can provide the electrical impulse needed, the individual is instantaneously able to get real time attention/action using a specifically designed wearable intelligent defibrillator appliance or a combination of an intelligent ECG plus defibrillator appliance. Further the mobile device such as a cellular telephone or other wearable mobile devices can be configured with the appropriate power sources and the software for performing the additional functions of an intelligent defibrillator appliance specifically tailored to the individual.

The cellular telephone/mobile device can receive signals from the ECG machine/appliance or as an intermediary device that transmits/receives the ECG data and results from a stationary or portable ECG appliance. The ability of the individual to obtain an ECG profile of the heart at a selected time and in a selected location is critical to getting timely attention and for survival. Getting attention within 10 to 20 minutes of a heart attack is crucial beyond that the chances for survival diminish significantly. The smart phone helps the patient to quickly communicate his/her location and or discover the location of the nearest health care facility that has the requisite cardiac care facilities and other facilities. The mobile device that the individual is carrying on the person is enabled to provide the exact location of the individual in conjunction with the global positioning system. In addition, the system is enabled to provide the directions and estimated travel time to/from the health care facility to the specific mobile device/individual.

Yet other intervention can include music, image, or video. The music can be synchronized with respect to a blood pulse rate in one embodiment, and in other embodiments to biorhythmic signal—either to match the biorhythmic signal, or, if the signal is too fast or too slow, to go slightly slower or faster than the signal, respectively. In order to entrain the user's breathing, a basic melody is preferably played which can be easily identified by almost all users as corresponding to a particular phase of respiration. On top of the basic melody, additional layers are typically added to make the music more interesting, to the extent required by the current breathing rate, as described hereinabove. Typically, the basic melody corresponding to this breathing includes musical cords, played continuously by the appropriate instrument during each phase. For some applications, it is desirable to elongate slightly the length of one of the respiratory phases, typically, the expiration phase. For example, to achieve respiration which is 70% expiration and 30% inspiration, a musical composition written for an E:I ratio of 2:1 may be played, but the expiration phase is extended by a substantially-unnoticed 16%, so as to produce the desired respiration timing. The expiration phase is typically extended either by slowing down the tempo of the notes therein, or by extending the durations of some or all of the notes.

Although music for entraining breathing is described hereinabove as including two phases, it will be appreciated by persons skilled in the art that the music may similarly include other numbers of phases, as appropriate. For example, user may be guided towards breathing according to a 1:2:1:3 pattern, corresponding to inspiration, breath holding (widely used in Yoga), expiration, and post-expiratory pause (rest state).

In one embodiment, the volume of one or more of the layers is modulated responsive to a respiration characteristic (e.g., inhalation depth, or force), so as to direct the user to change the characteristic, or simply to enhance the user's connection to the music by reflecting therein the respiration characteristic. Alternatively, or additionally, parameters of the sound by each of the musical instruments may be varied to increase the user's enjoyment. For example, during slow breathing, people tend to prefer to hear sound patterns that have smoother structures than during fast breathing and/or aerobic exercise. Further alternatively or additionally, random musical patterns and/or digitized natural sounds (e.g., sounds of the ocean, rain, or wind) are added as a decoration layer, especially for applications which direct the user into very slow breathing patterns. The inventor has found that during very slow breathing, it is desirable to remove the user's focus from temporal structures, particularly during expiration.

Still further alternatively or additionally, the server maintains a musical library, to enable the user to download appropriate music and/or music-generating patterns from the Internet into device. Often, as a user's health improves, the music protocols which were initially stored in the device are no longer optimal, so the user downloads the new protocols, by means of which music is generated that is more suitable for his new breathing training. The following can be done:
obtaining clinical data from one or more laboratory test equipment and checking the data on a blockchain;
obtaining genetic clinical data from one or more genomic equipment and storing genetic markers in the EMR/HER including germ line data and somatic data over time;
obtaining clinical data from a primary care or a specialist physician database;
obtaining clinical data from an in-patient care database or from an emergency room database;
saving the clinical data into a clinical data repository;

obtaining health data from fitness devices or from mobile phones;

obtaining behavioral data from social network communications and mobile device usage patterns;

saving the health data and behavioral data into a health data repository separate from the clinical data repository; and providing a decision support system (DSS) to apply genetic clinical data to the subject, and in case of an adverse event for a drug or treatment, generating a drug safety signal to alert a doctor or a manufacturer, wherein the DSS includes rule-based alerts on pharmacogenetics, oncology drug regimens, wherein the DSS performs ongoing monitoring of actionable genetic variants.

FIG. 7E illustrates one embodiment of a system for collaboratively treating a patient with a disease such as cancer. In this embodiment, a treating physician/doctor logs into a consultation system 1 and initiates the process by clicking on "Create New Case" (500). Next, the system presents the doctor with a "New Case Wizard" which provides a simple, guided set of steps to allow the doctor to fill out an "Initial Assessment" form (501). The doctor may enter Patient or Subject Information (502), enter Initial Assessment of patient/case (504), upload Test Results, Subject Photographs and X-Rays (506), accept Payment and Service Terms and Conditions (508), review Summary of Case (510), or submit Forms to a AI machine based "consultant" such as a Hearing Service AI Provider (512). Other clinical information for the cancer subject includes the imaging or medical procedure directed towards the specific disease that one of ordinary skill in the art can readily identify. The list of appropriate sources of clinical information for cancer includes but it is not limited to: CT scan, MRI scan, ultrasound scan, bone scan, PET Scan, bone marrow test, barium X-ray, endoscopy, lymphangiogram, IVU (Intravenous urogram) or IVP (IV pyelogram), lumbar puncture, cystoscopy, immunological tests (anti-malignant antibody screen), and cancer marker tests.

After the case has been submitted, the AI Machine Consultant can log into the system 1 and consult/process the case (520). Using the Treating Doctors Initial Assessment and Photos/X-Rays, the Consultant will click on "Case Consultation" to initiate the "Case Consultation Wizard" (522). The consultant can fill out the "Consultant Record Analysis" form (524). The consultant can also complete the "Prescription Form" (526) and submit completed forms to the original Treating Doctor (528). Once the case forms have been completed by the Consulting Doctor, the Treating Doctor can access the completed forms using the system. The Treating Doctor can either accept the consultation results (i.e. a pre-filled Prescription form) or use an integrated messaging system to communicate with the Consultant (530). The Treating Doctor can log into the system (532), click on Patient Name to review (534), review the Consultation Results (Summary Letter and pre-filled Prescription Form) (536). If satisfied, the Treating Doctor can click "Approve Treatment" (538), and this will mark the case as having being approved (540). The Treating Doctor will be able to print a copy of the Prescription Form and the Summary Letter for submission to hearing aid manufacturer or provider (542). Alternatively, if not satisfied, the Treating Doctor can initiate a computer dialog with the Consultant by clicking "Send a Message" (544). The Treating Doctor will be presented with the "Send a Message" screen where a message about the case under consultation can be written (546). After writing a message, the Treating Doctor would click "Submit" to send the message to the appropriate Consultant (548). The Consultant will then be able to reply to the Treating Doctor's Message and send a message/reply back to the Treating Doctor (550).

Blockchain Authentication

Since the ITE sensors are IoT machines, the ITE device can negotiate contracts on their own (without human) and exchange items of value by presenting an open transaction on the associated funds in their respective wallets. Blockchain token ownership is immediately transferred to a new owner after authentication and verification, which are based on network ledgers within a peer-to-peer network, guaranteeing nearly instantaneous execution and settlement.

A similar process is used to provide secure communications between IoT devices, which is useful for edge IoT devices. The industrial world is adding billions of new IoT devices and collectively these devices generate many petabytes of data each day. Sending all of this data to the cloud is not only very cost prohibitive but it also creates a greater security risk. Operating at the edge ensures much faster response times, reduced risks, and lower overall costs. Maintaining close proximity to the edge devices rather than sending all data to a distant centralized cloud, minimizes latency allowing for maximum performance, faster response times, and more effective maintenance and operational strategies. In addition to being highly secure, the system also significantly reduces overall bandwidth requirements and the cost of managing widely distributed networks.

In some embodiments, the described technology provides a peer-to-peer cryptographic currency trading method for initiating a market exchange of one or more Blockchain tokens in a virtual wallet for purchasing an asset (e.g., a security) at a purchase price. The system can determine, via a two-phase commit, whether the virtual wallet has a sufficient quantity of Blockchain tokens to purchase virtual assets (such as electricity only from renewable solar/wind/ . . . sources, weather data or location data) and physical asset (such as gasoline for automated vehicles) at the purchase price. In various embodiments, in response to verifying via the two-phase commit that the virtual wallet has a sufficient quantity of Blockchain tokens, the IoT machine purchases (or initiates a process in furtherance of purchasing) the asset with at least one of the Blockchain tokens. In one or more embodiments, if the described technology determines that the virtual wallet has insufficient Blockchain tokens for purchasing the asset, the purchase is terminated without exchanging Blockchain tokens.

The present system provides smart contract management with modules that automates the entire lifecycle of a legally enforceable smart contract by providing tools to author the contract so that it is both judge/arbitrator/lawyer readable and machine readable, and ensuring that all contractual obligations are met by integrating with appropriate execution systems, including traditional court system, arbitration system, or on-line enforcement system. Different from the blockchain/bitcoin contract system where payment is made in advance and released when the conditions are electronically determined to be satisfied, this embodiment creates smart contracts that are verifiable, trustworthy, yet does not require advance payments that restrict the applicability of smart contracts. The system has a contract management system (CMS) that helps users in creating smart contracts for deployment. After template creation, when authoring a contract using one of the smart contract templates in one embodiment, the functionality of the flow diagram is implemented by software stored in memory and executed by a processor. In other embodiments, the functionality can be performed by hardware, or any combination of hardware and software.

A smart contract is a computerized transaction protocol that executes the terms of a contract. A smart contract can have the following fields: object of agreement, first party blockchain address, second party blockchain address, essential content of contract, signature slots and blockchain ID associated with the contract. The user logs into the system to author a smart contract. The system then retrieves the appropriate contract template for the user, and a user interface renderer displays the corresponding deal sheet user interface to the user. The selection of the appropriate contract template can be based on many factors, including the role of the user, the intended parties to the contract, the type of contract desired, etc. At 4, the user enters the information that is requested by the user interface based on the attributes displayed. Because the user interface is tailored specifically to the desired type of contract, the required contract terms information for that type of contract will be entered by the user as guided by the attributes of the template. The user may interact with the user interface through a single page or through multiple pages in a particular sequence with a forms wizard, or through the selection of tabs. In one embodiment, the user interface is rendered as a mark-up language such as XML showing the structure of the requirements of the contract. In other embodiments, the user interface is rendered as an Excel worksheet, Word document, or other application compatible format that can be read by the contracting parties, lawyers, judges, and jury. At 6, the contract is generated based on the user input to the user interface. The contract can be in the form of bytecodes for machine interpretation or can be the markup language for human consumption. If there are other contracts that are incorporated by reference, the other contracts are formed in a nested hierarchy similar to program language procedures/subroutines and then embedded inside the contract. At 8, the smart contract is assigned a unique block chain number and inserted into block chain. At 10, the smart contract is sent to one or more recipients, which open the payload and execute the terms of the contract and if specified contractual conditions are met, the smart contract can authorize payment. At 12, if dispute arise, the CMS can graphically decode the contract terms in the smart contract for a judge, jury, or lawyer to apply legal analysis and determine the parties' obligations.

Cloud Storage Security

In another aspect, a distributed file storage system includes nodes are incentivized to store as much of the entire network's data as they can. Blockchain currency is awarded for storing files, and is transferred in Bitcoin or Ether transactions, as in. Files are added to the network by spending currency. This produces strong monetary incentives for individuals to join and work for the network. In the course of ordinary operation of the storage network, nodes contribute useful work in the form of storage and distribution of valuable data.

In another aspect, a method for providing electronic content retrieval with cloud computing is provided. A first request message is received in real-time on the first cloud application stored on the cloud server network device with the one or more processors from a second cloud application. The first request message includes a request for desired cloud electronic content stored in the plural cloud storage objects stored on the selected ones of the plural other different cloud server network devices located on one or more of the networks comprising the cloud communications network. The plural different cloud storage objects function as a single secure storage object for electronic content on the cloud communications network. A cloud content location map is retrieved securely on the first cloud application on the cloud server network device. The cloud content location map includes address locations of the selected ones of the plural other different cloud server network devices on the cloud communications network. The first cloud application on the cloud server network device sends plural second request messages for the desired cloud electronic content to the selected ones of the plural other different cloud server network devices identified in the retrieved cloud content location map and located on one or more of the public communication networks, the one or more private networks, community networks and hybrid networks comprising the cloud communications network. The first cloud application on the first server network device combines the one or more individual components of the desired cloud electronic content from the plural cloud storage objects from the received plural response messages into a final desired electronic cloud content component. The first cloud application on the cloud server network device securely sends in real-time the final desired cloud electronic content component as the request desired cloud electronic content to the target network device via the cloud communications network. The second cloud application on the target network device cannot determine the desired cloud electronic content was split and was stored in plural cloud storage objects and cannot determine which of plural selected ones of the other different cloud server network devices on which ones of the public, private, community or hybrid networks on the cloud communications network may have stored portions of the final desired cloud electronic content, thereby providing a second and/or fourth layer of security and privacy for the desired cloud electronic content on the cloud communications network.

To enable an IOT device such as a car or a robot to access cloud data securely, and to grant access right to agents of the IOT device such as media players in the car, for example, the following methods can be used for accessing data, content, or application stored in a cloud storage, comprising: authorizing a first client device; receiving an authorization request from the first client device; generating an authorization key for accessing the cloud server and storing the key in a blockchain; providing the authorization key to the first client device; receiving the authorization key from an IOT device as a second client device working as an agent of the first client device; granting access to the second client device based on the authorization key; receiving a map of storage locations of cloud objects associated with an application or content, each storage location identified in a blockchain; and reassembling the application or content from the storage locations.

In implementation, the blockchain is decentralized and does not require a central authority for creation, processing or verification and comprises a public digital ledger of all transactions that have ever been executed on the blockchain and wherein new blocks are added to the blockchain in a linear, chronological order. The public digital ledger of the blockchain comprises transactions and blocks. Blocks in the blockchain record and confirm when and in what sequence transactions are entered and logged into the blockchain. The transactions comprise desired electronic content stored in the blockchain. The desired electronic content includes a financial transaction. The financial transaction includes a cryptocurrency transaction, wherein the cryptocurrency transaction includes a BITCOIN or an ETHEREUM transaction. An identifier for the received one or more blocks in the blockchain includes a private encryption key.

Medical History

The above permissioned blockchain can be used to share sensitive medical data with different authorized institutions. The institutions are trusted parties and vouched for by the trusted point. A Patient-Provider Relationship (PPR) Smart Contract is issued when one node from a trusted institution stores and manages medical records for the patient. The PPR defines an assortment of data pointers and associated access permissions that identify the records held by the care provider. Each pointer consists of a query string that, when executed on the provider's database, returns a subset of patient data. The query string is affixed with the hash of this data subset, to guarantee that data have not been altered at the source. Additional information indicates where the provider's database can be accessed in the network, i.e. hostname and port in a standard network topology. The data queries and their associated information are crafted by the care provider and modified when new records are added. To enable patients to share records with others, a dictionary implementation (hash table) maps viewers' addresses to a list of additional query strings. Each string can specify a portion of the patient's data to which the third party viewer is allowed access. For SQL data queries, a provider references the patient's data with a SELECT query on the patient's address. For patients uses an interface that allows them to check off fields they wish to share through a graphical interface. The system formulates the appropriate SQL queries and uploads them to the PPR on the blockchain.

In one embodiment, the transaction 303 includes the recipient's address 324 (e.g., a hash value based on the receiver's public key), the Blockchain token 309 (i.e., a patient ID 328 and personally identifiable information such as Social Security 326), past medical institution relationship information 331 (if any), and optional other information 310. The transaction 323 is digitally signed by the patient who is the sender's private key to create a digital signature 332 for verifying the sender's identity to the network nodes. The network nodes decrypt the digital signature 332, via the sender's previously exchanged public key, and compare the unencrypted information to the transaction 323. If they match, the sender's authenticity is verified and, after a proper chain of ownership is verified via the ledgers (as explained above), the receiver is recorded in the ledgers as the new Blockchain token 329 authorized owner of the medical information. Off-chain storage warehouses can be used for containing the patient's medical history so that the current owner (or all prior owners) can access the patient medical information for treatment. Further, the information can be segmented according to need. This way, if a medication such as cannabis that requires the patient to be an adult, the system can be queried only to the information needed (such as is this patient an adult) and the system can respond only as to the query and there is no need to send other question (in the adult age example, the system replies only adult or not and does not send the birthday to the inquiring system).

In another embodiment, the system includes two look up tables, a global registration look up table (GRLT) where all participants (medical institutions and patients) are recorded with name or identity string, blockchain address for the smart contract, and Patient-Provider lookup table (PPLT). This is maintained by a trusted host authority such as a government health authority or a government payor authority. One embodiment maps participant identification strings to their blockchain address or Ethereum address identity (equivalent to a public key). Terms in the smart contract can regulate registering new identities or changing the mapping of existing ones. Identity registration can thus be restricted only to certified institutions. The PPLT maps identity strings to an address on the blockchain. Patients can poll their PPLT and be notified whenever a new relationship is suggested or an update is available. Patients can accept, reject or delete relationships, deciding which records in their history they acknowledge. The accepting or rejecting relationships is done only by the patients. To avoid notification spamming from malicious participants, only trusted providers can update the status variable. Other contract terms or rules can specify additional verifications to confirm proper actor behavior.

When Provider 1 adds a record for a new patient, using the GRLT on the blockchain, the patient's identifying information is first resolved to their matching Ethereum address and the corresponding PPLT is located. Provider 1 uses a cached GRLT table to look up any existing records of the patient in the PPLT. For all matching PPLTs, Provider 1 broadcasts a smart contract requesting patient information to all matching PPLT entries. If the cache did not produce a result for the patient identity string or blockchain address, Provider 1 can send a broadcast requesting institutions who handles the patient identity string or the blockchain address to all providers. Eventually, Provider 2 responds with its addresses. Provider 2 may insert an entry for Provider 1 into its address resolution table for future use. Provider 1 caches the response information in its table and can now pull information from Provider 2 and/or supplement the information known to Provider 2 with hashed addresses to storage areas controlled by Provider 1.

Next, the provider uploads a new PPR to the blockchain, indicating their stewardship of the data owned by the patient's Ethereum address. The provider node then crafts a query to reference this data and updates the PPR accordingly. Finally, the node sends a transaction which links the new PPR to the patient's PPLT, allowing the patient node to later locate it on the blockchain.

A Database Gatekeeper provides an off-chain, access interface to the trusted provider node's local database, governed by permissions stored on the blockchain. The Gatekeeper runs a server listening to query requests from clients on the network. A request contains a query string, as well as a reference to the blockchain PPR that warrants permissions to run it. The request is cryptographically signed by the issuer, allowing the gatekeeper to confirm identities. Once the issuer's signature is certified, the gatekeeper checks the blockchain contracts to verify if the address issuing the request is allowed access to the query. If the address checks out, it runs the query on the node's local database and returns the result over to the client.

A patient selects data to share and updates the corresponding PPR with the third-party address and query string. If necessary, the patient's node can resolve the third party address using the GRLT on the blockchain. Then, the patient node links their existing PPR with the care provider to the third-party's Summary Contract. The third party is automatically notified of new permissions, and can follow the link to discover all information needed for retrieval. The provider's Database Gatekeeper will permit access to such a request, corroborating that it was issued by the patient on the PPR they share.

In one embodiment that handles persons without previous blockchain history, admitting procedures are performed where the person's personal data is recorded and entered into the blockchain system. This data may include: name, address, home and work telephone number, date of birth, place of employment, occupation, emergency contact information, insurance coverage, reason for hospitalization, allergies to medications or foods, and religious preference, including whether or not one wishes a clergy member to visit, among others. Additional information may include past hospitalizations and surgeries, advance directives such as a living will and a durable power to attorney. During the time spent in admitting, a plastic bracelet will be placed on the person's wrist with their name, age, date of birth, room number, and blockchain medical record reference on it.

The above system can be used to connect the blockchain with different EHR systems at each point of care setting. Any time a patient is registered into a point of care setting, the EHR system sends a message to the GRLT to identify the patient if possible. In our example, Patient A is in registration at a particular hospital. The PPLT is used to identify Patient A as belonging to a particular plan. The smart contracts in the blockchain automatically updates Patient A's care plan. The blockchain adds a recommendation to put Patient A by looking at the complete history of treatments by all providers and optimizes treat. For example, the system can recommend the patient be enrolled in a weight loss program after noticing that the patient was treated for sedentary lifestyle, had history of hypertension, and the family history indicates a potential heart problem. The blockchain data can be used for predictive analytics, allowing patients to learn from their family histories, past care and conditions to better prepare for healthcare needs in the future. Machine learning and data analysis layers can be added to repositories of healthcare data to enable a true "learning health system" can support an additional analytics layer for disease surveillance and epidemiological monitoring, physician alerts if patients repeatedly fill and abuse prescription access.

In one embodiment, an IOT medical device captures patient data in the hospital and automatically communicates data to a hospital database that can be shared with other institutions or doctors. First, the patient ID and blockchain address is retrieved from the patient's wallet and the medical device attaches the blockchain address in a field, along with other fields receiving patient data. Patient data is then stored in a hospital database marked with the blockchain address and annotated by a medical professional with interpretative notes. The notes are affiliated with the medical professional's blockchain address and the PPR block chain address. A professional can also set up the contract terms defining a workflow. For example, if the device is a blood pressure device, the smart contract can have terms that specify dietary restrictions if the patient is diabetic and the blood pressure is borderline and food dispensing machines only show items with low salt and low calorie, for example.

The transaction data may consist of a Colored Coin implementation (described in more detail at https://en.bitcoin.it/wiki/Colored_Coins which is incorporated herein by reference), based on Open Assets (described in more detail at https://github.com/OpenAssets/open-assets-protocol/blob/master/specification.mediawiki which is incorporated herein by reference), using on the OP_RETURN operator. Metadata is linked from the Blockchain and stored on the web, dereferenced by resource identifiers and distributed on public torrent files. The colored coin specification provides a method for decentralized management of digital assets and smart contracts (described in more detail at https://github.com/ethereum/wiki/wiki/White-Paper which is incorporated herein by reference.) For our purposes the smart contract is defined as an event-driven computer program, with state, that runs on a blockchain and can manipulate assets on the blockchain. So a smart contract is implemented in the blockchain scripting language in order to enforce (validate inputs) the terms (script code) of the contract.

Patient Behavior and Risk Pool Rated Health Plans

With the advent of personal health trackers, new health plans are rewarding consumers for taking an active part in their wellness. The system facilitates open distribution of the consumers wellness data and protect it as PHR must be, and therefore prevent lock-in of consumers, providers and payers to a particular device technology or health plan. In particular, since PHR data is managed on the blockchain a consumer and/or company can grant access to a payer to this data such that the payer can perform group analysis of an individual or an entire company's employee base including individual wellness data and generate a risk score of the individual and/or organization. Having this information, payers can then bid on insurance plans tailored for the specific organization. Enrollment then, also being managed on the blockchain, can become a real-time arbitrage process. The pseudo code for the smart contract to implement a patient behavior based health plan is as follows.
store mobile fitness data
store consumer data in keys with phr_info, claim_info, enrollment_info
for each consumer:
add up all calculated risk for the consumer
determine risk score based on mobile fitness data
update health plan cost based on patient behavior Patient and Provider Data Sharing A patient's Health BlockChain wallet stores all assets, which in turn store reference ids to the actual data, whether clinical documents in HL7 or FHIR format, wellness metrics of activity and sleep patterns, or claims and enrollment information. These assets and control of grants of access to them is afforded to the patient alone. A participating provider can be given full or partial access to the data instantaneously and automatically via enforceable restrictions on smart contracts.

Utilizing the Health BlockChain the access to a patient's PHR can be granted as part of scheduling an appointment, during a referral transaction or upon arrival for the visit. And, access can just as easily be removed, all under control of the patient.

Upon arrival at the doctor's office, an application automatically logs into a trusted provider's wireless network. The app is configured to automatically notify the provider's office of arrival and grant access to the patient's PHR. At this point the attending physician will have access to the patient's entire health history. The pseudo code for the smart contract to implement a patient and provider data sharing is as follows.
Patient download apps and provide login credential and logs into the provider wireless network
Patient verifies that the provider wireless network belongs to a patient trusted provider list
Upon entering provider premise, system automatically logs in and grants access to provider
Patient check in data is automatically communicated with provider system to provide PHR
Provider system synchronizes files and obtain new updates to the patient PHR and flags changes to provider.

Patient Data Sharing

Patient's PHR data is valuable information for their personal health profile in order to provide Providers (Physicians) the necessary information for optimal health care delivery. In addition this clinical data is also valuable in an aggregate scenario of clinical studies where this information is analyzed for diagnosis, treatment and outcome. Currently this information is difficult to obtain due to the siloed storage of the information and the difficulty on obtaining patient permissions.

Given a patient Health BlockChain wallet that stores all assets as reference ids to the actual data. These assets can be included in an automated smart contract for clinical study participation or any other data sharing agreement allowed by the patient. The assets can be shared as an instance share by adding to the document a randomized identifier or nonce, similar to a one-time use watermark or serial number, a unique asset (derived from the original source) is then generated for a particular access request and included in a smart contract as an input for a particular request for the patient's health record information. A patient can specify their acceptable terms to the smart contract regarding payment for access to PHR, timeframes for acceptable access, type of PHR data to share, length of history willing to be shared, de-identification thresholds or preferences, specific attributes of the consumer of the data regarding trusted attributes such as reputation, affiliation, purpose, or any other constraints required by the patient. Attributes of the patient's data are also advertised and summarized as properties of the smart contract regarding the type of diagnosis and treatments available. Once the patient has advertised their willingness to share data under certain conditions specified by the smart contract it can automatically be satisfied by any consumer satisfying the terms of the patient and their relevance to the type of PHR needed resulting in a automated, efficient and distributed means for clinical studies to consume relevant PHR for analysis. This process provides an automated execution over the Health BlockChain for any desired time period that will terminate at an acceptable statistical outcome of the required attained significance level or financial limit. The pseudo code for the smart contract to implement automated patient data sharing is as follows.

Patient download apps and provide login credential and logs into the clinical trial provider wireless network
Patient verifies that the provider wireless network belongs to a patient trusted provider list
Upon entering provider premise, system automatically logs in and grants access to provider
Patient check in data is automatically communicated with provider system to provide clinical trial data In one embodiment, a blockchain entry is added for each touchpoint of the medication as it goes through the supply chain from manufacturing where the prescription package serialized numerical identification (SNI) is sent to wholesalers who scan and record the SNI and location and then to distributors, repackagers, and pharmacies, where the SNI/location data is recorded at each touchpoint and put on the blockchain. The medication can be scanned individually, or alternatively can be scanned in bulk. Further, for bulk shipments with temperature and shock sensors for the bulk package, temperature/shock data is captured with the shipment or storage of the medication.

A smart contract assesses against product supply chain rule and can cause automated acceptance or rejection as the medication goes through each supply chain touchpoint. The process includes identifying a prescription drugs by query of a database system authorized to track and trace prescription drugs or similar means for the purpose of monitoring the movements and sale of pharmaceutical products through a supply chain; a.k.a. e-pedigree trail; serialized numerical identification (SNI), stock keeping units (SKU), point of sale system (POS), systems etc. in order to compare the information; e.g. drug name, manufacturer, etc. to the drug identified by the track and trace system and to ensure that it is the same drug and manufacturer of origin. The process can verify authenticity and check pedigree which can be conducted at any point along the prescription drug supply chain; e.g. wholesaler, distributor, doctor's office, pharmacy. The most optimal point for execution of this process would be where regulatory authorities view the greatest vulnerability to the supply chain's integrity. For example, this examination process could occur in pharmacy operations prior to containerization and distribution to the pharmacy for dispensing to patients.

An authenticated prescription drug with verified drug pedigree trail can be used to render an informational object, which for the purpose of illustration will be represented but not be limited to a unique mark; e.g. QR Code, Barcode, Watermark, Stealth Dots, Seal or 2 Dimensional graphical symbol, hereinafter called a certificate, seal, or mark. An exemplary embodiment for use of said certificate, mark, or seal can be used by authorized entities as a warrant of the prescription drug's authenticity and pedigree. For example, when this seal is appended to a prescription vial presented to a patient by a licensed pharmacy, it would represent the prescription drug has gone through an authentication and logistics validation process authorized by a regulatory agency (s); e.g. HHS, FDA, NABP, VIPP, etc. An exemplary embodiment for use of said certificate, mark or seal would be analogous to that of the functioning features, marks, seals, and distinguishing characteristics that currently authenticate paper money and further make it difficult to counterfeit. Furthermore, authorized agents utilizing the certificate process would be analogous to banks participating in the FDIC program.

A user; e.g. patient equipped with the appropriate application on a portable or handheld device can scan the certificate, mark or seal and receive an audible and visible confirmation of the prescription drug's name, and manufacturer. This will constitute a confirmation of the authenticity of the dispensed prescription drug. Extensible use of the certificate, mark, or seal will include but not be limited to; gaining access to website (s) where additional information or interactive functions can be performed; e.g. audible narration of the drug's characteristics and physical property descriptions, dosing, information, and publications, etc. A user; e.g. patient equipped with the appropriate application on a portable or handheld device can scan the certificate, mark, or seal and be provided with notifications regarding; e.g. immediate recall of the medication, adverse events, new formulations, critical warnings of an immediate and emergency nature made by prescription drug regulatory authorities and, or their agents. A user; e.g. patient equipped with a portable or handheld device with the appropriate application software can use the portable and, or handheld device to store prescription drug information in a secure, non-editable format on their device for personal use; e.g. MD's Office Visits, Records Management, Future Authentications, Emergency use by first responders etc. A user; e.g. patient equipped with the appropriate application on a portable or handheld device can scan the drug via an optical scan, picture capture, spectroscopy or other means of identifying its physical properties and characteristics; e.g. spectral signature, size, shape, color, texture, opacity, etc and use this data to identify the prescription drug's name, and manufacturer. A user; e.g. patient equipped with the appropriate application on a portable or handheld device and having the certification system can receive updated information (as a subscriber in a client/server relationship) on a continuing or as needed ad hoc basis (as permitted) about notifications made by prescription drug regulatory authorities regarding; e.g. immediate recall of medications, adverse events, new formulations and critical warnings of an immediate and emergency nature. A user; e.g. patient, subscriber to the certificate system equipped with the appropriate application on a portable or handheld device will be notified by audible and visible warnings of potential adverse affects between drug combinations stored in their device's memory of previously "Certified Drugs." A user; e.g. patient subscriber to the certification system equipped with the appropriate application on a portable or handheld device will receive notification of potential adverse affects from drug combinations, as reported and published by medical professionals in documents and databases reported to; e.g. Drug Enforcement Administration (DEA), Health and Human Services, (HHS) Food and Drug Administration, (FDA) National Library of Medicines, (NLM) and their agents; e.g., Daily Med, Pillbox, RX Scan, PDR, etc.

1. A method for prescription drug authentication by receiving a certificate representing manufacturing origin and distribution touchpoints of a prescription drug on a blockchain.

2. A method of claim 1, comprising retrieving active pharmaceutical ingredients (API) and inactive pharmaceutical ingredients (IPI) from the blockchain.

3. A method of claim 2, comprising authenticating the drug after comparing the API and IPI with data from Drug Enforcement Administration (DEA) Health and Human Services, (HHS) Food and Drug Administration, (FDA) National Library of Medicines, (NLM) etc. for the purpose of identifying the prescription drug'(s) and manufacture name indicated by those ingredients.

4. A method of claim 1, comprising tracing the drug through a supply chain from manufacturer to retailer, dispenser with Pedigree Trail, Serialized Numerical Identification (SNI), Stock Keeping Units (SKU), Point of Sale System (POS) E-Pedigree Systems.

5. A method of claim 1, comprising generating a certificate, seal, mark and computer scannable symbol such as 2 or 3 dimensional symbol; e.g. QR Code, Bar Code, Watermark, Stealth Dots, etc.

Recognition of Exercise Pattern and Tracking of Calorie Consumption

Figure 8A:
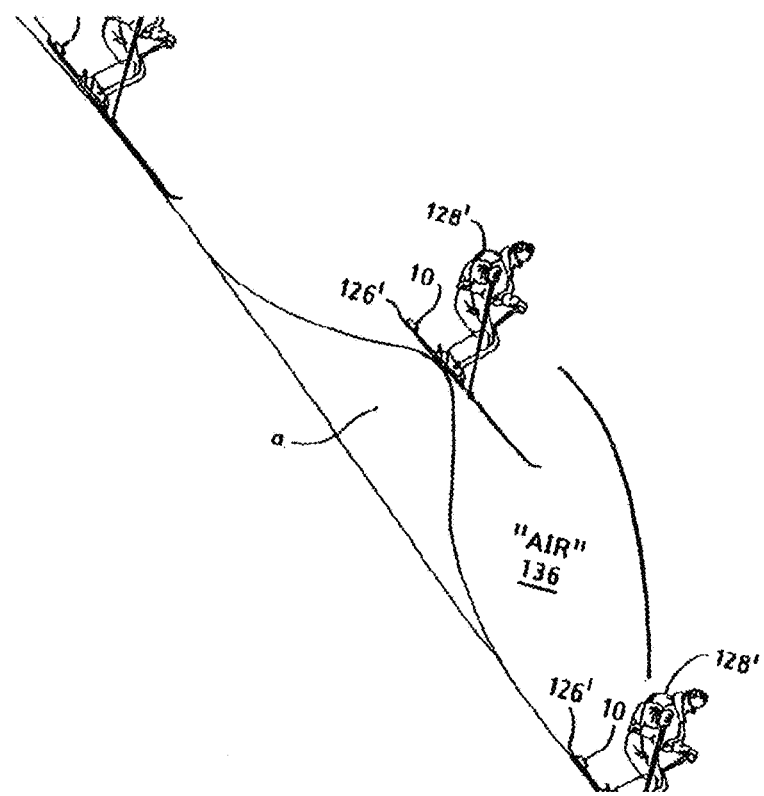

The learning system can be used to detect and monitor user activities as detected by the ITE sensors. FIG. 8A illustrates the positions of a ski 126' and skier 128' during a lofting maneuver on the slope 132'. The ski 126' and skier 128' speed down the slope 132' and launch into the air 136 at position "a," and later land at position "b" in accord with the well-known Newtonian laws of physics. With an airtime sensor, described above, the unit 10 calculates and stores the total airtime that the ski 126' (and hence the skier 128') experiences between the positions "a" and "b" so that the skier 128' can access and assess the "air" time information. Airtime sensors such as the sensor 14 may be constructed with known components. Preferably, the sensor 14 incorporates either an accelerometer or a microphone. Alternatively, the sensor 14 may be constructed as a mechanical switch that detects the presence and absence of weight onto the switch. Other airtime sensors 14 will become apparent in the description which follows. The accelerometer senses vibration—particularly the vibration of a vehicle such as a ski or mountain bike—moving along a surface, e.g., a ski slope or mountain bike trail. This voltage output provides an acceleration spectrum over time; and information about airtime can be ascertained by performing calculations on that spectrum. Based on the information, the system can reconstruct the movement path, the height, the speed, among others and such movement data is used to identify the exercise pattern. For example, the skier may be interested in practicing mogul runs, and the system can identify foot movement and speed and height information and present the information post exercises as feedback. Alternatively, the system can make live recommendations to improve performance to the athlete.

Figure 8B:
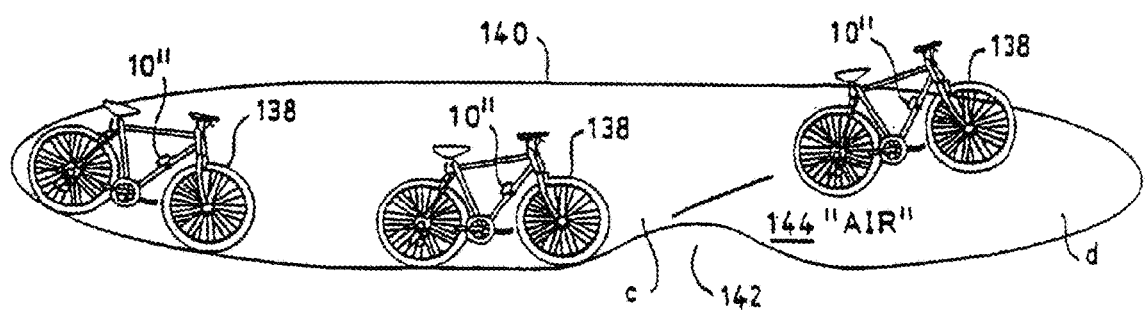
Figure 8C:
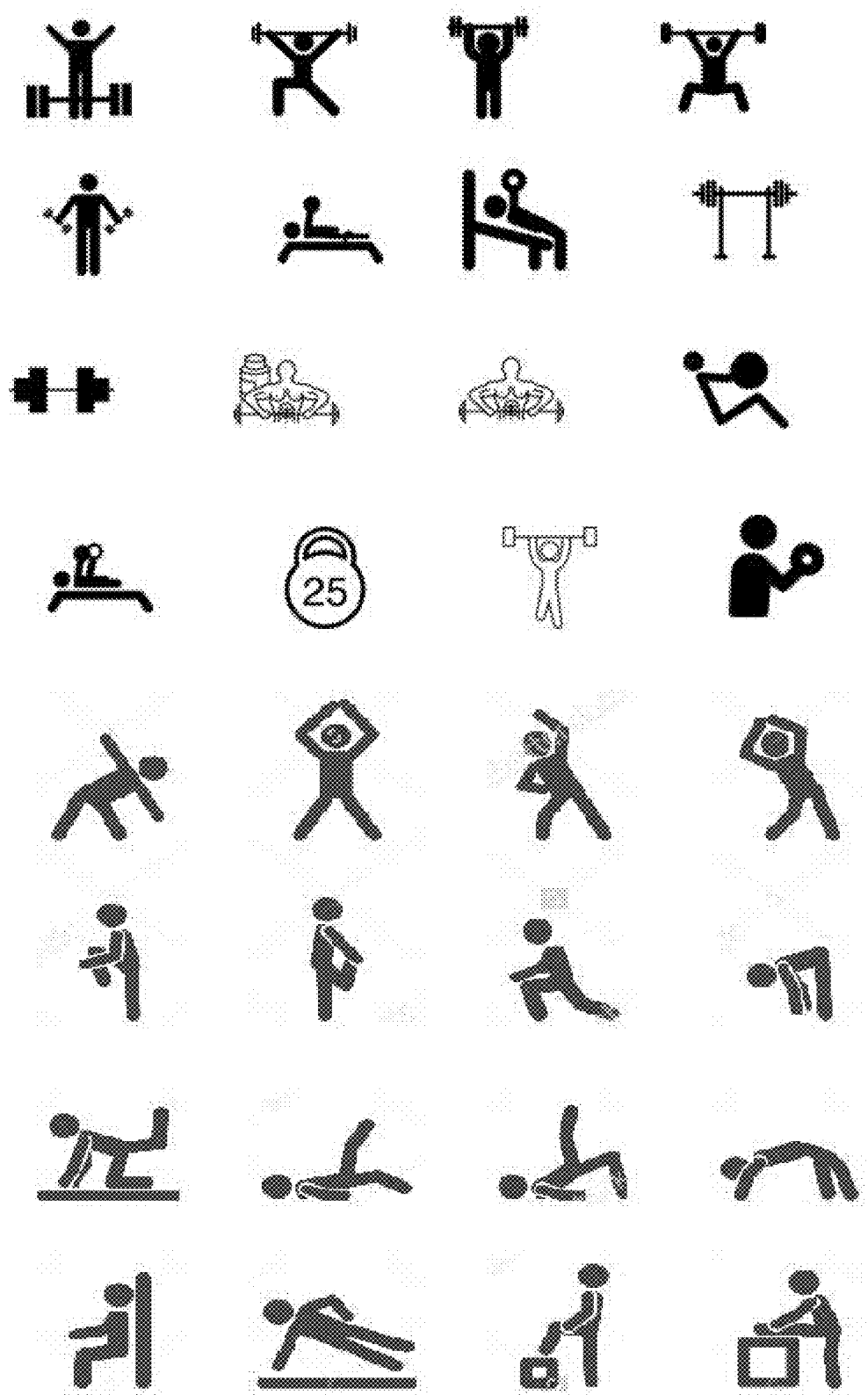
Figure 8D:
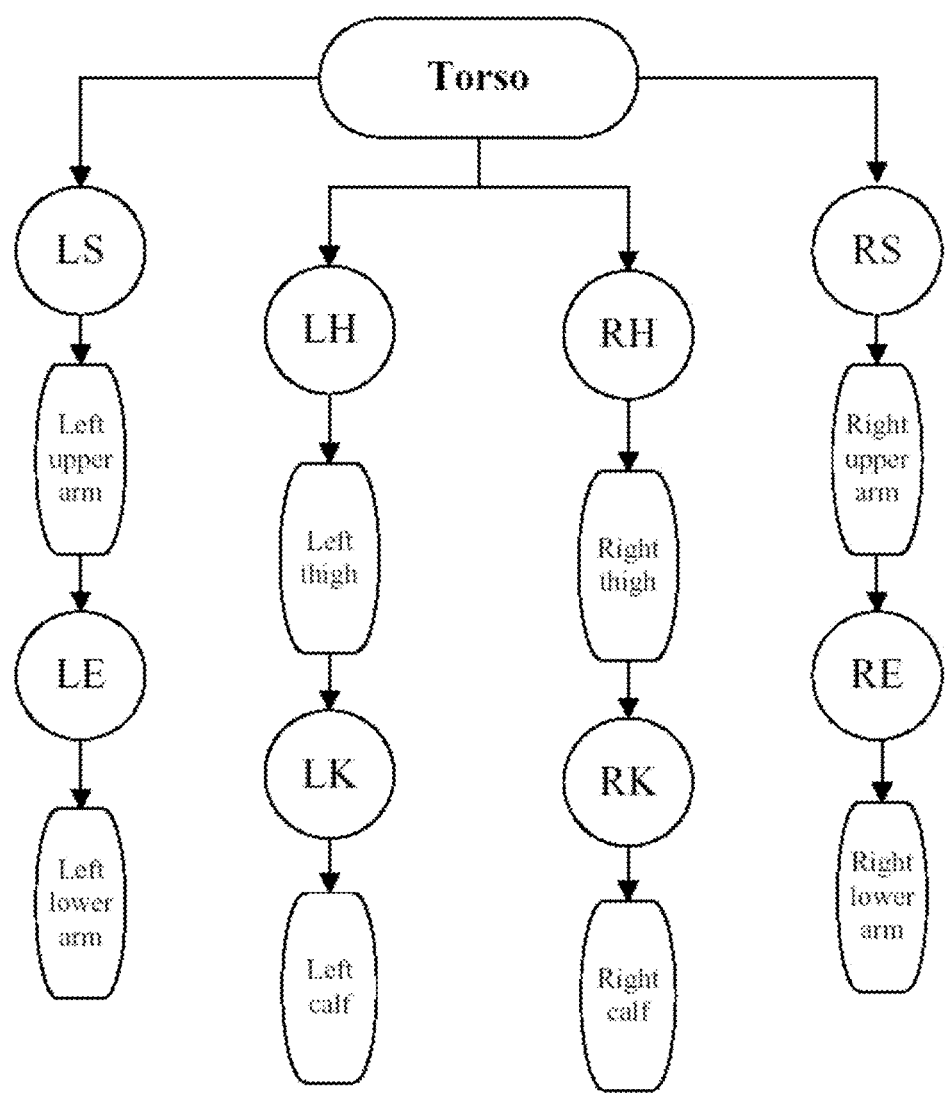
FIG. 8D shows a kinematic modeling for detecting exercise motion which in turn allows precision coaching suggestions, all using data from ear sensors.

FIG. 8B illustrates a sensing unit 10" mounted onto a mountain bike 138. FIG. 8B also shows the mountain bike 138 in various positions during movement along a mountain bike race course 140 (for illustrative purposes, the bike 138 is shown without a rider). At one location "c" on the race course 140, the bike 138 hits a dirt mound 142 and catapults into the air 144. The bike 138 thereafter lands at location "d". As above, with speed and airtime sensors, the unit 10 provides information to a rider of the bike 138 about the speed attained during the ride around the race course 140; as well as information about the airtime between location "c" and "d". In this case, the system can recommend a cadence to be reached by the rider, strengthen of abdominals, back and arms, for example.

For golf exercise, It is beneficial to require the golfer to swing the golf club a plurality of times at each swing position to account for variations in each swing. The swing position at which the golf club is swung can be determined by analysis of the measured acceleration provided by the accelerometer, e.g., the time at which the acceleration changes. Data obtained during the training stage may be entered into a virtual table of swing positions and estimated carrying distances for a plurality of different swing positions and a plurality of different swings. A sample format for such a table is as follows, and includes the averaged carrying distance for each of four different swing positions. The swing analyzer provides a golfer with an excellent estimation of the carrying distance of a golf ball for a golf club swing at a specific swing position because it has been trained on actual swings by the golfer of the same club and conversion of information about these swings into estimated carrying distances. The golfer can improve their golf game since they can better select a club to use to hit a golf club for different situations during a round of golf. Also, the swing pattern is used to identify each club path responsible for the curve of any shot and this information is used to improve the golfer. The direction of the club path relative to the target, out-to-in (fade pattern) or in-to-out (draw pattern), is what I refer to as a players swing pattern. Players that swing from in-to-out will tend to hit draws and players that swing from out-to-in will tend to hit fades. Where the ball is struck on the face of the driver (strike point) can drastically alter the effect of a players swing pattern on ball flight. Thus, the camera detects where the ball is struck, and a computer physics model of ball behavior is presented to the golfer to improve the score. Shots struck off the heel will tend to fade more or draw less and shots struck off the toe will tend to draw more or fade less. Thus, camera images of the shots struck of heel or toe can also be used to provide pattern recognition/prediction and for training purposes.

For tennis, examples of motions determined for improvement are detailed next. The system can detect if the continental grip is achieved. Throwing Action pattern is also detected, as the tennis serve is an upwards throwing action that would deliver the ball into the air if it were a baseball pitch. Ball Toss improvements can be determined when the player lines the straight arm up with the net post and release the ball when your hand reaches eye level. The system checks the forward direction so the player can drive weight (and built up momentum) forward into the ball and into the direction of the serve.

The sensors can work with a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping. The sensors can work with a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot.

The sensors can work with a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

For weight training, the sensor can be in gloves as detailed above, or can be embedded inside the weight itself, or can be in a smart watch, for example. The user would enter an app indicating that the user is doing weight exercises and the weight is identified as a dumbbell, a curl bar, and a bar bell. Based on the arm or leg motion, the system automatically detects the type of weight exercise being done. In one embodiment, with motion patterns captured by glove and sock sensors, the system can automatically detect the following exemplary exercise:
Upper Body:
Chest: Barbell Bench Presses, Barbell Incline Presses, Dumbbell Bench Presses, Dumbbell Incline Presses, Dumbbell Flyes, Cable Crossovers
Back: Pull-Ups, Wide-Grip Lat Pulldowns, One-Arm Dumbbell Rows, Seated Cable Rows, Back Extensions, Straight Arm Pulldowns
Shoulders: Seated Dumbbell Presses, Front Raises, Lateral Raises, Reverse Flyes, Upright Cable Rows, Upright Barbell Rows
Biceps: Alternate Dumbbell Curls, Barbell Curls, Preacher Curls, Concentration Curls, Cable Curls, Hammer Curls
Triceps: Seated Triceps Presses, Lying Triceps Presses, Triceps Kickbacks, Triceps Pushdowns, Cable Extensions, Bench Dips
Lower Body
Quadriceps: Barbell Squats, Leg Presses, Leg Extensions
Hamstrings: Dumbbell Lunges, Straight-Leg Deadlifts, Lying Leg Curls
Calves: Seated Calf Raises, Standing Heel Raises
Abs: Floor Crunches, Oblique Floor Crunches, Decline Crunches, Decline Oblique, Hanging Knee Raises, Reverse Crunches, Cable Crunches, Cable Oblique Crunches In one implementation, an HMM is used to track weight-lifting motor skills or sport enthusiast movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the sport enthusiast on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the sport enthusiast through additional tests to confirm the detected motion.

In one exemplary process for determining exercise in the left or right half of the body, the process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the sport enthusiast to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

In one embodiment, exercise motion data acquired by the accelerometer or multi-axis force sensor is analyzed, as will be discussed below, in order to determine the motion of each exercise stroke during the exercise session (i.e., horizontal vertical or circular). In another embodiment for detecting exercise motion using accelerometer, the first minimum discovered during the scanning is noted as the first xmin and considered to be the start of the first brushstroke. The first maximum x value following the first minimum x value is located and construed to be the middle of the first exercise stroke (where exercise motion changes from one direction to the other). The next xmin value indicates the end of the first brushstroke and the beginning of the next brushstroke. The computer records the data for each brushstroke and continues on through the data to find the next brushstroke, recording each successive motion in memory. For the first brushstroke, the maximum and minimum values of the x coordinate (xmax and xmin) are determined. The Y-direction lengths, Ly1 and Ly2, between the data points just before and just after each of xmax and xmin (xmax+1, xmax-1, and Xmin+1, xmin-1) are then determined. The length Lx along the x axis, between xmax and xmin, is also determined. Next, if Lx is less than 2 and either Ly1 or Ly2 is greater than one, then the motion is construed to be vertical. If Ly1 and Ly2 are both less than one, then the motion is construed to be horizontal. Otherwise, the motion is construed to be circular.

Data obtained from the gyroscope, if one is used, typically does not require a complex analysis. To determine which side of the mouth is being brushed at a particular time, the gyroscope data is scanned to determine when the rotational orientation is greater than 180 degrees, indicating the left side, and when it is less than 180 degrees, indicating the right side. As explained above, top and bottom and gum brushing information can also be obtained, without any calculations, simply by examining the data. The time sequence of data that is acquired during exercise and analyzed as discussed above can be used in a wide variety of ways.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a weight lifting exercise, among others. In one alternative embodiment, angular position sensors, one on each side of the hip joint, can be used to distinguish lying down, sitting, and standing positions. In another embodiment, the system repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

To improve a golf swing, the complex motion of the body first starts with the stance. The system checks that the golfer has a low center of gravity to remain balanced throughout the swing path. The swing starts with the arms moving back in a straight line. When the club head reaches the level of the hip, two things happen: there is a stern wrist cock that acts as a hinge along with the left knee (for a right handed swing), building up its torque by moving into the same line as the belly button before the start of the upswing. As the swing continues to the top of the backswing (again for right handed golf swing), the golfer's left arm should be perfectly straight and his right arm should be hinged at the elbow. The downswing begins with the hips and the lower body rather than the arms and upper body, with emphasis on the wrist cock. As the golfer's hips turn into the shot, the right elbow will drop straight down, hugging the right side of the golfer's torso. As the right elbow drops, the wrists begin to snap through from the wrist cock in the backswing. A solid extension of the arms and good transfer of body should put the golfer leaning up on his right toe, balanced, with the golf club resting on the back of the golfers neck. Importantly, all of the movements occur with precise timing, while the head remains completely still with eyes focused on the ball throughout the entire swing.

The system can identify illnesses and prevent overexertion leading to illnesses such as a stroke. Depending on the severity of the stroke, sport enthusiasts can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Sport enthusiasts with pure motor hemiparesis present with face, arm, and leg weakness. This condition usually affects the extremities equally, but in some cases it affects one extremity more than the other. The most common stroke location in affected sport enthusiasts is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Sport enthusiasts with clumsy-hand dysarthria syndrome experience unilateral hand weakness and dysarthria. The dysarthria is often severe, whereas the hand involvement is more subtle, and sport enthusiasts may describe their hand movements as "awkward." This syndrome is usually caused by an infarct in the pons. Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction—such as neglect, hemianopsia, aphasia, and gaze preference (opposite the side of weakness)—suggest hemispheric dysfunction with involvement of a superficial territory from an atherothrombotic or embolic occlusion of a mainstem vessel or peripheral branch.

To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the sport enthusiast is at rest so that EMG data can be accurately captured or to compensate for motion artifacts in the EMG data in accordance with a linear or non-linear compensation table. In yet another embodiment, the EMG data is used to detect muscle fatigue and to generate a warning to the sport enthusiast to get to a resting place or a notification to a nurse or caregiver to render timely assistance. The amplitude of the EMG signal is stochastic (random) in nature and can be reasonably represented by a Gausian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In one embodiment, the camera captures facial expression and a code such as the Microsoft Emotion API takes a facial expression in an image as an input, and returns the confidence across a set of emotions for each face in the image, as well as bounding box for the face, using the Face API. The emotions detected are anger, contempt, disgust, fear, happiness, neutral, sadness, and surprise. These emotions are understood to be cross-culturally and universally communicated with particular facial expressions. Alternatively, a marker for emotional arousal is galvanic skin response (GSR), also referred to as skin conductance (SC) or electrodermal activity (EDA). EDA modulates the amount of sweat secretion from sweat glands. The amount of sweat glands varies across the human body, being highest in hand and foot regions (200-600 sweat glands per cm2). While sweat secretion plays a major role for thermoregulation and sensory discrimination, changes in skin conductance in hand and foot regions are also triggered quite impressively by emotional stimulation: the higher the arousal, the higher the skin conductance. It is noteworthy to mention that both positive ("happy" or "joyful") and negative ("threatening" or "saddening") stimuli can result in an increase in arousal—and in an increase in skin conductance. Skin conductance is not under conscious control. Instead, it is modulated autonomously by sympathetic activity which drives human behavior, cognitive and emotional states on a subconscious level. Skin conductance therefore offers direct insights into autonomous emotional regulation. It can be used as alternative to self-reflective test procedures, or—even better—as additional source of insight to validate verbal self-reports or interviews of a respondent. Based on the detected emotion, the exercise can be increased, decreased, or stopped altogether.

Data from multiple exercise sessions may be collected and used to compile a history of the user's habits over an extended period of time, enabling the user's trainer to better understand user compliance issues. The trainer can review the data with the user and view the animations of the user's exercise sessions during an office visit, allowing the trainer to better instruct the user in proper brushing technique. The trainer can also review the patient's brushing history over time, to determine whether the patient's exercise technique is improving.

The sensor can be integrated into objects already associated with the sporting activity. In one aspect, the sensing unit is integrated into the ski boot or other boot. In another aspect, the sensing unit is integrated into the binding for a ski boot or snowboarder boot. In still another aspect, the sensing unit is integrated into a ski, snowboard, mountain bike, windsurfer, windsurfer mast, roller blade boot, skate-board, kayak, or other sport vehicle. Collectively, the sport objects such as the ski boot and the variety of sport vehicles are denoted as "sport implements". Accordingly, when the sensing unit is not "stand alone", the housing which integrates the controller subsystem with one or more sensors and battery can be made from the material of the associated sport implement, in whole or in part, such that the sensing unit becomes integral with the sport implement.

A mobile app may be a computer implemented method. A computer program may be provided for executing the app with code for:

(21) capture user motion with accelerometer or gyroscope
(22) capture VR views through camera and process using GPU
(23) capture user emotion using facial recognition or GSR
(24) model user action using kinematic model
(25) compare user action with idea action
(26) coach user on improvement to user sport techniques.

The device can negotiate and enforce agreements with others blockchain smart contracts. The system may include one or more of the following:
code to determine trade settlement amounts and transfers funds automatically,
code to automatically pay coupon payments and returns principal upon bond expiration,
code to determine payout based on claim type and policy coverage,
code to collect insurance based on usage and upon a claim submission, code to determine payout based on claim type and policy coverage,
code to transfer electronic medical record from a source to a destination based on patient consent,
code to anonymously store wearable health data from wearable devices for public health monitoring,
a secured content and code to determine and distributes royalty to an author,
code for storing a stock certificate number with stock quantity, code to determine a share registry or a capitalization table from each stock certificate number and stock quantity, code to distribute shareholder communication from a share registry or a capitalization table, code to collect secure shareholder votes from a share registry or a capitalization table for transparent corporate governance, code to provide financial information to shareholder a share registry or a capitalization table for corporate governance, code to enforce majority or supermajority shareholder votes from a share registry or a capitalization table for corporate governance, code for supply chain management, code for tracking chain of custody for an item, or code for peer-to-peer transactions for between two computers.

Although described with respect to ear bud and flexible ear enclosures, the sensor emitter and detector may be enclosed in any number of housings having various sizes and shapes of ear tissue contact surfaces, may use various types of electrical interconnnect and use various materials so as to noninvasively measure blood parameters from the ear.

The system may include modifying a characteristic of the three-dimensional model to improve the fit. This may include modifying a shell for an earpiece, modifying a shape of the earpiece, selecting different (e.g., firmer or softer) materials for fabrication of the earpiece or otherwise modifying a material profile of the 3D model, and so forth. Modifying the characteristic may also or instead include positioning an articulating joint within the three-dimensional model, e.g., to accommodate axial deformation during insertion/removal of the earpiece. Modifying the characteristic may also or instead include modifying an elasticity of a portion of the three-dimensional model.

It will further be appreciated that, based on the compliance data captured during a scan, a good estimate can be obtained of the maximum short-duration expansion of regions of the ear canal. This data may be useful for modeling the insertion and removal of the earpiece, and modifying the earpiece design accordingly to reduce discomfort during insertion and removal of the earpiece.

It will be readily appreciated that a device such as any of the devices described above may be adapted to perform the method with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method.

It will be appreciated that any of the above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer and/or server or other remote processing resource in a number of ways, or all of the functionality may be integrated into a dedicated, standalone device. All such permutations and combinations are intended to fall within the scope of the present disclosure.

In other embodiments, disclosed herein are computer program products comprising computer-executable code or computer-usable code that, when executing on one or more computing devices, performs any and/or all of the steps described above. The code may be stored in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the processes described above may be embodied in any suitable transmission or propagation medium carrying the computer-executable code described above and/or any inputs or outputs from same.

While the invention has been disclosed in connection with the preferred embodiments shown and described in detail, various modifications and improvements thereon will become readily apparent to those skilled in the art. Accordingly, the spirit and scope of the preferred embodiment is not to be limited by the foregoing examples, but is to be understood in the broadest sense allowable by law.

What is claimed is:

1. A method for assisting a user, comprising:
capturing sound using an in-ear device;
amplifying sound using an amplifier with gain and amplitude controls for a plurality of frequencies; and
applying a learning machine to identify an aural environment and adjust the amplifiers for optimum hearing.

2. The method of claim 1, comprising applying a learning machine to adjust amplifier parameters for a particular environment with a predetermined noise pattern.

3. The method of claim 1, comprising capturing vital signs with the in-ear device with a camera in the ear to detect ear health.

4. The method of claim 1, comprising capturing vital signs with the in-ear device by detecting blood flow with an in-ear sensor.

5. The method of claim 1, comprising capturing vital signs with the in-ear device by detecting with an in-ear sensor blood parameters including carboxyhemoglobin (HbCO), methemoglobin (HbMet) and total hemoglobin (Hbt).

6. The method of claim 1, comprising detecting a physical condition of an ear drum including curvature and surface abnormality.

7. The method of claim 1, comprising capturing vital signs with the in-ear device by detecting body temperature, encephalography (EEG) data, electrocardiogram (ECG) data, or bioimpedance (BI) data in the ear.

8. The method of claim 1, comprising capturing vital signs with the in-ear device by detecting one or more of: alpha rhythm, auditory steady-state response (ASSR), steady-state visual evoked potentials (SSVEP), visually evoked potential (VEP), visually evoked response (VER) and visually evoked cortical potential (VECP), cardiac activity, bioimpedance, speech and breathing.

9. The method of claim 1, comprising detecting alpha rhythm, auditory steady-state response (ASSR), steady-state visual evoked potentials (SSVEP), and visually evoked potential (VEP).

10. The method of claim 1, comprising correlating EEG, ECG, bioimpedance, speech and breathing to determine health.

11. The method of claim 1, comprising correlating cardiac activity, bioimpedance and breathing.

12. The method of claim 1, comprising determining user health by detecting fluid in an ear structure, change in ear color, curvature of the ear structure.

13. The method of claim 1, comprising determining one or more bio-markers from the vital signs and indicating user health.

14. The method of claim 1, wherein the customizing comprises performing a 3D scan inside an ear canal.

15. The method of claim 14, comprising matching predetermined points on the 3D scan to key points on a template and morphing the key points on the template to the predetermined points.

16. The method of claim 1, comprising 3D printing a model from the 3D scan and fabricating the in-ear device.

17. The method of claim 1, comprising correlating genomic biomarkers for diseases to the vital signs from the in-ear device and applying a learning machine to use the vital signs from the in-ear device to predict disease conditions.

18. The method of claim 1, comprising determining a fall based on accelerometer data, vital signs and sound.

19. The method of claim 1, comprising determining loneliness or mental condition based on activity of life data.

20. The method of claim 1, comprising providing a user dashboard showing health data over a period of time and matching research data on the health signals.

21. The method of claim 1, comprising:
 a housing custom;
 a microphone to capture sound coupled to a processor to deliver enhanced sound to the user anatomy;
 an amplifier with gain and amplitude controls; and
 a learning machine to identify an aural environment and adjusting amplifier controls to optimize hearing based on the identified aural environment.

* * * * *